US012806064B2

(12) United States Patent
Johannes et al.

(10) Patent No.: US 12,806,064 B2
(45) Date of Patent: Nov. 24, 2026

(54) FLUID COLLECTION DEVICE HAVING ADJUSTABLE SHAFT PORTION, AND RELATED SYSTEMS AND METHODS

(71) Applicant: PUREWICK CORPORATION, El Cajon, CA (US)

(72) Inventors: Ashley Marie Johannes, Atlanta, GA (US); Pranav Challa, Atlanta, GA (US)

(73) Assignee: PUREWICK CORPORATION, Covington, GA (US)

(*) Notice: Subject to any disclaimer, the term of this patent is extended or adjusted under 35 U.S.C. 154(b) by 871 days.

(21) Appl. No.: 17/754,736

(22) PCT Filed: Oct. 15, 2020

(86) PCT No.: PCT/US2020/055680

§ 371 (c)(1),
(2) Date: Apr. 11, 2022

(87) PCT Pub. No.: WO2021/076695

PCT Pub. Date: Apr. 22, 2021

(65) Prior Publication Data

US 2024/0082047 A1 Mar. 14, 2024

Related U.S. Application Data

(60) Provisional application No. 62/923,279, filed on Oct. 18, 2019.

(51) Int. Cl.
*A61F 5/453* (2006.01)

(52) U.S. Cl.
CPC .................................... *A61F 5/453* (2013.01)

(58) Field of Classification Search
CPC .... A61F 5/453; A61F 6/02; A61F 6/04; A61F 6/005; A61F 2006/043; A61F 2006/045; A61F 2006/044; A61F 2006/047
See application file for complete search history.

(56) References Cited

U.S. PATENT DOCUMENTS 670,602 A 3/1901 Baker
737,443 A 8/1903 Mooers
(Continued)

FOREIGN PATENT DOCUMENTS

AU 2018216821 A1 8/2019
AU 2021299304 A1 2/2023
(Continued)

OTHER PUBLICATIONS

US 9,908,683 B2, 03/2018, Sandhausen et al. (withdrawn)
(Continued)

*Primary Examiner* — Rebecca E Eisenberg
*Assistant Examiner* — Timothy L Flynn
(74) *Attorney, Agent, or Firm* — Ballard Spahr LLP

(57) ABSTRACT

Examples relate to devices, systems, and methods for fluid collection such as urine. The fluid collection device includes a tubular shaft and a receptacle. The tubular shaft has an open end and an inner surface and is adjustable between a first configuration having a first inner circumference sized to receive at least a portion of a penis within the tubular shaft and a second configuration having a second inner circumference smaller than the first inner circumference and sized to contact the penis with the inner surface. The receptacle is connected to the adjustable tubular shaft distal to the open end, and is configured to collect urine discharged from the penis when the penis is positioned within the tubular shaft.

28 Claims, 11 Drawing Sheets

(56) References Cited

U.S. PATENT DOCUMENTS 976,883 A 11/1910 Keagy et al.
1,015,905 A 1/1912 Northrop
1,032,841 A 7/1912 Koenig
1,178,644 A 4/1916 Johnson
1,229,423 A 6/1917 Eckenrode
1,387,726 A 8/1921 Karge
1,742,080 A 12/1929 Jones
1,979,899 A 11/1934 Obrien et al.
2,241,010 A 5/1941 Chipley
2,262,772 A 11/1941 Peder
2,326,881 A 8/1943 Packer
2,379,346 A 6/1945 Farrell
2,485,555 A 10/1949 Bester
2,571,357 A 10/1951 Charles
2,613,670 A 10/1952 Edward
2,616,426 A 11/1952 Adele
2,644,234 A 7/1953 Earl
2,648,335 A 8/1953 Chambers
2,789,560 A 4/1957 Weimer
2,859,786 A 11/1958 Tupper
2,944,551 A 7/1960 Carl
2,968,046 A 1/1961 Duke
2,971,512 A 2/1961 Reinhardt
3,032,038 A 5/1962 Swinn
3,077,883 A 2/1963 Hill
3,087,938 A 4/1963 Hans et al.
3,089,493 A 5/1963 Galindo
3,114,916 A 12/1963 Hadley
3,169,528 A 2/1965 Knox et al.
3,171,506 A 3/1965 Therkel
3,175,719 A 3/1965 Herndon
3,194,238 A 7/1965 Breece
3,198,994 A 8/1965 Hildebrandt et al.
3,221,742 A 12/1965 Egon
3,312,221 A 4/1967 Overment
3,312,981 A 4/1967 McGuire et al.
3,340,876 A 9/1967 Hill
3,349,768 A 10/1967 Keane
3,356,091 A 12/1967 Patterson
3,362,590 A 1/1968 Gene
3,366,116 A 1/1968 Huck
3,368,564 A 2/1968 Selix
3,369,940 A 2/1968 Slautterback
3,398,848 A 8/1968 Donovan
3,400,717 A 9/1968 Bruce et al.
3,406,688 A 10/1968 Bruce
3,411,504 A 11/1968 Glassman
3,424,163 A 1/1969 Gravdahl
3,425,471 A 2/1969 Yates
3,434,565 A 3/1969 Fischer
3,447,536 A 6/1969 Anna
3,511,241 A 5/1970 Lee
3,512,185 A 5/1970 Ellis
3,520,300 A 7/1970 Flower
3,528,423 A 9/1970 Lee
3,608,552 A * 9/1971 Broerman .............. A61F 5/453 604/349
3,613,123 A 10/1971 Langstrom
3,648,698 A 3/1972 Doherty
3,648,700 A 3/1972 Warner
3,651,810 A 3/1972 Ormerod
3,661,155 A 5/1972 Lindan
3,683,918 A 8/1972 Pizzella
3,690,315 A 9/1972 Chittenden et al.
3,699,815 A 10/1972 Holbrook
3,720,554 A 3/1973 Stumpf
3,721,243 A 3/1973 Greth et al.
3,726,277 A 4/1973 Hirschman
3,727,788 A 4/1973 Holbrook
3,730,411 A 5/1973 Brockmuller
3,742,952 A 7/1973 Magers et al.
3,742,953 A 7/1973 Lee
3,757,355 A 9/1973 Allen et al.
3,788,324 A 1/1974 Lim
3,843,016 A 10/1974 Bornhorst et al.
3,863,638 A 2/1975 Rogers et al.
3,863,798 A 2/1975 Kurihara et al.
3,864,759 A 2/1975 Horiuchi
3,865,109 A 2/1975 Elmore et al.
3,881,486 A 5/1975 Fenton
3,881,489 A 5/1975 Hartwell
3,887,032 A 6/1975 Harris
3,915,189 A 10/1975 Holbrook et al.
3,931,650 A 1/1976 Miller
3,931,819 A 1/1976 Weedle
3,964,786 A 6/1976 Mashuda
3,998,228 A * 12/1976 Poidomani ............. A61F 5/453 604/351
3,999,550 A 12/1976 Martin
4,006,793 A 2/1977 Robinson
4,015,604 A 4/1977 Csillag
4,020,843 A 5/1977 Kanall
4,022,211 A 5/1977 Timmons et al.
4,022,213 A 5/1977 Stein
4,023,216 A 5/1977 Li
4,027,776 A 6/1977 Douglas
4,031,897 A 6/1977 Graetz
4,042,337 A 8/1977 Griffith
4,064,962 A 12/1977 Hunt
4,069,817 A 1/1978 Fenole et al.
4,084,589 A 4/1978 Kulvi
4,096,897 A 6/1978 Cammarata
4,116,197 A 9/1978 Bermingham
4,117,845 A 10/1978 Brown
4,140,739 A 2/1979 Cotten
4,180,178 A 12/1979 Turner
4,187,953 A 2/1980 Turner
4,194,508 A 3/1980 Anderson
4,197,849 A 4/1980 Bostick
4,200,102 A 4/1980 Duhamel et al.
4,202,058 A 5/1980 Anderson
4,203,502 A 5/1980 Strader
4,203,503 A 5/1980 Bertotti et al.
4,209,076 A 6/1980 Bertotti et al.
D255,935 S 7/1980 Cullis et al.
4,223,677 A 9/1980 Anderson
4,233,025 A 11/1980 Larson et al.
4,233,978 A 11/1980 Hickey
4,246,901 A 1/1981 Frosch et al.
4,253,542 A 3/1981 Ruspa et al.
4,257,418 A 3/1981 Hessner
4,270,539 A 6/1981 Frosch et al.
4,280,498 A 7/1981 Jensen
4,281,655 A 8/1981 Terauchi
4,292,916 A 10/1981 Bradley et al.
4,330,239 A 5/1982 Gannaway
4,345,341 A 8/1982 Saito
4,349,029 A 9/1982 Mott
4,352,356 A 10/1982 Tong
4,356,012 A 10/1982 Hofstetter
4,360,933 A 11/1982 Kimura et al.
4,365,363 A 12/1982 Windauer
4,372,299 A 2/1983 Fixel
4,375,841 A 3/1983 Vielbig
4,387,726 A 6/1983 Denard
4,403,991 A 9/1983 Hill
4,421,511 A 12/1983 Steer et al.
4,425,130 A 1/1984 Desmarais
4,446,986 A 5/1984 Bowen et al.
4,453,938 A 6/1984 Brendling
4,457,314 A 7/1984 Knowles
4,457,758 A 7/1984 Norton
4,476,879 A 10/1984 Jackson
4,512,771 A 4/1985 Norton
4,526,688 A 7/1985 Schmidt et al.
4,528,703 A 7/1985 Kraus
4,533,354 A 8/1985 Jensen
4,533,357 A 8/1985 Hall
D280,438 S 9/1985 Wendt
4,551,141 A 11/1985 Mcneil
4,553,968 A 11/1985 Komis
4,568,341 A 2/1986 Mitchell et al.
4,581,026 A 4/1986 Schneider
4,583,983 A 4/1986 Einhorn et al.

(56) References Cited

U.S. PATENT DOCUMENTS 4,589,516 A 5/1986 Inoue et al.
4,601,716 A 7/1986 Smith
4,610,675 A 9/1986 Triunfol
4,620,333 A 11/1986 Ritter
4,626,250 A 12/1986 Schneider
4,627,846 A 12/1986 Ternstroem
4,631,061 A 12/1986 Martin
4,645,275 A 2/1987 Pucci
4,650,477 A 3/1987 Johnson
4,655,754 A 4/1987 Richmond et al.
4,656,675 A 4/1987 Fajnsztajn
4,681,570 A 7/1987 Dalton
4,681,572 A 7/1987 Tokarz et al.
4,681,577 A 7/1987 Stern et al.
4,692,160 A 9/1987 Nussbaumer
4,707,864 A 11/1987 Ikematsu et al.
4,713,065 A 12/1987 Koot
4,713,066 A 12/1987 Komis
4,723,953 A 2/1988 Pratt et al.
4,735,841 A 4/1988 Sourdet
4,743,236 A 5/1988 Manschot
4,747,166 A 5/1988 Kuntz
4,752,944 A 6/1988 Conrads et al.
4,759,753 A 7/1988 Schneider et al.
4,769,215 A 9/1988 Ehrenkranz
4,771,484 A 9/1988 Mozell
4,772,280 A 9/1988 Rooyakkers
4,775,458 A 10/1988 Forester
4,784,654 A 11/1988 Beecher
4,790,830 A 12/1988 Hamacher
4,790,835 A 12/1988 Elias
4,791,686 A 12/1988 Taniguchi et al.
4,795,449 A 1/1989 Schneider et al.
4,798,603 A 1/1989 Meyer et al.
4,799,928 A 1/1989 Crowley
4,804,377 A 2/1989 Hanifl et al.
4,812,053 A 3/1989 Bhattacharjee
4,813,943 A 3/1989 Smith
4,820,291 A 4/1989 Terauchi et al.
4,820,297 A 4/1989 Kaufman et al.
4,841,728 A 6/1989 Jean et al.
4,846,818 A 7/1989 Keldahl et al.
4,846,819 A 7/1989 Welch
4,846,824 A 7/1989 Lassen et al.
4,846,909 A 7/1989 Klug et al.
4,857,064 A 8/1989 Mendoza
4,865,595 A 9/1989 Heyden
4,872,299 A 10/1989 Troutner et al.
4,875,898 A 10/1989 Eakin
4,880,417 A 11/1989 Yabrov et al.
4,882,794 A 11/1989 Stewart
4,883,465 A 11/1989 Brennan
4,886,498 A 12/1989 Newton
4,886,508 A 12/1989 Washington
4,886,509 A 12/1989 Mattsson
4,889,532 A 12/1989 Metz et al.
4,889,533 A 12/1989 Beecher
4,890,691 A 1/1990 Ching-ho
4,895,140 A * 1/1990 Bellak ...................... A61F 5/41
600/39
4,903,254 A 2/1990 Haas
4,904,248 A 2/1990 Vaillancourt
D306,759 S 3/1990 D'Alo
4,905,692 A 3/1990 More
4,911,262 A 3/1990 Tani et al.
4,930,997 A 6/1990 Bennett
4,936,838 A 6/1990 Cross et al.
4,950,262 A 8/1990 Takagi
4,955,922 A 9/1990 Terauchi
4,957,487 A 9/1990 Gerow
4,963,134 A 10/1990 Backscheider et al.
4,965,460 A 10/1990 Tanaka et al.
4,986,823 A 1/1991 Anderson et al.
4,987,849 A 1/1991 Sherman
5,002,541 A 3/1991 Conkling et al.
5,004,463 A 4/1991 Nigay
5,013,308 A 5/1991 Sullivan et al.
5,030,229 A 7/1991 Yang
5,031,248 A 7/1991 Kemper
5,045,077 A 9/1991 Blake
5,045,283 A 9/1991 Patel
5,049,144 A 9/1991 Payton
5,053,339 A 10/1991 Patel
5,057,092 A 10/1991 Webster
5,058,088 A 10/1991 Haas et al.
5,071,347 A 12/1991 Mcguire
5,078,707 A 1/1992 Peter
5,084,037 A 1/1992 Barnett
5,100,396 A 3/1992 Zamierowski
5,102,404 A 4/1992 Goldberg et al.
5,112,324 A 5/1992 Wallace
5,134,994 A 8/1992 Say
5,137,033 A 8/1992 Norton
5,147,301 A 9/1992 Ruvio
5,176,667 A 1/1993 Debring
5,195,997 A 3/1993 Carns
5,196,654 A 3/1993 Diflora et al.
5,199,444 A * 4/1993 Wheeler ................... A61F 6/04
128/842
5,203,699 A 4/1993 Mcguire
5,220,137 A 6/1993 Howerton et al.
5,234,419 A 8/1993 Bryant et al.
5,244,458 A 9/1993 Takasu
5,246,454 A 9/1993 Peterson
5,267,988 A 12/1993 Farkas
5,275,307 A 1/1994 Freese
5,282,795 A 2/1994 Finney
5,294,983 A 3/1994 Ersoz et al.
5,295,979 A 3/1994 DeLaurentis et al.
5,295,983 A 3/1994 Kubo
5,300,052 A 4/1994 Kubo
5,304,749 A 4/1994 Crandell
5,312,383 A 5/1994 Kubalak
5,318,550 A 6/1994 Cermak et al.
5,330,457 A 7/1994 Cohen
5,330,459 A 7/1994 Lavon et al.
5,334,174 A 8/1994 Street
5,334,176 A 8/1994 Buenger et al.
5,340,840 A 8/1994 Park et al.
D354,129 S 1/1995 Salvadori
D354,560 S 1/1995 Chase
5,382,244 A 1/1995 Telang
5,397,315 A 3/1995 Schmidt et al.
5,409,014 A 4/1995 Napoli et al.
5,409,475 A 4/1995 Steer
5,411,495 A 5/1995 Willingham
5,423,784 A 6/1995 Metz
5,423,788 A 6/1995 Rollins et al.
5,437,836 A 8/1995 Yamada
5,455,091 A 10/1995 Oreglia et al.
5,456,246 A 10/1995 Schmieding et al.
5,466,229 A 11/1995 Elson et al.
5,478,334 A 12/1995 Bernstein
5,499,977 A 3/1996 Marx
5,525,407 A 6/1996 Yang
5,543,042 A 8/1996 Filan et al.
D373,928 S 9/1996 Green
5,582,604 A 12/1996 Ahr et al.
5,592,950 A 1/1997 Kopelowicz
5,593,389 A 1/1997 Chang
5,605,161 A 2/1997 Cross
5,614,699 A 3/1997 Yashiro et al.
5,618,277 A 4/1997 Goulter
5,628,735 A 5/1997 Skow
5,632,736 A 5/1997 Block
5,636,643 A 6/1997 Argenta et al.
5,637,104 A 6/1997 Ball et al.
5,641,277 A 6/1997 Gondek
D380,543 S 7/1997 Piontek et al.
5,662,633 A 9/1997 Doak et al.
5,674,212 A 10/1997 Osborn et al.
5,678,564 A 10/1997 Lawrence et al.
5,678,654 A 10/1997 Uzawa
5,681,297 A 10/1997 Hashimoto et al.

(56) References Cited

U.S. PATENT DOCUMENTS 5,687,429 A 11/1997 Rahlff
5,695,485 A * 12/1997 Duperret .............. A61F 13/471 604/352
5,695,487 A 12/1997 Cohen et al.
5,700,254 A 12/1997 Mcdowall et al.
5,701,612 A 12/1997 Daneshvar
5,705,777 A 1/1998 Flanigan et al.
5,735,835 A 4/1998 Holland
5,735,837 A 4/1998 Ishikawa
5,752,944 A 5/1998 Dann et al.
5,763,333 A 6/1998 Suzuki et al.
5,772,644 A 6/1998 Bark et al.
5,792,132 A 8/1998 Garcia
5,827,243 A 10/1998 Palestrant
5,827,247 A 10/1998 Kay
5,827,250 A 10/1998 Fujioka et al.
5,827,257 A 10/1998 Fujioka et al.
D401,699 S 11/1998 Herchenbach et al.
5,859,393 A 1/1999 Cummins et al.
5,865,378 A 2/1999 Hollinshead et al.
5,873,869 A 2/1999 Hammons et al.
5,876,393 A 3/1999 Ahr et al.
5,887,291 A 3/1999 Bellizzi
5,891,125 A 4/1999 Plumley
5,894,608 A 4/1999 Birbara
5,895,349 A 4/1999 Tihon
D409,303 S 5/1999 Oepping
5,911,222 A 6/1999 Lawrence et al.
5,956,782 A 9/1999 Olguin
5,957,904 A 9/1999 Holland
5,968,026 A 10/1999 Osborn et al.
5,972,505 A 10/1999 Phillips et al.
5,984,045 A 11/1999 Maeda et al.
5,991,932 A 11/1999 Wagner
6,007,524 A 12/1999 Schneider
6,007,526 A 12/1999 Passalaqua et al.
D421,307 S 2/2000 Harmanoglu
6,039,060 A 3/2000 Rower
6,050,983 A 4/2000 Moore et al.
6,059,762 A 5/2000 Boyer et al.
6,061,905 A 5/2000 Logic
6,063,064 A 5/2000 Tuckey et al.
6,068,477 A 5/2000 Mahlmann
6,083,602 A 7/2000 Caldwell et al.
6,098,625 A 8/2000 Winkler
6,105,174 A 8/2000 Karlsten et al.
6,113,582 A 9/2000 Dwork
6,117,163 A 9/2000 Bierman
6,123,398 A 9/2000 Arai et al.
6,129,718 A 10/2000 Wada et al.
6,131,964 A 10/2000 Sareshwala
6,152,902 A 11/2000 Christian et al.
6,164,569 A 12/2000 Hollinshead et al.
6,177,606 B1 1/2001 Etheredge et al.
6,209,142 B1 4/2001 Mattsson et al.
6,220,050 B1 4/2001 Cooksey
6,244,311 B1 6/2001 Hand et al.
6,248,096 B1 6/2001 Dwork et al.
6,263,887 B1 7/2001 Dunn
6,283,246 B1 9/2001 Nishikawa
6,296,627 B1 10/2001 Edwards
6,311,339 B1 11/2001 Kraus
6,316,688 B1 11/2001 Hammons et al.
6,336,919 B1 1/2002 Davis et al.
6,338,729 B1 1/2002 Wada et al.
6,352,525 B1 3/2002 Wakabayashi
6,394,988 B1 5/2002 Hashimoto
6,395,956 B1 5/2002 Glasgow et al.
6,398,742 B1 6/2002 Kim
6,406,463 B1 6/2002 Brown
6,409,712 B1 6/2002 Dutari et al.
6,415,888 B2 7/2002 An et al.
6,416,500 B1 7/2002 Wada et al.
6,417,750 B1 7/2002 Sohn
6,423,045 B1 7/2002 Wise et al.
6,428,521 B1 8/2002 Droll
6,428,522 B1 8/2002 Dipalma et al.
6,446,454 B1 9/2002 Lee et al.
6,461,340 B1 10/2002 Lenker et al.
6,467,570 B1 10/2002 Herold
6,475,198 B1 11/2002 Lipman et al.
6,479,726 B1 11/2002 Cole et al.
6,491,673 B1 12/2002 Palumbo et al.
6,508,794 B1 1/2003 Palumbo et al.
6,524,292 B1 2/2003 Dipalma et al.
6,526,603 B1 3/2003 Murphy
6,540,729 B1 4/2003 Wada et al.
6,547,771 B2 4/2003 Robertson et al.
6,551,293 B1 4/2003 Mitchell
6,569,133 B2 5/2003 Cheng et al.
6,571,910 B2 6/2003 Storm
D476,518 S 7/2003 Doppelt
6,592,560 B2 7/2003 Snyder et al.
6,610,038 B1 8/2003 Dipalma et al.
6,618,868 B2 9/2003 Minnick
6,620,142 B1 9/2003 Flueckiger
6,629,651 B1 10/2003 Male et al.
6,635,037 B1 10/2003 Bennett
6,635,038 B2 10/2003 Scovel
6,652,495 B1 11/2003 Walker
6,666,850 B1 12/2003 Ahr et al.
6,685,684 B1 2/2004 Falconer
6,695,828 B1 2/2004 Dipalma et al.
6,699,174 B1 3/2004 Bennett
6,700,034 B1 3/2004 Lindsay et al.
6,702,793 B1 3/2004 Sweetser et al.
6,706,027 B2 3/2004 Harvie et al.
6,732,384 B2 5/2004 Scott
6,736,977 B1 5/2004 Hall et al.
6,740,066 B2 5/2004 Wolff et al.
6,764,477 B1 7/2004 Chen et al.
6,783,519 B2 8/2004 Samuelsson
6,796,974 B2 9/2004 Palumbo et al.
6,814,547 B2 11/2004 Childers et al.
6,848,719 B2 2/2005 Rowley
6,849,065 B2 2/2005 Schmidt et al.
6,857,137 B2 2/2005 Otto
6,878,647 B1 4/2005 Rezai et al.
6,885,690 B2 4/2005 Aggerstam et al.
6,888,044 B2 5/2005 Fell et al.
6,893,425 B2 5/2005 Dunn et al.
6,912,737 B2 7/2005 Ernest et al.
6,918,899 B2 7/2005 Harvie
6,979,324 B2 12/2005 Bybordi et al.
7,018,366 B2 3/2006 Easter
7,018,367 B2 3/2006 Nava
7,066,411 B2 6/2006 Male et al.
7,087,043 B2 8/2006 Dolan
7,122,023 B1 10/2006 Hinoki
7,125,399 B2 10/2006 Miskie
7,131,964 B2 11/2006 Harvie
7,135,012 B2 11/2006 Harvie
7,141,043 B2 11/2006 Harvie
D533,972 S 12/2006 La
7,160,273 B2 1/2007 Greter et al.
7,166,092 B2 1/2007 Elson et al.
7,171,699 B2 2/2007 Ernest et al.
7,171,871 B2 2/2007 Kozak
7,179,951 B2 2/2007 Krishnaswamy-Mirle et al.
7,181,781 B1 2/2007 Trabold et al.
7,186,245 B1 3/2007 Cheng et al.
7,192,424 B2 3/2007 Cooper
7,219,764 B1 5/2007 Forbes
7,220,250 B2 5/2007 Suzuki et al.
D562,975 S 2/2008 Otto
7,335,189 B2 2/2008 Harvie
7,347,691 B1 3/2008 Kelly
7,358,282 B2 4/2008 Krueger et al.
7,390,320 B2 6/2008 Machida et al.
7,438,706 B2 10/2008 Koizumi et al.
7,488,310 B2 2/2009 Yang
7,491,194 B1 2/2009 Oliwa
D591,106 S 4/2009 Dominique et al.
7,513,381 B2 4/2009 Heng et al.

(56) References Cited

U.S. PATENT DOCUMENTS 7,520,872 B2 4/2009 Biggie et al.
D593,801 S 6/2009 Wilson et al.
7,540,364 B2 6/2009 Sanderson
7,549,511 B2 6/2009 Marocco
7,549,512 B2 6/2009 Newberry
7,585,293 B2 9/2009 Vermaak
7,588,560 B1 9/2009 Dunlop
7,637,905 B2 12/2009 Saadat et al.
7,658,730 B2 2/2010 Conley
7,665,359 B2 2/2010 Barber
7,682,347 B2 3/2010 Parks et al.
7,687,004 B2 3/2010 Allen
7,695,459 B2 4/2010 Gilbert et al.
7,695,460 B2 4/2010 Wada et al.
7,699,818 B2 4/2010 Gilbert
7,699,831 B2 4/2010 Bengtson et al.
7,700,819 B2 4/2010 Ambrosio et al.
7,722,584 B2 5/2010 Tanaka et al.
7,727,206 B2 6/2010 Gorres
7,740,620 B2 6/2010 Gilbert et al.
7,749,205 B2 7/2010 Tazoe et al.
7,755,497 B2 7/2010 Wada et al.
7,766,887 B2 8/2010 Burns et al.
7,803,144 B1 9/2010 Vollrath
D625,407 S 10/2010 Koizumi et al.
7,806,879 B2 10/2010 Brooks et al.
7,811,272 B2 10/2010 Lindsay et al.
7,815,067 B2 10/2010 Matsumoto et al.
7,833,169 B2 11/2010 Hannon
7,857,806 B2 12/2010 Karpowicz et al.
7,866,942 B2 1/2011 Harvie
7,871,385 B2 1/2011 Levinson et al.
7,875,010 B2 1/2011 Frazier et al.
7,901,389 B2 3/2011 Mombrinie
7,927,320 B2 4/2011 Goldwasser et al.
7,927,321 B2 4/2011 Marland
7,931,634 B2 4/2011 Swiecicki et al.
7,939,706 B2 5/2011 Okabe et al.
7,946,443 B2 5/2011 Stull et al.
7,947,025 B2 5/2011 Buglino et al.
7,963,419 B2 6/2011 Burney et al.
7,976,519 B2 7/2011 Bubb et al.
7,981,087 B2 7/2011 Gesler, III
7,993,318 B2 8/2011 Olsson et al.
8,015,627 B2 9/2011 Baker et al.
8,016,071 B1 9/2011 Martinus et al.
8,028,460 B2 10/2011 Williams
8,047,398 B2 11/2011 Dimartino et al.
8,075,538 B2 12/2011 Vernon
8,083,026 B1 12/2011 Butler
8,083,094 B2 12/2011 Caulfield et al.
8,128,608 B2 3/2012 Thevenin
8,156,941 B1 4/2012 Simms
8,167,860 B1 5/2012 Siegel
8,181,651 B2 5/2012 Pinel
8,181,819 B2 5/2012 Burney et al.
8,211,063 B2 7/2012 Bierman et al.
8,221,369 B2 7/2012 Parks et al.
8,241,262 B2 8/2012 Mahnensmith
8,277,426 B2 10/2012 Wilcox et al.
8,287,508 B1 10/2012 Sanchez
8,303,554 B2 11/2012 Tsai et al.
8,322,565 B2 12/2012 Caulfield et al.
8,337,477 B2 12/2012 Parks et al.
D674,241 S 1/2013 Bickert et al.
8,343,122 B2 1/2013 Gorres
8,343,125 B2 1/2013 Kawazoe et al.
8,353,074 B2 1/2013 Krebs
8,353,886 B2 1/2013 Bester et al.
D676,241 S 2/2013 Merrill
8,388,587 B1 3/2013 Gmuer et al.
8,388,588 B2 3/2013 Wada et al.
D679,807 S 4/2013 Burgess et al.
8,425,482 B2 4/2013 Khoubnazar
8,430,855 B2 4/2013 Burgess et al.
8,434,586 B2 5/2013 Pawelski et al.
8,449,510 B2 5/2013 Martini et al.
D684,260 S 6/2013 Lund et al.
8,470,230 B2 6/2013 Caulfield et al.
8,479,941 B2 7/2013 Matsumoto et al.
8,479,949 B2 7/2013 Henkel
8,500,719 B1 8/2013 Simpson et al.
8,512,301 B2 8/2013 Ma
8,529,530 B2 9/2013 Koch et al.
8,535,284 B2 9/2013 Joder et al.
8,546,639 B2 10/2013 Wada et al.
8,551,062 B2 10/2013 Kay
8,551,075 B2 10/2013 Bengtson
8,568,376 B2 10/2013 Delattre et al.
D694,404 S 11/2013 Burgess et al.
8,585,683 B2 11/2013 Bengtson et al.
8,586,583 B2 11/2013 Hamblin et al.
8,652,112 B2 2/2014 Johannison et al.
8,669,412 B2 3/2014 Fernkvist et al.
D702,973 S 4/2014 Norland et al.
8,702,667 B1 4/2014 Johnson
8,703,032 B2 4/2014 Menon et al.
D704,330 S 5/2014 Cicatelli
D704,510 S 5/2014 Mason et al.
D705,423 S 5/2014 Walsh Cutler
D705,926 S 5/2014 Burgess et al.
8,714,394 B2 5/2014 Wulf
8,715,267 B2 5/2014 Bengtson et al.
8,740,852 B2 6/2014 Aviles
8,757,425 B2 6/2014 Copeland
8,777,032 B2 7/2014 Biesecker et al.
8,808,260 B2 8/2014 Koch et al.
8,839,792 B2 9/2014 Brunner
8,864,730 B2 10/2014 Conway et al.
8,881,923 B2 11/2014 Higginson
8,882,731 B2 11/2014 Suzuki et al.
8,936,585 B2 1/2015 Carson et al.
D729,581 S 5/2015 Boroski
9,028,460 B2 5/2015 Medeiros
9,056,698 B2 6/2015 Noer
9,078,792 B2 7/2015 Ruiz
9,145,879 B2 9/2015 Pirovano et al.
9,173,602 B2 11/2015 Gilbert
9,173,799 B2 11/2015 Tanimoto et al.
9,187,220 B2 11/2015 Biesecker et al.
9,199,772 B2 12/2015 Krippendorf
9,233,020 B2 1/2016 Matsumiya
9,248,058 B2 2/2016 Conway et al.
9,308,118 B1 4/2016 Dupree et al.
9,309,029 B2 4/2016 Incorvia et al.
9,333,281 B2 5/2016 Giezendanner et al.
9,381,108 B2 7/2016 Longoni et al.
9,382,047 B2 7/2016 Schmidtner et al.
9,402,424 B2 8/2016 Roy
9,415,191 B2 8/2016 Aviles
9,456,937 B2 10/2016 Ellis
9,480,595 B2 11/2016 Baham et al.
9,517,865 B2 12/2016 Albers et al.
D777,941 S 1/2017 Piramoon
9,533,806 B2 1/2017 Ding et al.
9,550,611 B2 1/2017 Hodge
9,555,930 B2 1/2017 Campbell et al.
9,585,805 B2 3/2017 Saitoh et al.
9,623,159 B2 4/2017 Locke
D789,522 S 6/2017 Burgess et al.
9,687,849 B2 6/2017 Bruno et al.
9,694,949 B2 7/2017 Hendricks et al.
9,709,048 B2 7/2017 Kinjo
9,713,547 B2 7/2017 Lee et al.
9,732,754 B2 8/2017 Huang et al.
9,737,433 B2 8/2017 Joh
9,752,564 B2 9/2017 Arceno et al.
9,788,992 B2 10/2017 Harvie
D804,907 S 12/2017 Sandoval
D806,236 S 12/2017 Lin
9,868,564 B2 1/2018 Mcgirr et al.
D814,239 S 4/2018 Arora
D817,484 S 5/2018 Lafond
9,968,908 B2 5/2018 Ladrech et al.

(56) References Cited

U.S. PATENT DOCUMENTS

| | | | |
|---|---|---|---|
| 10,010,393 | B1 | 7/2018 | Nguyen et al. |
| 10,037,640 | B2 | 7/2018 | Gordon |
| 10,058,470 | B2 | 8/2018 | Phillips |
| 10,098,990 | B2 | 10/2018 | Koch et al. |
| D835,264 | S | 12/2018 | Mozzicato et al. |
| D835,779 | S | 12/2018 | Mozzicato et al. |
| D840,533 | S | 2/2019 | Mozzicato et al. |
| D840,534 | S | 2/2019 | Mozzicato et al. |
| 10,225,376 | B2 | 3/2019 | Perez Martinez |
| 10,226,376 | B2 | 3/2019 | Sanchez et al. |
| 10,258,517 | B1 | 4/2019 | Maschino et al. |
| D848,612 | S | 5/2019 | Mozzicato et al. |
| 10,307,305 | B1 | 6/2019 | Hodges |
| 10,335,121 | B2 | 7/2019 | Desai |
| D856,512 | S | 8/2019 | Cowart et al. |
| 10,376,406 | B2 | 8/2019 | Newton |
| 10,376,407 | B2 | 8/2019 | Newton |
| 10,390,989 | B2 | 8/2019 | Sanchez et al. |
| D858,144 | S | 9/2019 | Fu |
| 10,406,039 | B2 | 9/2019 | Mllarreal |
| 10,407,222 | B2 | 9/2019 | Allen |
| 10,478,356 | B2 | 11/2019 | Griffin |
| 10,500,108 | B1 | 12/2019 | Maschino et al. |
| 10,502,198 | B2 | 12/2019 | Stumpf et al. |
| 10,538,366 | B2 | 1/2020 | Pentelovitch et al. |
| 10,569,938 | B2 | 2/2020 | Zhao et al. |
| 10,577,156 | B2 | 3/2020 | Dagnelie et al. |
| RE47,930 | E | 4/2020 | Cho |
| 10,618,721 | B2 | 4/2020 | Vazin |
| D884,390 | S | 5/2020 | Wang |
| 10,669,079 | B2 | 6/2020 | Freedman et al. |
| D892,315 | S | 8/2020 | Airy |
| 10,730,672 | B2 | 8/2020 | Bertram et al. |
| 10,737,848 | B2 | 8/2020 | Philip et al. |
| 10,765,854 | B2 | 9/2020 | Law et al. |
| 10,766,670 | B2 | 9/2020 | Kittmann |
| 10,799,386 | B1 | 10/2020 | Harrison |
| 10,806,623 | B2 | 10/2020 | VanMiddendorp et al. |
| 10,806,642 | B2 | 10/2020 | Tagomori et al. |
| D901,214 | S | 11/2020 | Hu |
| 10,849,799 | B2 | 12/2020 | Nishikawa et al. |
| 10,857,025 | B2 | 12/2020 | Davis et al. |
| 10,865,017 | B1 | 12/2020 | Cowart et al. |
| 10,889,412 | B2 | 1/2021 | West et al. |
| 10,913,581 | B2 | 2/2021 | Stahlecker |
| D912,244 | S | 3/2021 | Rehm et al. |
| 10,952,889 | B2 | 3/2021 | Newton et al. |
| 10,973,378 | B2 | 4/2021 | Ryu et al. |
| 10,973,678 | B2 | 4/2021 | Newton et al. |
| 10,974,874 | B2 | 4/2021 | Ragias et al. |
| 11,000,401 | B2 | 5/2021 | Ecklund et al. |
| 11,002,165 | B2 | 5/2021 | Poulin |
| D923,365 | S | 6/2021 | Wang |
| 11,020,567 | B2 | 6/2021 | Rule et al. |
| 11,026,829 | B2 | 6/2021 | Harvie |
| 11,027,900 | B2 | 6/2021 | Liu |
| 11,045,346 | B2 | 6/2021 | Argent et al. |
| D928,946 | S | 8/2021 | Sanchez et al. |
| 11,090,183 | B2 | 8/2021 | Sanchez et al. |
| 11,160,695 | B2 | 11/2021 | Febo et al. |
| 11,160,697 | B2 | 11/2021 | Maschino et al. |
| 11,168,420 | B2 | 11/2021 | Kinugasa et al. |
| 11,179,506 | B2 | 11/2021 | Barr et al. |
| 11,199,116 | B2 | 12/2021 | Ostromecki et al. |
| 11,207,206 | B2 | 12/2021 | Sharma et al. |
| D941,998 | S | 1/2022 | Tretheway et al. |
| 11,226,376 | B2 | 1/2022 | Yamauchi et al. |
| 11,253,389 | B2 | 2/2022 | Sharma et al. |
| 11,253,407 | B2 | 2/2022 | Miao et al. |
| 11,326,586 | B2 | 5/2022 | Milner et al. |
| 11,369,508 | B2 | 6/2022 | Ecklund et al. |
| 11,369,524 | B2 | 6/2022 | Hubbard et al. |
| 11,376,152 | B2 | 7/2022 | Sanchez et al. |
| 11,382,786 | B2 | 7/2022 | Sanchez et al. |
| 11,382,788 | B2 | 7/2022 | Hjorth et al. |
| 11,389,318 | B2 | 7/2022 | Radl et al. |
| 11,395,871 | B2 | 7/2022 | Radl et al. |
| 11,399,990 | B2 | 8/2022 | Suyama |
| 11,426,303 | B2 | 8/2022 | Davis et al. |
| 11,446,174 | B2 | 9/2022 | Newton |
| 11,504,265 | B2 | 11/2022 | Godinez et al. |
| 11,529,252 | B2 | 12/2022 | Glithero et al. |
| 11,547,788 | B2 | 1/2023 | Radl et al. |
| 11,628,086 | B2 | 4/2023 | Newton et al. |
| 11,702,969 | B2 | 7/2023 | Bartu et al. |
| 11,806,266 | B2 | 11/2023 | Sanchez et al. |
| 11,813,189 | B2 | 11/2023 | Hussey et al. |
| 11,839,567 | B2 | 12/2023 | Davis et al. |
| D1,010,109 | S | 1/2024 | Ecklund et al. |
| 11,857,716 | B2 | 1/2024 | Lee et al. |
| 11,865,030 | B2 | 1/2024 | Davis et al. |
| 11,877,948 | B2 | 1/2024 | Pinlac |
| 11,890,221 | B2 | 2/2024 | Ulreich et al. |
| 11,911,160 | B2 | 2/2024 | Woodard et al. |
| 11,925,575 | B2 | 3/2024 | Newton |
| 11,938,053 | B2 | 3/2024 | Austermann et al. |
| 11,944,740 | B2 | 4/2024 | Hughett et al. |
| 11,994,122 | B2 | 5/2024 | Bodain |
| 11,998,475 | B2 | 6/2024 | Becker et al. |
| 12,023,457 | B2 | 7/2024 | Mann et al. |
| 12,029,678 | B2 | 7/2024 | Newton |
| 12,042,422 | B2 | 7/2024 | Davis et al. |
| 12,042,423 | B2 | 7/2024 | Cheng et al. |
| 12,048,643 | B2 | 7/2024 | Cheng et al. |
| 12,048,644 | B2 | 7/2024 | Davis |
| D1,038,385 | S | 8/2024 | Ecklund et al. |
| 12,064,372 | B2 | 8/2024 | Godinez et al. |
| 12,070,432 | B2 | 8/2024 | Tourchak et al. |
| 12,090,083 | B2 | 9/2024 | Ecklund et al. |
| 12,121,468 | B2 | 10/2024 | Sanchez et al. |
| 12,133,813 | B2 | 11/2024 | Ulreich et al. |
| 12,138,195 | B2 | 11/2024 | Alder et al. |
| D1,054,019 | S | 12/2024 | Miyawaki |
| 12,161,579 | B2 | 12/2024 | Sanchez et al. |
| D1,059,585 | S | 1/2025 | Miyawaki |
| D1,059,586 | S | 1/2025 | Miyawaki |
| 12,186,229 | B2 | 1/2025 | Davis et al. |
| 12,193,962 | B2 | 1/2025 | Newton et al. |
| 12,208,031 | B2 | 1/2025 | Knapp et al. |
| 12,233,003 | B2 | 2/2025 | Newton |
| D1,067,424 | S | 3/2025 | Naughton et al. |
| 12,245,966 | B2 | 3/2025 | Newton |
| 12,245,967 | B2 | 3/2025 | Mann |
| 12,257,173 | B2 | 3/2025 | Newton et al. |
| 12,274,638 | B2 | 4/2025 | Spector |
| D1,074,995 | S | 5/2025 | Laffay et al. |
| 12,324,765 | B2 | 6/2025 | Sanchez et al. |
| 12,324,767 | B2 | 6/2025 | Hughett et al. |
| 12,329,364 | B2 | 6/2025 | Austermann et al. |
| 12,350,190 | B2 | 7/2025 | Hughett, Sr. et al. |
| 12,419,778 | B2 | 9/2025 | Johannes et al. |
| 12,440,370 | B2 | 10/2025 | Davis et al. |
| 12,447,042 | B2 | 10/2025 | Martin et al. |
| 12,465,514 | B2 | 11/2025 | Fallows et al. |
| 12,465,515 | B2 | 11/2025 | Brooks |
| 12,478,499 | B2 | 11/2025 | Nguyen et al. |
| D1,104,255 | S | 12/2025 | Hanna et al. |
| D1,107,222 | S | 12/2025 | Ecklund et al. |
| 12,521,272 | B2 | 1/2026 | Davis |
| 12,551,366 | B2 | 2/2026 | Brennan et al. |
| 12,551,385 | B2 | 2/2026 | Jagannathan et al. |
| 12,569,364 | B2 | 3/2026 | Johannes et al. |
| 12,569,365 | B2 | 3/2026 | Meyer et al. |
| 12,575,961 | B2 | 3/2026 | Glithero |
| 12,589,022 | B2 | 3/2026 | Abdelal et al. |
| 12,594,062 | B2 | 4/2026 | Watson et al. |
| 12,594,182 | B2 | 4/2026 | Davis et al. |
| 12,622,803 | B2 | 5/2026 | Sweeney |
| 2001/0037097 | A1 | 11/2001 | Cheng et al. |
| 2001/0037098 | A1 | 11/2001 | Snyder |
| 2001/0054426 | A1 | 12/2001 | Knudson et al. |
| 2002/0019614 | A1 | 2/2002 | Woon |
| 2002/0026161 | A1 | 2/2002 | Grundke |
| 2002/0026163 | A1 | 2/2002 | Grundke |

(56) References Cited

U.S. PATENT DOCUMENTS

2002/0033200 A1 3/2002 Alex et al.
2002/0042945 A1 4/2002 Sands
2002/0058915 A1 5/2002 Wakabayashi
2002/0087131 A1 7/2002 Wolff et al.
2002/0091364 A1 7/2002 Prabhakar
2002/0189992 A1 12/2002 Schmidt et al.
2002/0193760 A1 12/2002 Thompson
2002/0193762 A1 12/2002 Suydam
2003/0004436 A1 1/2003 Schmidt et al.
2003/0018309 A1 1/2003 Breznock
2003/0032931 A1 2/2003 Grundke et al.
2003/0032944 A1 2/2003 Cawood
2003/0073964 A1 4/2003 Palumbo et al.
2003/0074724 A1 4/2003 Sands
2003/0097100 A1 5/2003 Watson
2003/0110868 A1 6/2003 Muller et al.
2003/0120178 A1 6/2003 Heki
2003/0129178 A1 7/2003 Wegman et al.
2003/0132352 A1 7/2003 Weaver
2003/0157859 A1 8/2003 Ishikawa
2003/0178360 A1 9/2003 Haldopoulos et al.
2003/0181880 A1 9/2003 Schwartz
2003/0195484 A1 10/2003 Harvie
2003/0204173 A1 10/2003 Burns et al.
2003/0222101 A1 12/2003 Chang
2003/0233079 A1 12/2003 Parks et al.
2004/0002687 A1 1/2004 Burns et al.
2004/0006321 A1 1/2004 Cheng et al.
2004/0015141 A1 1/2004 Cheng et al.
2004/0056122 A1 3/2004 Male et al.
2004/0084465 A1 5/2004 Luburic
2004/0098794 A1 5/2004 Ernest et al.
2004/0102753 A1 5/2004 Butler
2004/0127872 A1 7/2004 Petryk et al.
2004/0128749 A1 7/2004 Scott
2004/0143229 A1 7/2004 Easter
2004/0147863 A1 7/2004 Diaz et al.
2004/0147894 A1 7/2004 Mizutani et al.
2004/0147895 A1 7/2004 Mizutani et al.
2004/0158221 A1 8/2004 Mizutani et al.
2004/0176731 A1 9/2004 Cheng et al.
2004/0176746 A1 9/2004 Forral
2004/0181201 A1 9/2004 Mizutani et al.
2004/0187200 A1 9/2004 Otto et al.
2004/0191919 A1 9/2004 Unger et al.
2004/0194792 A1 10/2004 Zhuang et al.
2004/0200936 A1 10/2004 Opperthauser
2004/0207530 A1 10/2004 Nielsen
2004/0215133 A1 10/2004 Weber et al.
2004/0236292 A1 11/2004 Tazoe et al.
2004/0243075 A1 12/2004 Harvie
2004/0254547 A1 12/2004 Okabe et al.
2005/0010182 A1 1/2005 Parks et al.
2005/0010197 A1 1/2005 Lau et al.
2005/0033248 A1 2/2005 Machida et al.
2005/0065471 A1 3/2005 Kuntz
2005/0070861 A1 3/2005 Okabe et al.
2005/0070862 A1 3/2005 Tazoe et al.
2005/0082300 A1 4/2005 Modrell et al.
2005/0097662 A1 5/2005 Leimkuhler et al.
2005/0101924 A1 5/2005 Elson et al.
2005/0119630 A1 6/2005 Harvie
2005/0131361 A1 6/2005 Miskie
2005/0137557 A1 6/2005 Swiecicki et al.
2005/0137560 A1 6/2005 Mizutani et al.
2005/0137561 A1 6/2005 Mizutani et al.
2005/0148984 A1 7/2005 Lindsay et al.
2005/0154360 A1 7/2005 Harvie
2005/0177070 A1 8/2005 Levinson et al.
2005/0197639 A1 9/2005 Mombrinie
2005/0197645 A1 9/2005 Karpowicz et al.
2005/0215969 A1 9/2005 Mizutani et al.
2005/0273069 A1 12/2005 Mizutani et al.
2005/0273920 A1 12/2005 Marinas
2005/0277903 A1 12/2005 Mizutani et al.
2005/0277904 A1 12/2005 Chase et al.
2005/0279359 A1 12/2005 Leblanc et al.
2006/0004332 A1 1/2006 Marx
2006/0005307 A1 1/2006 Arguelles
2006/0015080 A1 1/2006 Mahnensmith
2006/0015081 A1 1/2006 Suzuki et al.
2006/0016778 A1 1/2006 Park
2006/0054384 A1 3/2006 Chen
2006/0069359 A1 3/2006 Dipalma et al.
2006/0079852 A1 4/2006 Bubb et al.
2006/0079854 A1 4/2006 Kay et al.
2006/0084932 A1 4/2006 Koizumi et al.
2006/0100596 A1 5/2006 Miskie
2006/0111648 A1 5/2006 Vermaak
2006/0113334 A1 6/2006 Mikhail et al.
2006/0155214 A1 7/2006 Wightman
2006/0166350 A1 7/2006 Lowe et al.
2006/0171997 A1 8/2006 Gruenbacher et al.
2006/0180566 A1 8/2006 Mataya
2006/0200102 A1 9/2006 Cooper
2006/0229575 A1 10/2006 Boiarski
2006/0229576 A1 10/2006 Conway et al.
2006/0231648 A1 10/2006 Male et al.
2006/0235266 A1 10/2006 Nan
2006/0235359 A1 10/2006 Marland
2006/0241553 A1 10/2006 Harvie
2006/0269439 A1 11/2006 White
2006/0277670 A1 12/2006 Baker et al.
2007/0006368 A1 1/2007 Key et al.
2007/0010797 A1 1/2007 Nishtala et al.
2007/0016152 A1 1/2007 Karpowicz et al.
2007/0025886 A1 2/2007 Yong
2007/0032765 A1 2/2007 Honda
2007/0038194 A1 2/2007 Wada et al.
2007/0055209 A1 3/2007 Patel et al.
2007/0073252 A1 3/2007 Forgrave
2007/0106177 A1 5/2007 Hama
2007/0117880 A1 5/2007 Elson et al.
2007/0118993 A1 5/2007 Bates
2007/0135786 A1 6/2007 Schmidt et al.
2007/0137718 A1 6/2007 Rushlander et al.
2007/0149935 A1 6/2007 Dirico
2007/0191804 A1 8/2007 Coley
2007/0203464 A1 8/2007 Green et al.
2007/0214553 A1 9/2007 Carromba et al.
2007/0225663 A1 9/2007 Watt et al.
2007/0225666 A1 9/2007 Otto
2007/0225668 A1 9/2007 Otto
2007/0266486 A1 11/2007 Ramirez
2007/0270716 A1 11/2007 Wu et al.
2007/0282309 A1 12/2007 Bengtson et al.
2008/0004576 A1 1/2008 Tanaka et al.
2008/0015526 A1 1/2008 Reiner et al.
2008/0015527 A1 1/2008 House
2008/0033386 A1 2/2008 Okabe et al.
2008/0041869 A1 2/2008 Backaert
2008/0077099 A1 3/2008 House
2008/0091153 A1 4/2008 Harvie
2008/0091158 A1 4/2008 Yang
2008/0091162 A1 4/2008 Maldonado et al.
2008/0114327 A1 5/2008 Barge
2008/0140033 A1 6/2008 Burgess et al.
2008/0167634 A1 7/2008 Kouta et al.
2008/0183157 A1 7/2008 Walters
2008/0200884 A1 8/2008 Perkins et al.
2008/0215031 A1 9/2008 Belfort et al.
2008/0234642 A1 9/2008 Patterson et al.
2008/0269703 A1 10/2008 Collins et al.
2008/0281282 A1 11/2008 Finger et al.
2008/0287894 A1 11/2008 Van Den Heuvel et al.
2008/0312550 A1 12/2008 Nishtala et al.
2009/0025717 A1 1/2009 Pinel
2009/0048570 A1 2/2009 Jensen
2009/0056003 A1 3/2009 Ivie et al.
2009/0069761 A1 3/2009 Vogel
2009/0069765 A1 3/2009 Wortham
2009/0120179 A1 5/2009 Nylander et al.
2009/0192482 A1 7/2009 Dodge et al.
2009/0199857 A1 8/2009 Peake et al.

(56) References Cited

U.S. PATENT DOCUMENTS

2009/0226541 A1 9/2009 Scholz et al.
2009/0234312 A1 9/2009 Otoole et al.
2009/0247968 A1 10/2009 Brooks et al.
2009/0251510 A1 10/2009 Noro et al.
2009/0254040 A1 10/2009 Bierman et al.
2009/0259206 A1 10/2009 Kai et al.
2009/0264840 A1 10/2009 Mrginio
2009/0270822 A1 10/2009 Medeiros
2009/0281510 A1 11/2009 Fisher
2009/0283982 A1 11/2009 Thomas
2009/0306610 A1 12/2009 Van Den Heuvel et al.
2010/0004612 A1 1/2010 Thevenin
2010/0030189 A1 2/2010 Fleming
2010/0031429 A1 2/2010 Kim et al.
2010/0032789 A1 2/2010 Schoen et al.
2010/0058660 A1 3/2010 Williams
2010/0121289 A1 5/2010 Parks et al.
2010/0158168 A1 6/2010 Murthy et al.
2010/0160882 A1 6/2010 Lowe
2010/0174250 A1 7/2010 Hu et al.
2010/0179493 A1 7/2010 Heagle et al.
2010/0185168 A1 7/2010 Graauw et al.
2010/0198172 A1 8/2010 Wada et al.
2010/0211032 A1 8/2010 Tsai et al.
2010/0234820 A1 9/2010 Tsai et al.
2010/0241104 A1 9/2010 Gilbert
2010/0263113 A1 10/2010 Shelton et al.
2010/0310845 A1 12/2010 Bond et al.
2011/0022011 A1 1/2011 Edward
2011/0028920 A1 2/2011 Johannison
2011/0028922 A1 2/2011 Kay et al.
2011/0034889 A1 2/2011 Smith
2011/0036837 A1 2/2011 Shang
2011/0040267 A1 2/2011 Wada et al.
2011/0040271 A1 2/2011 Rogers et al.
2011/0054426 A1 3/2011 Stewart et al.
2011/0060299 A1 3/2011 Wada et al.
2011/0060300 A1 3/2011 Weig et al.
2011/0077495 A1 3/2011 Gilbert
2011/0077606 A1 3/2011 Wilcox et al.
2011/0087337 A1 4/2011 Forsell
2011/0137273 A1 6/2011 Muellejans et al.
2011/0145993 A1 6/2011 Rader et al.
2011/0152802 A1 6/2011 Dicamillo et al.
2011/0152842 A1 6/2011 Graffam et al.
2011/0164147 A1 7/2011 Takahashi et al.
2011/0172620 A1 7/2011 Khambatta
2011/0172625 A1 7/2011 Wada et al.
2011/0198904 A1 8/2011 Thomas et al.
2011/0202024 A1 8/2011 Cozzens
2011/0238023 A1 9/2011 Slayton
2011/0240648 A1 10/2011 Tucker
2011/0251572 A1 10/2011 Nishtala et al.
2011/0265889 A1 11/2011 Tanaka et al.
2011/0276020 A1 11/2011 Mitsui
2011/0319804 A1 12/2011 Greener
2012/0004079 A1 1/2012 Hyacinth
2012/0029452 A1 2/2012 Roedsten
2012/0035577 A1 2/2012 Tomes et al.
2012/0041400 A1 2/2012 Christensen
2012/0059328 A1 3/2012 Dikeman et al.
2012/0066825 A1 3/2012 Birbara et al.
2012/0103347 A1 5/2012 Wheaton et al.
2012/0116336 A1 5/2012 Sharma et al.
2012/0137420 A1 6/2012 Gordon et al.
2012/0165768 A1 6/2012 Sekiyama et al.
2012/0165786 A1 6/2012 Chappa et al.
2012/0209216 A1 8/2012 Jensen et al.
2012/0209225 A1 8/2012 Hu et al.
2012/0210503 A1 8/2012 Anzivino et al.
2012/0215187 A1 8/2012 Tippet et al.
2012/0228055 A1 9/2012 Kato et al.
2012/0233761 A1 9/2012 Huang
2012/0245541 A1 9/2012 Suzuki et al.
2012/0245542 A1 9/2012 Suzuki et al.
2012/0245547 A1 9/2012 Wilcox et al.
2012/0253303 A1 10/2012 Suzuki et al.
2012/0271259 A1 10/2012 Ulert
2012/0296305 A1 11/2012 Barraza Khaled et al.
2012/0316522 A1 12/2012 Carter et al.
2012/0330256 A1 12/2012 Wilcox et al.
2013/0006206 A1 1/2013 Wada et al.
2013/0019374 A1 1/2013 Schwartz
2013/0036544 A1 2/2013 Lee et al.
2013/0045651 A1 2/2013 Esteves et al.
2013/0046258 A1 2/2013 Chambers
2013/0053804 A1 2/2013 Soerensen et al.
2013/0096523 A1 4/2013 Chang et al.
2013/0110059 A1 5/2013 Kossow et al.
2013/0138064 A1 5/2013 Stroebech et al.
2013/0144240 A1 6/2013 Ellis
2013/0150813 A1 6/2013 Gordon et al.
2013/0158494 A1 6/2013 Ong et al.
2013/0165880 A1 6/2013 Amos et al.
2013/0190706 A1 7/2013 Kleiner
2013/0211385 A1 8/2013 Lazarus
2013/0218112 A1 8/2013 Thompson
2013/0245496 A1 9/2013 Wells et al.
2013/0245586 A1 9/2013 Jha
2013/0253528 A1 9/2013 Haffner et al.
2013/0274711 A1 10/2013 O'Day
2013/0292537 A1 11/2013 Dirico
2013/0324954 A1 12/2013 Friedrich
2013/0330501 A1 12/2013 Aizenberg et al.
2014/0005647 A1 1/2014 Shuffler et al.
2014/0031774 A1 1/2014 Bengtson
2014/0039432 A1 2/2014 Dunbar et al.
2014/0039440 A1 2/2014 Doescher
2014/0058347 A1 2/2014 Marquette
2014/0107595 A1 4/2014 Blott et al.
2014/0107599 A1 4/2014 Fink et al.
2014/0157499 A1 6/2014 Suzuki et al.
2014/0171889 A1 6/2014 Hopman et al.
2014/0182051 A1 7/2014 Tanimoto et al.
2014/0196189 A1 7/2014 Lee et al.
2014/0216478 A1 8/2014 Park et al.
2014/0230831 A1 8/2014 Zaltsberg et al.
2014/0257231 A1 9/2014 Wang et al.
2014/0276501 A1 9/2014 Cisko
2014/0303582 A1 10/2014 Wright et al.
2014/0316381 A1 10/2014 Reglin
2014/0325746 A1 11/2014 Block
2014/0343516 A1 11/2014 Coulthard et al.
2014/0348139 A1 11/2014 Gomez Martinez
2014/0352050 A1 12/2014 Yao et al.
2014/0371628 A1 12/2014 Desai
2015/0000027 A1 1/2015 Hughes et al.
2015/0045757 A1 2/2015 Lee et al.
2015/0047114 A1 2/2015 Ramirez
2015/0048089 A1 2/2015 Robertson
2015/0135423 A1 5/2015 Sharpe et al.
2015/0157300 A1 6/2015 Ealovega et al.
2015/0209188 A1 7/2015 Scheremet et al.
2015/0209194 A1 7/2015 Heyman
2015/0216714 A1 8/2015 Sasaki et al.
2015/0238687 A1 8/2015 Novakovic et al.
2015/0267862 A1 9/2015 Mishler
2015/0290421 A1 10/2015 Glickman et al.
2015/0290425 A1 10/2015 Macy et al.
2015/0320583 A1 11/2015 Harvie
2015/0329255 A1 11/2015 Rzepecki
2015/0342799 A1 12/2015 Michiels et al.
2015/0359660 A1 12/2015 Harvie
2015/0359996 A1 12/2015 Arora et al.
2015/0366699 A1 12/2015 Nelson
2015/0374535 A1 12/2015 Davis et al.
2016/0008193 A1 1/2016 Schulke
2016/0029998 A1 2/2016 Brister et al.
2016/0030228 A1 2/2016 Jones
2016/0038356 A1 2/2016 Yao et al.
2016/0051395 A1 2/2016 Ugarte M.D.
2016/0058322 A1 3/2016 Brister et al.
2016/0060001 A1 3/2016 Wada et al.
2016/0100976 A1 4/2016 Conway et al.

(56) References Cited

U.S. PATENT DOCUMENTS

2016/0106604 A1 4/2016 Timm
2016/0113809 A1 4/2016 Kim
2016/0135792 A1 5/2016 Cai
2016/0136338 A1 5/2016 Lee et al.
2016/0183689 A1 6/2016 Miner
2016/0256022 A1 9/2016 Le
2016/0270982 A1 9/2016 Raycheck et al.
2016/0278662 A1 9/2016 Brister et al.
2016/0286008 A1 9/2016 Perez Martinez
2016/0327553 A1 11/2016 Edwards et al.
2016/0354268 A1 12/2016 Fennell
2016/0357400 A1 12/2016 Penha et al.
2016/0366699 A1 12/2016 Zhang et al.
2016/0367226 A1 12/2016 Newton et al.
2016/0367411 A1 12/2016 Justiz et al.
2016/0367726 A1 12/2016 Gratzer
2016/0374848 A1 12/2016 Sanchez et al.
2017/0007438 A1 1/2017 Harvie
2017/0014560 A1 1/2017 Minskoff et al.
2017/0028110 A1 2/2017 Smith et al.
2017/0042724 A1 2/2017 Ugarte
2017/0042748 A1 2/2017 Griffin
2017/0049605 A1 2/2017 Wisniewski
2017/0100276 A1 4/2017 Joh
2017/0107312 A1 4/2017 Hinayama et al.
2017/0128638 A1 5/2017 Giezendanner et al.
2017/0136209 A1 5/2017 Burnett et al.
2017/0143534 A1 5/2017 Sanchez
2017/0165100 A1 6/2017 Jackson et al.
2017/0165405 A1 6/2017 Muser et al.
2017/0189225 A1 7/2017 Voorhees et al.
2017/0202692 A1 7/2017 Laniado
2017/0216081 A1 8/2017 Accosta
2017/0238911 A1 8/2017 Duval
2017/0246026 A1 8/2017 Laniado
2017/0252014 A1 9/2017 Siller Gonzalez et al.
2017/0252202 A9 9/2017 Sanchez et al.
2017/0266031 A1 9/2017 Sanchez et al.
2017/0266658 A1 9/2017 Bruno et al.
2017/0281399 A1 10/2017 Vanmiddendorp et al.
2017/0281419 A1 10/2017 Pintado
2017/0312114 A1 11/2017 Glithero
2017/0312116 A1 11/2017 Laniado
2017/0312405 A1 11/2017 Newton
2017/0325788 A1 11/2017 Ealovega et al.
2017/0333244 A1 11/2017 Laniado
2017/0340489 A1 11/2017 Yamada
2017/0348139 A1 12/2017 Newton et al.
2017/0354532 A1* 12/2017 Holt ........................ A61F 5/453
2017/0354551 A1 12/2017 Gawley et al.
2017/0367873 A1 12/2017 Grannum
2018/0002075 A1 1/2018 Lee
2018/0008451 A1 1/2018 Stroebech
2018/0008804 A1 1/2018 Laniado
2018/0021218 A1 1/2018 Brosch et al.
2018/0028349 A1 2/2018 Newton et al.
2018/0037384 A1 2/2018 Archeny et al.
2018/0049910 A1 2/2018 Newton
2018/0064572 A1 3/2018 Wiltshire
2018/0104131 A1 4/2018 Killian
2018/0127187 A1 5/2018 Sewell
2018/0149635 A1 5/2018 Abir
2018/0169281 A1 6/2018 Russell et al.
2018/0193215 A1 7/2018 Davies et al.
2018/0200101 A1 7/2018 Su
2018/0214297 A1 8/2018 Hughett et al.
2018/0215649 A1 8/2018 Wada et al.
2018/0221216 A1 8/2018 Benz et al.
2018/0228642 A1 8/2018 Davis et al.
2018/0229014 A1 8/2018 Guirguis et al.
2018/0256384 A1 9/2018 Kasirye
2018/0271694 A1 9/2018 Fernandez et al.
2018/0280236 A1 10/2018 Ludin et al.
2018/0311069 A1 11/2018 Hjorth et al.
2018/0317892 A1 11/2018 Catlin
2018/0325748 A1 11/2018 Sharma et al.
2019/0001029 A1 1/2019 Davie et al.
2019/0001030 A1 1/2019 Braga et al.
2019/0021899 A1 1/2019 Vlet
2019/0029869 A1 1/2019 Huchthausen
2019/0038451 A1 2/2019 Harvie
2019/0046102 A1 2/2019 Kushnir et al.
2019/0059938 A1 2/2019 Holsten
2019/0060138 A1 2/2019 Marquez et al.
2019/0091059 A1 3/2019 Gabriel
2019/0100362 A1 4/2019 Meyers et al.
2019/0133126 A1 5/2019 Modak et al.
2019/0133814 A1 5/2019 Tammen et al.
2019/0142624 A1 5/2019 Sanchez et al.
2019/0224036 A1 7/2019 Sanchez et al.
2019/0226189 A1 7/2019 Braxton
2019/0240079 A1 8/2019 Tuli
2019/0247222 A1 8/2019 Ecklund et al.
2019/0247223 A1 8/2019 Brun et al.
2019/0247623 A1 8/2019 Helm et al.
2019/0282391 A1 9/2019 Johannes et al.
2019/0314189 A1 10/2019 Acosta
2019/0314190 A1 10/2019 Sanchez et al.
2019/0321587 A1 10/2019 Mcmenamin et al.
2019/0344934 A1 11/2019 Faerber et al.
2019/0350746 A1 11/2019 Trachsel
2019/0358108 A1 11/2019 Cocks et al.
2019/0358372 A1 11/2019 Askem et al.
2019/0365303 A1 12/2019 Bullington et al.
2019/0365307 A1 12/2019 Laing et al.
2019/0365561 A1 12/2019 Newton et al.
2019/0374373 A1 12/2019 Joh
2020/0008985 A1 1/2020 Nguyen et al.
2020/0016012 A1 1/2020 Dutkiewicz
2020/0030595 A1 1/2020 Boukidjian et al.
2020/0040561 A1 2/2020 Sugawara
2020/0046544 A1 2/2020 Godinez et al.
2020/0055638 A1 2/2020 Lau et al.
2020/0070392 A1 3/2020 Huber et al.
2020/0085609 A1 3/2020 Schelch et al.
2020/0085610 A1 3/2020 Cohn et al.
2020/0086090 A1 3/2020 Von Weymarn-schärli et al.
2020/0107518 A1 4/2020 Hiroshima et al.
2020/0129322 A1 4/2020 Leuckel
2020/0171217 A9 6/2020 Braga et al.
2020/0179177 A1 6/2020 Erdem et al.
2020/0187918 A1 6/2020 Wiygul
2020/0206015 A1 7/2020 Langer
2020/0206039 A1 7/2020 Mclain
2020/0214910 A1 7/2020 Varona et al.
2020/0216898 A1 7/2020 Hubbell
2020/0216989 A1 7/2020 Kinugasa et al.
2020/0229964 A1 7/2020 Staali et al.
2020/0231343 A1 7/2020 Freedman et al.
2020/0232841 A1 7/2020 Satish et al.
2020/0246172 A1 8/2020 Ho
2020/0246203 A1 8/2020 Tulk et al.
2020/0255189 A1 8/2020 Liu
2020/0261280 A1 8/2020 Heyman
2020/0276046 A1 9/2020 Staali et al.
2020/0306075 A1 10/2020 Newton et al.
2020/0315837 A1 10/2020 Radl et al.
2020/0315838 A1 10/2020 Eckert
2020/0315872 A1 10/2020 Viens et al.
2020/0315874 A1 10/2020 Viens et al.
2020/0331672 A1 10/2020 Bertram et al.
2020/0345332 A1 11/2020 Duval
2020/0352774 A1 11/2020 Rabinowitz et al.
2020/0353135 A1 11/2020 Gregory et al.
2020/0367677 A1 11/2020 Silsby et al.
2020/0369444 A1 11/2020 Silsby et al.
2020/0375781 A1 12/2020 Staali et al.
2020/0375810 A1 12/2020 Carlin et al.
2020/0384242 A1 12/2020 Havard et al.
2020/0385179 A1 12/2020 McCourt
2020/0390591 A1 12/2020 Glithero et al.
2020/0390592 A1 12/2020 Merrill
2020/0398024 A1 12/2020 Fletter et al.
2020/0405521 A1 12/2020 Glasroe

(56) References Cited

U.S. PATENT DOCUMENTS

2020/0405523 A1 12/2020 Obst et al.
2021/0007910 A1 1/2021 Furukawa
2021/0008771 A1 1/2021 Huber et al.
2021/0009323 A1 1/2021 Markarian et al.
2021/0020072 A1 1/2021 Moehring et al.
2021/0023279 A1 1/2021 Radl et al.
2021/0059853 A1 3/2021 Davis et al.
2021/0061523 A1 3/2021 Bytheway
2021/0069005 A1 3/2021 Sanchez et al.
2021/0069008 A1 3/2021 Blabas et al.
2021/0069009 A1 3/2021 Im
2021/0069030 A1 3/2021 Nishikawa et al.
2021/0077993 A1 3/2021 Nazareth et al.
2021/0113749 A1 4/2021 Radl et al.
2021/0121318 A1 4/2021 Pinlac
2021/0137724 A1 5/2021 Ecklund et al.
2021/0138190 A1 5/2021 Erbey et al.
2021/0154055 A1 5/2021 Mllarreal
2021/0170079 A1 6/2021 Radl et al.
2021/0178390 A1 6/2021 Oueslati et al.
2021/0186742 A1 6/2021 Newton et al.
2021/0186744 A1 6/2021 Spector
2021/0206144 A1 7/2021 Ewell
2021/0211568 A1 7/2021 Zhou et al.
2021/0212865 A1 7/2021 Wallajapet et al.
2021/0220162 A1 7/2021 Jamison
2021/0220163 A1 7/2021 Mayrand
2021/0228400 A1 7/2021 Glithero
2021/0228401 A1 7/2021 Becker et al.
2021/0228795 A1 7/2021 Hughett et al.
2021/0229877 A1 7/2021 Ragias et al.
2021/0236323 A1 8/2021 Austermann et al.
2021/0236324 A1 8/2021 Sweeney
2021/0251814 A1 8/2021 Jönegren et al.
2021/0267787 A1 9/2021 Nazemi
2021/0275343 A1 9/2021 Sanchez et al.
2021/0275344 A1 9/2021 Wing
2021/0290454 A1 9/2021 Yamada
2021/0290464 A1 9/2021 Furuta
2021/0315726 A1 10/2021 Lin
2021/0315727 A1 10/2021 Jiang
2021/0353449 A1 11/2021 Sharma et al.
2021/0353450 A1 11/2021 Sharma et al.
2021/0361469 A1 11/2021 Liu et al.
2021/0369495 A1 12/2021 Cheng et al.
2021/0386925 A1 12/2021 Hartwell et al.
2021/0393433 A1 12/2021 Godinez et al.
2022/0015958 A1 1/2022 Ito
2022/0023091 A1 1/2022 Ecklund et al.
2022/0026546 A1 1/2022 Aono et al.
2022/0031290 A1 2/2022 Weed
2022/0031523 A1 2/2022 Pierpoint
2022/0039995 A1 2/2022 Johannes et al.
2022/0047410 A1 2/2022 Walthall
2022/0062025 A1 3/2022 Shields et al.
2022/0062027 A1 3/2022 Mitchell et al.
2022/0062028 A1 3/2022 Mitchell et al.
2022/0062029 A1 3/2022 Johannes et al.
2022/0066825 A1 3/2022 Saraf et al.
2022/0071811 A1 3/2022 Cheng et al.
2022/0071826 A1 3/2022 Kulkarni et al.
2022/0104965 A1 4/2022 Vaninetti et al.
2022/0104976 A1 4/2022 Hoeger et al.
2022/0104981 A1 4/2022 Jones
2022/0117773 A1 4/2022 Davis et al.
2022/0117774 A1 4/2022 Meyer et al.
2022/0117775 A1 4/2022 Jones et al.
2022/0118165 A1 4/2022 Knapp et al.
2022/0133524 A1 5/2022 Davis
2022/0151817 A1 5/2022 Mann
2022/0160949 A1 5/2022 Simiele et al.
2022/0168159 A1 6/2022 Triado et al.
2022/0193312 A1 6/2022 Lee et al.
2022/0211536 A1 7/2022 Johannes et al.
2022/0218510 A1 7/2022 Metzger et al.
2022/0229053 A1 7/2022 Levin et al.
2022/0241106 A1 8/2022 Johannes et al.
2022/0241115 A1 8/2022 Lang et al.
2022/0247407 A1 8/2022 Yamamoto et al.
2022/0248836 A1 8/2022 Cagle et al.
2022/0257407 A1 8/2022 Johannes et al.
2022/0265460 A1 8/2022 Coker
2022/0265461 A1 8/2022 Kharkar et al.
2022/0265462 A1 8/2022 Alder et al.
2022/0270711 A1 8/2022 Feala et al.
2022/0273482 A1 9/2022 Johannes et al.
2022/0280357 A1 9/2022 Jagannathan et al.
2022/0280710 A1 9/2022 Agrawal et al.
2022/0287689 A1 9/2022 Johannes
2022/0287691 A1 9/2022 Wormser et al.
2022/0287867 A1 9/2022 Jones et al.
2022/0287868 A1 9/2022 Garvey et al.
2022/0296406 A1 9/2022 Keelen
2022/0296408 A1 9/2022 Evans et al.
2022/0305191 A1 9/2022 Joseph et al.
2022/0313222 A1 10/2022 Austermann et al.
2022/0313474 A1 10/2022 Kriscovich et al.
2022/0331170 A1 10/2022 Erdem et al.
2022/0339023 A1 10/2022 Davis et al.
2022/0339024 A1 10/2022 Johannes et al.
2022/0354685 A1 11/2022 Davis et al.
2022/0362049 A1 11/2022 Austermann et al.
2022/0370231 A1 11/2022 Wang et al.
2022/0370234 A1 11/2022 Hughett et al.
2022/0370235 A1 11/2022 Johannes et al.
2022/0370237 A1 11/2022 Parmar et al.
2022/0387001 A1 12/2022 Askenazi et al.
2022/0387693 A1 12/2022 Bannwart et al.
2022/0395390 A1 12/2022 Brooks
2022/0395391 A1 12/2022 Saunders et al.
2022/0401252 A1 12/2022 Warren
2022/0409419 A1 12/2022 Garvey et al.
2022/0409422 A1 12/2022 Schneider et al.
2023/0018845 A1 1/2023 Lee
2023/0020563 A1 1/2023 Sharma et al.
2023/0031640 A1 2/2023 Hughett et al.
2023/0037159 A1 2/2023 Brennan et al.
2023/0049924 A1 2/2023 Johannes et al.
2023/0052238 A1 2/2023 Oluwasogo
2023/0062994 A1 3/2023 Ecklund et al.
2023/0070347 A1 3/2023 Watson et al.
2023/0073708 A1 3/2023 Xu et al.
2023/0089032 A1 3/2023 Hughett et al.
2023/0091118 A1 3/2023 Watson
2023/0099821 A1 3/2023 Radl et al.
2023/0099991 A1 3/2023 Bianchi et al.
2023/0105001 A1 4/2023 Whittome et al.
2023/0110577 A1 4/2023 Choi
2023/0138269 A1 5/2023 Abdelal et al.
2023/0145365 A1 5/2023 Martin et al.
2023/0155253 A1 5/2023 Yin et al.
2023/0190511 A1 6/2023 Sharma et al.
2023/0210504 A1 7/2023 Kuroda et al.
2023/0210685 A1 7/2023 Fallows et al.
2023/0218426 A1 7/2023 Hughett
2023/0240884 A1 8/2023 Davis et al.
2023/0248562 A1 8/2023 Sanchez et al.
2023/0248564 A1 8/2023 Mann et al.
2023/0255812 A1 8/2023 Sanchez et al.
2023/0255813 A1 8/2023 Sanchez et al.
2023/0255815 A1 8/2023 Newton
2023/0263650 A1 8/2023 Sanchez et al.
2023/0263655 A1 8/2023 Johannes et al.
2023/0277360 A1 9/2023 Lambert et al.
2023/0277362 A1 9/2023 Davis et al.
2023/0285178 A1 9/2023 Sanchez et al.
2023/0293339 A1 9/2023 James
2023/0301846 A1 9/2023 Greenwood
2023/0355423 A1 11/2023 Stevenson et al.
2023/0389900 A1 12/2023 Xie et al.
2023/0404791 A1 12/2023 Ecklund et al.
2024/0000617 A1 1/2024 Locke
2024/0008444 A1 1/2024 Su et al.
2024/0009023 A1 1/2024 Johannes et al.

(56) References Cited

U.S. PATENT DOCUMENTS

| | | | |
|---|---|---|---|
| 2024/0024170 | A1 | 1/2024 | Scott |
| 2024/0033148 | A1 | 2/2024 | Gordon et al. |
| 2024/0041638 | A1 | 2/2024 | Johannes et al. |
| 2024/0058157 | A1 | 2/2024 | Davis |
| 2024/0058160 | A1 | 2/2024 | Young Joyner et al. |
| 2024/0058161 | A1 | 2/2024 | Ulreich et al. |
| 2024/0058520 | A1 | 2/2024 | Mn et al. |
| 2024/0065881 | A1 | 2/2024 | Kuroda et al. |
| 2024/0082044 | A1 | 3/2024 | Nguyen et al. |
| 2024/0099874 | A1 | 3/2024 | Sanchez et al. |
| 2024/0108268 | A1 | 4/2024 | Woodard et al. |
| 2024/0110318 | A1 | 4/2024 | Bendt et al. |
| 2024/0122773 | A1 | 4/2024 | Nguyen et al. |
| 2024/0123134 | A1 | 4/2024 | Kharkar et al. |
| 2024/0130885 | A1 | 4/2024 | Young Joyner et al. |
| 2024/0148539 | A1 | 5/2024 | Austermann et al. |
| 2024/0156633 | A1 | 5/2024 | Fallows et al. |
| 2024/0164935 | A1 | 5/2024 | Newton |
| 2024/0164937 | A1 | 5/2024 | Gloeckner et al. |
| 2024/0180737 | A1 | 6/2024 | Newton |
| 2024/0252343 | A1 | 8/2024 | Voda |
| 2024/0261131 | A1 | 8/2024 | Garvey et al. |
| 2024/0268986 | A1 | 8/2024 | Barnes et al. |
| 2024/0268989 | A1 | 8/2024 | Martin et al. |
| 2024/0268991 | A1 | 8/2024 | Davis |
| 2024/0269027 | A1 | 8/2024 | Tourchak et al. |
| 2024/0285425 | A1 | 8/2024 | Donohoe et al. |
| 2024/0325190 | A1 | 10/2024 | Minchew et al. |
| 2024/0335599 | A1 | 10/2024 | Cheng et al. |
| 2024/0341998 | A1 | 10/2024 | Julian et al. |
| 2024/0358539 | A1 | 10/2024 | Gallup |
| 2024/0358542 | A1 | 10/2024 | Richardson et al. |
| 2024/0374414 | A1 | 11/2024 | Richardson et al. |
| 2025/0009552 | A1 | 1/2025 | Blabas et al. |
| 2025/0017761 | A1 | 1/2025 | Lee |
| 2025/0073055 | A1 | 3/2025 | Ecklund et al. |
| 2025/0107920 | A1 | 4/2025 | Fallows et al. |
| 2025/0107921 | A1 | 4/2025 | Sanchez et al. |
| 2025/0367358 | A1 | 12/2025 | Smith et al. |
| 2026/0020972 | A1 | 1/2026 | Godinez et al. |

FOREIGN PATENT DOCUMENTS

| | | | |
|---|---|---|---|
| AU | 2022349367 | A1 | 4/2024 |
| CA | 2165286 | C | 9/1999 |
| CA | 2335223 | A1 | 1/2000 |
| CA | 2354132 | A1 | 6/2000 |
| CA | 2359091 | C | 9/2003 |
| CA | 2488867 | C | 8/2007 |
| CA | 3031934 | A1 | 2/2018 |
| CA | 3050918 | A1 | 8/2018 |
| CA | 3098571 | A1 | 11/2019 |
| CA | 3144181 | A1 | 1/2021 |
| CA | 3188651 | A1 | 7/2023 |
| CN | 2269203 | Y | 12/1997 |
| CN | 1332620 | A | 1/2002 |
| CN | 1434693 | A | 8/2003 |
| CN | 2569779 | Y | 9/2003 |
| CN | 1533755 | A | 10/2004 |
| CN | 1579348 | A | 2/2005 |
| CN | 1602825 | A | 4/2005 |
| CN | 1638708 | A | 7/2005 |
| CN | 1720888 | A | 1/2006 |
| CN | 2936204 | Y | 8/2007 |
| CN | 101262836 | A | 9/2008 |
| CN | 101522148 | A | 9/2009 |
| CN | 102159159 | A | 8/2011 |
| CN | 202184840 | U | 4/2012 |
| CN | 102481441 | A | 5/2012 |
| CN | 202463712 | U | 10/2012 |
| CN | 202950810 | U | 5/2013 |
| CN | 103533968 | A | 1/2014 |
| CN | 103717180 | A | 4/2014 |
| CN | 204562697 | U | 8/2015 |
| CN | 105411783 | A | 3/2016 |
| CN | 105451607 | A | 3/2016 |
| CN | 105451693 | A | 3/2016 |
| CN | 105534632 | A | 5/2016 |
| CN | 105616072 | A | 6/2016 |
| CN | 106132360 | A | 11/2016 |
| CN | 106137631 | A | 11/2016 |
| CN | 205849719 | U | 1/2017 |
| CN | 205924282 | U | 2/2017 |
| CN | 106726089 | A | 5/2017 |
| CN | 107847384 | A | 3/2018 |
| CN | 107920912 | A | 4/2018 |
| CN | 108420590 | A | 8/2018 |
| CN | 207785556 | U | 8/2018 |
| CN | 110171118 | A | 8/2019 |
| CN | 209285902 | U | 8/2019 |
| CN | 110381883 | A | 10/2019 |
| CN | 111465375 | A | 7/2020 |
| CN | 211198839 | U | 8/2020 |
| CN | 111991136 | A | 11/2020 |
| CN | 112022488 | A | 12/2020 |
| CN | 212234893 | U | 12/2020 |
| CN | 112384178 | A | 2/2021 |
| CN | 212466312 | U | 2/2021 |
| CN | 112566550 | A | 3/2021 |
| CN | 112603184 | A | 4/2021 |
| CN | 213490035 | U | 6/2021 |
| CN | 114007493 | A | 2/2022 |
| CN | 114375187 | A | 4/2022 |
| CN | 116096332 | A | 5/2023 |
| DE | 79818 | C | 10/1893 |
| DE | 1516466 | A1 | 6/1969 |
| DE | 2721330 | A1 | 11/1977 |
| DE | 2742298 | A1 | 3/1978 |
| DE | 3104356 | A1 | 9/1982 |
| DE | 9407554.9 | U1 | 5/1995 |
| DE | 4443710 | A1 | 6/1995 |
| DE | 4416094 | A1 | 11/1995 |
| DE | 4236097 | C2 | 10/1996 |
| DE | 19619597 | A1 | 11/1997 |
| DE | 202005013173 | U1 | 6/2006 |
| DE | 102005037762 | B3 | 9/2006 |
| DE | 202006018506 | U1 | 3/2007 |
| DE | 102011103783 | A1 | 12/2012 |
| DE | 102012112818 | A1 | 6/2014 |
| DE | 202015104597 | U1 | 7/2016 |
| DE | 102018118570 | A1 | 2/2020 |
| DE | 102020121462 | B3 | 1/2022 |
| DK | 9600118 | | 11/1996 |
| EP | 0032138 | A2 | 7/1981 |
| EP | 0066070 | B1 | 12/1982 |
| EP | 0068712 | A1 | 1/1983 |
| EP | 0140470 | A1 | 5/1985 |
| EP | 0220962 | A1 | 5/1987 |
| EP | 0140471 | B1 | 5/1988 |
| EP | 0274753 | A2 | 7/1988 |
| EP | 0119143 | B1 | 11/1988 |
| EP | 0483592 | A1 | 5/1992 |
| EP | 0483730 | A1 | 5/1992 |
| EP | 0610638 | A1 | 8/1994 |
| EP | 0613355 | A1 | 9/1994 |
| EP | 0711536 | A1 | 5/1996 |
| EP | 0613355 | B1 | 1/1997 |
| EP | 0680296 | B1 | 5/1997 |
| EP | 0787472 | A1 | 8/1997 |
| EP | 0945231 | A2 | 9/1999 |
| EP | 0966936 | A1 | 12/1999 |
| EP | 0987293 | A1 | 3/2000 |
| EP | 1063953 | A1 | 1/2001 |
| EP | 0653928 | B1 | 10/2002 |
| EP | 1332738 | A1 | 8/2003 |
| EP | 1382318 | A1 | 1/2004 |
| EP | 1089684 | B1 | 10/2004 |
| EP | 1616542 | A1 | 1/2006 |
| EP | 1382318 | B1 | 5/2006 |
| EP | 1063953 | B1 | 1/2007 |
| EP | 1658831 | B1 | 1/2008 |
| EP | 1872752 | A1 | 1/2008 |
| EP | 2180907 | A1 | 5/2010 |
| EP | 2380532 | A1 | 10/2011 |

(56) References Cited

FOREIGN PATENT DOCUMENTS

| | | | |
|---|---|---|---|
| EP | 2389908 | A1 | 11/2011 |
| EP | 2601916 | A1 | 6/2013 |
| EP | 2676643 | A1 | 12/2013 |
| EP | 2470251 | B1 | 12/2014 |
| EP | 2997950 | A2 | 3/2016 |
| EP | 2879534 | B1 | 3/2017 |
| EP | 3424471 | A1 | 1/2019 |
| EP | 3169292 | B1 | 11/2019 |
| EP | 3753492 | A1 | 12/2020 |
| EP | 3777801 | A1 | 2/2021 |
| EP | 3788992 | A1 | 3/2021 |
| EP | 3576689 | B1 | 3/2022 |
| EP | 3752110 | B1 | 3/2022 |
| EP | 3787570 | B1 | 3/2022 |
| EP | 4025163 | A1 | 7/2022 |
| EP | 3463180 | B1 | 3/2023 |
| EP | 3749230 | B1 | 3/2023 |
| EP | 3569205 | B1 | 6/2023 |
| EP | 4192402 | A1 | 6/2023 |
| EP | 4218702 | A1 | 8/2023 |
| EP | 3624742 | B1 | 1/2024 |
| EP | 4382082 | A2 | 6/2024 |
| EP | 4445881 | A2 | 10/2024 |
| EP | 4464288 | A2 | 11/2024 |
| EP | 4215134 | B1 | 1/2025 |
| EP | 4494611 | A2 | 1/2025 |
| EP | 4527361 | A2 | 3/2025 |
| EP | 4294336 | B1 | 9/2025 |
| FR | 2294812 | A1 | 7/1976 |
| FR | 2826704 | A1 | 1/2003 |
| GB | 871820 | A | 7/1961 |
| GB | 0873045 | A | 7/1961 |
| GB | 996370 | A | 6/1965 |
| GB | 1011517 | A | 12/1965 |
| GB | 1467144 | A | 3/1977 |
| GB | 2106395 | A | 4/1983 |
| GB | 2106784 | A | 4/1983 |
| GB | 2148126 | A | 5/1985 |
| GB | 2171315 | A | 8/1986 |
| GB | 2181953 | A | 5/1987 |
| GB | 2148126 | B | 7/1987 |
| GB | 2191095 | A | 12/1987 |
| GB | 2199750 | A | 7/1988 |
| GB | 2260907 | A | 5/1993 |
| GB | 2415386 | A | 12/2005 |
| GB | 2462267 | A | 2/2010 |
| GB | 2469496 | A | 10/2010 |
| GB | 2490327 | A | 10/2012 |
| GB | 2507318 | A | 4/2014 |
| GB | 2612752 | A | 5/2023 |
| IT | 201800009129 | A1 | 4/2020 |
| JP | S498638 | U | 1/1974 |
| JP | S5410596 | A | 1/1979 |
| JP | S5410596 | Y2 | 5/1979 |
| JP | S54155729 | U | 10/1979 |
| JP | S55155618 | A | 12/1980 |
| JP | S56152629 | U | 11/1981 |
| JP | S57142534 | U | 9/1982 |
| JP | S5888596 | U | 6/1983 |
| JP | S58130026 | A | 8/1983 |
| JP | S58188016 | U | 12/1983 |
| JP | S59118161 | A | 7/1984 |
| JP | S61502100 | A | 9/1986 |
| JP | S63107780 | U | 7/1988 |
| JP | H0267530 | A | 3/1990 |
| JP | H02103871 | A | 4/1990 |
| JP | H02131422 | A | 5/1990 |
| JP | H02131422 | U | 11/1990 |
| JP | H0460220 | A | 2/1992 |
| JP | H0515928 | U | 3/1993 |
| JP | H05123349 | A | 5/1993 |
| JP | H05123350 | A | 5/1993 |
| JP | H0625981 | U | 4/1994 |
| JP | H0626264 | U | 4/1994 |
| JP | 3087938 | B2 | 10/1995 |
| JP | H085630 | A | 1/1996 |
| JP | H08117271 | A | 5/1996 |
| JP | H08510924 | A | 11/1996 |
| JP | 2686634 | B2 | 12/1997 |
| JP | H1038669 | A | 2/1998 |
| JP | H1040141 | A | 2/1998 |
| JP | H10225430 | A | 8/1998 |
| JP | H11113946 | A | 4/1999 |
| JP | H11290365 | A | 10/1999 |
| JP | 2000116690 | A | 4/2000 |
| JP | 2000152953 | A | 6/2000 |
| JP | 2000185068 | A | 7/2000 |
| JP | 2000225139 | A | 8/2000 |
| JP | 2001054531 | A | 2/2001 |
| JP | 2001070331 | A | 3/2001 |
| JP | 2001224616 | A | 8/2001 |
| JP | 2001276107 | A | 10/2001 |
| JP | 2001276108 | A | 10/2001 |
| JP | 2002028173 | A | 1/2002 |
| JP | 2002502667 | A | 1/2002 |
| JP | 2002102285 | A | 4/2002 |
| JP | 2003038563 | A | 2/2003 |
| JP | 2003505152 | A | 2/2003 |
| JP | 2003126242 | A | 5/2003 |
| JP | 2003180722 | A | 7/2003 |
| JP | 2003227004 | A | 8/2003 |
| JP | 2003528691 | A | 9/2003 |
| JP | 2004057578 | A | 2/2004 |
| JP | 2004130056 | A | 4/2004 |
| JP | 2004267400 | A | 9/2004 |
| JP | 2004267530 | A | 9/2004 |
| JP | 2005052219 | A | 3/2005 |
| JP | 2005066011 | A | 3/2005 |
| JP | 2005066325 | A | 3/2005 |
| JP | 2005102978 | A | 4/2005 |
| JP | 2005518237 | A | 6/2005 |
| JP | 2005518901 | A | 6/2005 |
| JP | 2005323842 | A | 11/2005 |
| JP | 3749097 | B2 | 12/2005 |
| JP | 2006026108 | A | 2/2006 |
| JP | 3123547 | B2 | 6/2006 |
| JP | 2006136491 | A | 6/2006 |
| JP | 2006136492 | A | 6/2006 |
| JP | 2006204868 | A | 8/2006 |
| JP | 2007044494 | A | 2/2007 |
| JP | 3132659 | B2 | 5/2007 |
| JP | 2007209687 | A | 8/2007 |
| JP | 2007259898 | A | 10/2007 |
| JP | 4039641 | B2 | 11/2007 |
| JP | 2008005975 | A | 1/2008 |
| JP | 2008278928 | A | 11/2008 |
| JP | 2009500111 | A | 1/2009 |
| JP | 2009509570 | A | 3/2009 |
| JP | 2009165887 | A | 7/2009 |
| JP | 2009525776 | A | 7/2009 |
| JP | 2010504150 | A | 2/2010 |
| JP | 2010058795 | A | 3/2010 |
| JP | 2010081981 | A | 4/2010 |
| JP | 2010166954 | A | 8/2010 |
| JP | 4640772 | B2 | 12/2010 |
| JP | 2010536439 | A | 12/2010 |
| JP | 2011500225 | A | 1/2011 |
| JP | 2011030962 | A | 2/2011 |
| JP | 4747166 | B2 | 5/2011 |
| JP | 2011087823 | A | 5/2011 |
| JP | 4801218 | B1 | 8/2011 |
| JP | 2011522584 | A | 8/2011 |
| JP | 2011202664 | A | 10/2011 |
| JP | 2011218130 | A | 11/2011 |
| JP | 2011224070 | A | 11/2011 |
| JP | 3175719 | U | 4/2012 |
| JP | 2012522014 | A | 9/2012 |
| JP | 2012523869 | A | 10/2012 |
| JP | 2013238608 | A | 11/2013 |
| JP | 2014521960 | A | 8/2014 |
| JP | 2015092945 | A | 5/2015 |
| JP | 2015513678 | A | 5/2015 |
| JP | 3198994 | B2 | 7/2015 |
| JP | 2015221390 | A | 12/2015 |

(56) References Cited

FOREIGN PATENT DOCUMENTS

| | | | |
|---|---|---|---|
| JP | 2016521191 | A | 7/2016 |
| JP | 2017014698 | A | 1/2017 |
| JP | 3208707 | U | 2/2017 |
| JP | 3209321 | U | 3/2017 |
| JP | 2017070400 | A | 4/2017 |
| JP | 2017512603 | A | 5/2017 |
| JP | 2017127596 | A | 7/2017 |
| JP | 2017201272 | A | 11/2017 |
| JP | 2019010375 | A | 1/2019 |
| JP | 2019076342 | A | 5/2019 |
| JP | 2019525811 | A | 9/2019 |
| JP | 2019170942 | A | 10/2019 |
| JP | 2019533492 | A | 11/2019 |
| JP | 2020510464 | A | 4/2020 |
| JP | 2020520775 | A | 7/2020 |
| JP | 2020124425 | A | 8/2020 |
| JP | 2021007472 | A | 1/2021 |
| JP | 2021041145 | A | 3/2021 |
| JP | 2021074491 | A | 5/2021 |
| JP | 2021120686 | A | 8/2021 |
| JP | 2021519706 | A | 8/2021 |
| JP | 2021520952 | A | 8/2021 |
| JP | 2021522009 | A | 8/2021 |
| JP | 2021522013 | A | 8/2021 |
| JP | 2021522019 | A | 8/2021 |
| JP | 7129493 | B2 | 8/2022 |
| JP | 2022536986 | A | 8/2022 |
| JP | 2022540178 | A | 9/2022 |
| JP | 2022554252 | A | 12/2022 |
| JP | 2023532132 | A | 7/2023 |
| KR | 200290061 | Y1 | 9/2002 |
| KR | 20030047451 | A | 6/2003 |
| KR | 20080005516 | A | 1/2008 |
| KR | 20090072069 | A | 7/2009 |
| KR | 20090104426 | A | 10/2009 |
| KR | 20090110359 | A | 10/2009 |
| KR | 20100137210 | A | 12/2010 |
| KR | 101035745 | B1 | 5/2011 |
| KR | 20120005922 | A | 1/2012 |
| KR | 20140039485 | A | 4/2014 |
| KR | 101432639 | B1 | 8/2014 |
| KR | 20180022173 | A | 3/2018 |
| KR | 200486827 | Y1 | 7/2018 |
| KR | 20180106659 | A | 10/2018 |
| KR | 20180108774 | A | 10/2018 |
| KR | 101976679 | B1 | 5/2019 |
| KR | 101998130 | B1 | 7/2019 |
| KR | 20230034343 | A | 3/2023 |
| PT | 2068717 | E | 6/2013 |
| SE | 505542 | C2 | 9/1997 |
| TW | 408207 | B | 10/2000 |
| TW | 202123903 | A | 7/2021 |
| WO | 8101957 | A1 | 7/1981 |
| WO | 8804558 | A1 | 6/1988 |
| WO | 9104714 | A2 | 4/1991 |
| WO | 9104714 | A3 | 6/1991 |
| WO | 9220299 | A3 | 2/1993 |
| WO | 9303690 | A1 | 3/1993 |
| WO | 9307839 | A1 | 4/1993 |
| WO | 9309736 | A2 | 5/1993 |
| WO | 9309736 | A3 | 6/1993 |
| WO | 9416914 | A1 | 8/1994 |
| WO | 9514448 | A2 | 6/1995 |
| WO | 9600096 | A1 | 1/1996 |
| WO | 9634636 | A1 | 11/1996 |
| WO | 9817211 | A1 | 4/1998 |
| WO | 9830336 | A1 | 7/1998 |
| WO | 0000112 | A1 | 1/2000 |
| WO | 0000113 | A1 | 1/2000 |
| WO | 0025651 | A1 | 5/2000 |
| WO | 0033773 | A1 | 6/2000 |
| WO | 0057784 | A1 | 10/2000 |
| WO | 0069377 | A1 | 11/2000 |
| WO | 0079497 | A1 | 12/2000 |
| WO | 0145618 | A1 | 6/2001 |
| WO | 0145621 | A1 | 6/2001 |
| WO | 02094160 | A1 | 11/2002 |
| WO | 03013967 | A1 | 2/2003 |
| WO | 03015671 | A1 | 2/2003 |
| WO | 03024824 | A1 | 3/2003 |
| WO | 03055423 | A1 | 7/2003 |
| WO | 03071931 | A2 | 9/2003 |
| WO | 03079942 | A1 | 10/2003 |
| WO | 03071931 | A3 | 2/2004 |
| WO | 2004019836 | A1 | 3/2004 |
| WO | 2004024046 | A1 | 3/2004 |
| WO | 2004026195 | A1 | 4/2004 |
| WO | 2005003725 | A2 | 1/2005 |
| WO | 2005051252 | A1 | 6/2005 |
| WO | 2005060558 | A2 | 7/2005 |
| WO | 2005074571 | A3 | 9/2005 |
| WO | 2005089687 | A2 | 9/2005 |
| WO | 2005107661 | A2 | 11/2005 |
| WO | 2006021220 | A1 | 3/2006 |
| WO | 2006037140 | A2 | 4/2006 |
| WO | 2007005851 | A2 | 1/2007 |
| WO | 2007007845 | A1 | 1/2007 |
| WO | 2007042823 | A2 | 4/2007 |
| WO | 2007055651 | A1 | 5/2007 |
| WO | 2006098950 | A3 | 11/2007 |
| WO | 2007134608 | A2 | 11/2007 |
| WO | 2007128156 | A3 | 2/2008 |
| WO | 2008026106 | A2 | 3/2008 |
| WO | 2008078117 | A1 | 7/2008 |
| WO | 2008104019 | A1 | 9/2008 |
| WO | 2008141471 | A1 | 11/2008 |
| WO | 2009004368 | A1 | 1/2009 |
| WO | 2009004369 | A1 | 1/2009 |
| WO | 2009052496 | A1 | 4/2009 |
| WO | 2009052502 | A1 | 4/2009 |
| WO | 2009007702 | A4 | 7/2009 |
| WO | 2009101738 | A1 | 8/2009 |
| WO | 2010058192 | A1 | 5/2010 |
| WO | 2010030122 | A3 | 7/2010 |
| WO | 2010101915 | A3 | 1/2011 |
| WO | 2011018132 | A1 | 2/2011 |
| WO | 2011018133 | A1 | 2/2011 |
| WO | 2011024864 | A1 | 3/2011 |
| WO | 2011054118 | A1 | 5/2011 |
| WO | 2011079132 | A1 | 6/2011 |
| WO | 2011107972 | A1 | 9/2011 |
| WO | 2011108972 | A1 | 9/2011 |
| WO | 2011117292 | A1 | 9/2011 |
| WO | 2011123219 | A1 | 10/2011 |
| WO | 2011132043 | A1 | 10/2011 |
| WO | 2012012908 | A1 | 2/2012 |
| WO | 2012020506 | A1 | 2/2012 |
| WO | 2012065274 | A1 | 5/2012 |
| WO | 2012097462 | A1 | 7/2012 |
| WO | 2012098796 | A1 | 7/2012 |
| WO | 2012101288 | A1 | 8/2012 |
| WO | 2012175916 | A1 | 12/2012 |
| WO | 2013018435 | A1 | 2/2013 |
| WO | 2013033429 | A1 | 3/2013 |
| WO | 2013055434 | A1 | 4/2013 |
| WO | 2013082397 | A1 | 6/2013 |
| WO | 2013103291 | A2 | 7/2013 |
| WO | 2013131109 | A1 | 9/2013 |
| WO | 2013167478 | A1 | 11/2013 |
| WO | 2013177716 | A1 | 12/2013 |
| WO | 2014041534 | A1 | 3/2014 |
| WO | 2014046420 | A1 | 3/2014 |
| WO | 2014118518 | A1 | 8/2014 |
| WO | 2014160852 | A1 | 10/2014 |
| WO | 2015023599 | A1 | 2/2015 |
| WO | 2015052348 | A1 | 4/2015 |
| WO | 2015068384 | A1 | 5/2015 |
| WO | 2015169403 | A1 | 11/2015 |
| WO | 2015170307 | A1 | 11/2015 |
| WO | 2015197462 | A1 | 12/2015 |
| WO | 2016051385 | A1 | 4/2016 |
| WO | 2016055989 | A1 | 4/2016 |
| WO | 2016071894 | A1 | 5/2016 |
| WO | 2016103242 | A1 | 6/2016 |

(56) References Cited

FOREIGN PATENT DOCUMENTS

| | | | |
|---|---|---|---|
| WO | 2016116915 | A1 | 7/2016 |
| WO | 2016124203 | A1 | 8/2016 |
| WO | 2016139448 | A1 | 9/2016 |
| WO | 2016166562 | A1 | 10/2016 |
| WO | 2016167535 | A1 | 10/2016 |
| WO | 2016191574 | A1 | 12/2016 |
| WO | 2016200088 | A1 | 12/2016 |
| WO | 2016200361 | A1 | 12/2016 |
| WO | 2016204731 | A1 | 12/2016 |
| WO | 2017001532 | A2 | 1/2017 |
| WO | 2017001846 | A1 | 1/2017 |
| WO | 2017075226 | A1 | 5/2017 |
| WO | 2017100511 | A1 | 6/2017 |
| WO | 2017152198 | A1 | 9/2017 |
| WO | 2017153320 | A1 | 9/2017 |
| WO | 2017153357 | A1 | 9/2017 |
| WO | 2017162559 | A1 | 9/2017 |
| WO | 2017205446 | A1 | 11/2017 |
| WO | 2017209779 | A1 | 12/2017 |
| WO | 2017210524 | A1 | 12/2017 |
| WO | 2018022414 | A1 | 2/2018 |
| WO | 2018044781 | A1 | 3/2018 |
| WO | 2018056953 | A1 | 3/2018 |
| WO | 2018090550 | A1 | 5/2018 |
| WO | 2018138513 | A1 | 8/2018 |
| WO | 2018144318 | A1 | 8/2018 |
| WO | 2018144463 | A1 | 8/2018 |
| WO | 2018150263 | A1 | 8/2018 |
| WO | 2018150268 | A1 | 8/2018 |
| WO | 2018152156 | A1 | 8/2018 |
| WO | 2018183791 | A1 | 10/2018 |
| WO | 2018150267 | A3 | 11/2018 |
| WO | 2018200721 | A1 | 11/2018 |
| WO | 2018235026 | A1 | 12/2018 |
| WO | 2018235065 | A1 | 12/2018 |
| WO | 2019004404 | A1 | 1/2019 |
| WO | 2019038732 | A1 | 2/2019 |
| WO | 2019041005 | A1 | 3/2019 |
| WO | 2019044217 | A1 | 3/2019 |
| WO | 2019044218 | A1 | 3/2019 |
| WO | 2019044219 | A1 | 3/2019 |
| WO | 2019050959 | A1 | 3/2019 |
| WO | 2019065541 | A1 | 4/2019 |
| WO | 2019096845 | A1 | 5/2019 |
| WO | 2019150385 | A1 | 8/2019 |
| WO | 2019161094 | A1 | 8/2019 |
| WO | 2019188566 | A1 | 10/2019 |
| WO | 2019190593 | A1 | 10/2019 |
| WO | 2019212949 | A1 | 11/2019 |
| WO | 2019212950 | A1 | 11/2019 |
| WO | 2019212951 | A1 | 11/2019 |
| WO | 2019212952 | A1 | 11/2019 |
| WO | 2019212954 | A1 | 11/2019 |
| WO | 2019212955 | A1 | 11/2019 |
| WO | 2019212956 | A1 | 11/2019 |
| WO | 2019214787 | A1 | 11/2019 |
| WO | 2019214788 | A1 | 11/2019 |
| WO | 2019226826 | A1 | 11/2019 |
| WO | 2019239433 | A1 | 12/2019 |
| WO | 2020000994 | A1 | 1/2020 |
| WO | 2020020618 | A1 | 1/2020 |
| WO | 2020033752 | A1 | 2/2020 |
| WO | 2020038822 | A1 | 2/2020 |
| WO | 2020088409 | A1 | 5/2020 |
| WO | 2020049394 | A3 | 6/2020 |
| WO | 2020120657 | A1 | 6/2020 |
| WO | 2020152575 | A1 | 7/2020 |
| WO | 2020182923 | A1 | 9/2020 |
| WO | 2020204967 | A1 | 10/2020 |
| WO | 2020205939 | A1 | 10/2020 |
| WO | 2020209898 | A1 | 10/2020 |
| WO | 2020242790 | A1 | 12/2020 |
| WO | 2020251893 | A1 | 12/2020 |
| WO | 2020256865 | A1 | 12/2020 |
| WO | 2021007144 | A1 | 1/2021 |
| WO | 2021007345 | A1 | 1/2021 |
| WO | 2021010844 | A1 | 1/2021 |
| WO | 2021016026 | A1 | 1/2021 |
| WO | 2021016056 | A1 | 1/2021 |
| WO | 2021016300 | A1 | 1/2021 |
| WO | 2021025919 | A1 | 2/2021 |
| WO | 2021034886 | A1 | 2/2021 |
| WO | 2021041123 | A1 | 3/2021 |
| WO | 2021046501 | A1 | 3/2021 |
| WO | 2021086868 | A1 | 5/2021 |
| WO | 2021094352 | A1 | 5/2021 |
| WO | 2021094639 | A1 | 5/2021 |
| WO | 2021097067 | A1 | 5/2021 |
| WO | 2021102296 | A1 | 5/2021 |
| WO | 2021107025 | A1 | 6/2021 |
| WO | 2021138411 | A1 | 7/2021 |
| WO | 2021138414 | A1 | 7/2021 |
| WO | 2021154686 | A1 | 8/2021 |
| WO | 2021155206 | A1 | 8/2021 |
| WO | 2021170075 | A1 | 9/2021 |
| WO | 2021173436 | A1 | 9/2021 |
| WO | 2021188817 | A1 | 9/2021 |
| WO | 2021195384 | A1 | 9/2021 |
| WO | 2021205995 | A1 | 10/2021 |
| WO | 2021207621 | A1 | 10/2021 |
| WO | 2021211568 | A1 | 10/2021 |
| WO | 2021211801 | A1 | 10/2021 |
| WO | 2021211914 | A1 | 10/2021 |
| WO | 2021216419 | A1 | 10/2021 |
| WO | 2021216422 | A1 | 10/2021 |
| WO | 2021231532 | A1 | 11/2021 |
| WO | 2021247523 | A1 | 12/2021 |
| WO | 2021257202 | A1 | 12/2021 |
| WO | 2022006256 | A1 | 1/2022 |
| WO | 2022029662 | A1 | 2/2022 |
| WO | 2022031943 | A1 | 2/2022 |
| WO | 2022035745 | A1 | 2/2022 |
| WO | 2022051220 | A1 | 3/2022 |
| WO | 2022051360 | A1 | 3/2022 |
| WO | 2022054613 | A1 | 3/2022 |
| WO | 2022066704 | A1 | 3/2022 |
| WO | 2022067392 | A1 | 4/2022 |
| WO | 2022069950 | A1 | 4/2022 |
| WO | 2022071429 | A1 | 4/2022 |
| WO | 2022076322 | A1 | 4/2022 |
| WO | 2022076427 | A2 | 4/2022 |
| WO | 2022086898 | A1 | 4/2022 |
| WO | 2022090199 | A1 | 5/2022 |
| WO | 2022098536 | A1 | 5/2022 |
| WO | 2022099087 | A1 | 5/2022 |
| WO | 2022101999 | A1 | 5/2022 |
| WO | 2022115692 | A1 | 6/2022 |
| WO | 2022125685 | A1 | 6/2022 |
| WO | 2022140545 | A1 | 6/2022 |
| WO | 2022145231 | A1 | 7/2022 |
| WO | 2022150290 | A1 | 7/2022 |
| WO | 2022150360 | A1 | 7/2022 |
| WO | 2022150463 | A1 | 7/2022 |
| WO | 2022159392 | A1 | 7/2022 |
| WO | 2022170182 | A1 | 8/2022 |
| WO | 2022173803 | A1 | 8/2022 |
| WO | 2022182385 | A1 | 9/2022 |
| WO | 2022187152 | A1 | 9/2022 |
| WO | 2022192188 | A1 | 9/2022 |
| WO | 2022192347 | A1 | 9/2022 |
| WO | 2022204000 | A1 | 9/2022 |
| WO | 2022216507 | A1 | 10/2022 |
| WO | 2022216776 | A1 | 10/2022 |
| WO | 2022222030 | A1 | 10/2022 |
| WO | 2022251184 | A1 | 12/2022 |
| WO | 2022251425 | A1 | 12/2022 |
| WO | 2022271783 | A1 | 12/2022 |
| WO | 2023286058 | A1 | 1/2023 |
| WO | 2023014639 | A1 | 2/2023 |
| WO | 2023014641 | A1 | 2/2023 |
| WO | 2023018475 | A2 | 2/2023 |
| WO | 2023018656 | A1 | 2/2023 |
| WO | 2023018657 | A1 | 2/2023 |
| WO | 2023023777 | A1 | 3/2023 |

(56) References Cited

FOREIGN PATENT DOCUMENTS

| | | | |
|---|---|---|---|
| WO | 2023034139 | A1 | 3/2023 |
| WO | 2023034453 | A1 | 3/2023 |
| WO | 2023038945 | A1 | 3/2023 |
| WO | 2023038950 | A1 | 3/2023 |
| WO | 2023049109 | A1 | 3/2023 |
| WO | 2023049156 | A1 | 3/2023 |
| WO | 2023049175 | A1 | 3/2023 |
| WO | 2023086394 | A1 | 5/2023 |
| WO | 2023146529 | A1 | 8/2023 |
| WO | 2023149884 | A1 | 8/2023 |
| WO | 2023149902 | A1 | 8/2023 |
| WO | 2023149903 | A1 | 8/2023 |
| WO | 2023154390 | A1 | 8/2023 |
| WO | 2023163725 | A1 | 8/2023 |
| WO | 2023191764 | A1 | 10/2023 |
| WO | 2023244238 | A1 | 12/2023 |
| WO | 2024043871 | A1 | 2/2024 |
| WO | 2024058788 | A1 | 3/2024 |
| WO | 2024253655 | A1 | 12/2024 |
| WO | 2025034959 | A1 | 2/2025 |
| WO | 2025038087 | A1 | 2/2025 |
| WO | 2025038088 | A1 | 2/2025 |
| WO | 2025048789 | A1 | 3/2025 |
| WO | 2025071622 | A1 | 4/2025 |
| WO | 2025179267 | A1 | 8/2025 |
| WO | 2026035497 | A1 | 2/2026 |

OTHER PUBLICATIONS

Advisory Action for U.S. Appl. No. 16/452,258 mailed Oct. 26, 2022.
Advisory Action for U.S. Appl. No. 16/478,180 mailed Sep. 21, 2022.
Advisory Action for U.S. Appl. No. 16/904,868 mailed Jun. 15, 2022.
Final Office Action for U.S. Appl. No. 16/245,726 mailed Nov. 25, 2022.
Final Office Action for U.S. Appl. No. 16/369,676 mailed Dec. 5, 2022.
Final Office Action for U.S. Appl. No. 16/433,773 mailed Oct. 25, 2022.
Final Office Action for U.S. Appl. No. 16/449,039 mailed Aug. 1, 2022.
Final Office Action for U.S. Appl. No. 16/452,258 mailed Jun. 14, 2022.
Final Office Action for U.S. Appl. No. 16/478,180 mailed Jun. 22, 2022.
Final Office Action for U.S. Appl. No. 17/662,700 mailed Sep. 30, 2022.
International Search Report and Written Opinion from International Application No. PCT/IB2021/057173 mailed Nov. 5, 2021.
International Search Report and Written Opinion from International Application No. PCT/US2020/057562 mailed Jan. 27, 2021.
International Search Report and Written Opinion from International Application No. PCT/US2021/026607 mailed Jul. 29, 2021.
International Search Report and Written Opinion from International Application No. PCT/US2021/039866 mailed Oct. 7, 2021.
International Search Report and Written Opinion from International Application No. PCT/US2021/049404 mailed Jan. 18, 2022.
International Search Report and Written Opinion from International Application No. PCT/US2021/051456 mailed Jan. 19, 2022.
International Search Report and Written Opinion from International Application No. PCT/US2021/053593 mailed Apr. 11, 2022.
International Search Report and Written Opinion from International Application No. PCT/US2021/055515 mailed Jan. 28, 2022.
International Search Report and Written Opinion from International Application No. PCT/US2021/062440 mailed Mar. 28, 2022.
International Search Report and Written Opinion from International Application No. PCT/US2022/011108 mailed Apr. 22, 2022.
International Search Report and Written Opinion from International Application No. PCT/US2022/011281 mailed Apr. 25, 2022.
International Search Report and Written Opinion from International Application No. PCT/US2022/011419 mailed Jun. 7, 2022.
International Search Report and Written Opinion from International Application No. PCT/US2022/011421 mailed Jun. 13, 2022.
International Search Report and Written Opinion from International Application No. PCT/US2022/012794 mailed May 3, 2022.
International Search Report and Written Opinion from International Application No. PCT/US2022/014285 mailed Sep. 28, 2022.
International Search Report and Written Opinion from International Application No. PCT/US2022/014749 mailed Sep. 28, 2022.
International Search Report and Written Opinion from International Application No. PCT/US2022/015026 mailed Oct. 31, 2022.
International Search Report and Written Opinion from International Application No. PCT/US2022/015045 mailed Sep. 9, 2022.
International Search Report and Written Opinion from International Application No. PCT/US2022/015073 mailed Sep. 8, 2022.
International Search Report and Written Opinion from International Application No. PCT/US2022/015418_mailed Nov. 11, 2022.
International Search Report and Written Opinion from International Application No. PCT/US2022/015471 mailed May 16, 2022.
International Search Report and Written Opinion from International Application No. PCT/US2022/015492 mailed Apr. 26, 2022.
International Search Report and Written Opinion from International Application No. PCT/US2022/015781 mailed May 6, 2022.
International Search Report and Written Opinion from International Application No. PCT/US2022/016942 mailed Jun. 8, 2022.
International Search Report and Written Opinion from International Application No. PCT/US2022/018170 mailed May 31, 2022.
International Search Report and Written Opinion from International Application No. PCT/US2022/019254 mailed Jun. 7, 2022.
International Search Report and Written Opinion from International Application No. PCT/US2022/019480 mailed Jun. 13, 2022.
International Search Report and Written Opinion from International Application No. PCT/US2022/021103 mailed Jun. 23, 2022.
International Search Report and Written Opinion from International Application No. PCT/US2022/022111 mailed Oct. 26, 2022.
International Search Report and Written Opinion from International Application No. PCT/US2022/023594 mailed Jul. 12, 2022.
International Search Report and Written Opinion from International Application No. PCT/US2022/026667 mailed Aug. 22, 2022.
International Search Report and Written Opinion from International Application No. PCT/US2022/030685 mailed Oct. 31, 2022.
International Search Report and Written Opinion from International Application No. PCT/US2022/031032 mailed Sep. 9, 2022.
International Search Report and Written Opinion from International Application No. PCT/US2022/032424 mailed Oct. 11, 2022.
International Search Report and Written Opinion from International Application No. PCT/US2022/034457 mailed Oct. 12, 2022.
Issue Notification for U.S. Appl. No. 16/905,400 mailed Nov. 30, 2022.
Issue Notification for U.S. Appl. No. 17/088,272 mailed Jun. 15, 2022.
Issue Notification for U.S. Appl. No. 17/330,657 mailed Jun. 22, 2022.
Non-Final Office Action for U.S. Appl. No. 16/433,773 mailed Apr. 21, 2022.
Non-Final Office Action for U.S. Appl. No. 16/905,400 mailed Apr. 27, 2022.
Non-Final Office Action for U.S. Appl. No. 17/451,345 mailed Dec. 7, 2022.
Non-Final Office Action for U.S. Appl. No. 17/662,700 mailed Jul. 22, 2022.
Notice of Allowance for U.S. Appl. No. 16/899,956 mailed Apr. 19, 2022.
Notice of Allowance for U.S. Appl. No. 16/899,956 mailed Aug. 10, 2022.
Notice of Allowance for U.S. Appl. No. 16/899,956 mailed Dec. 1, 2022.
Notice of Allowance for U.S. Appl. No. 16/905,400 mailed Aug. 17, 2022.

(56) References Cited

OTHER PUBLICATIONS

Notice of Allowance for U.S. Appl. No. 17/461,036 mailed Oct. 6, 2022.
Notice of Allowance for U.S. Appl. No. 29/741,751 mailed Jun. 9, 2022.
U.S. Appl. No. 17/661,090, filed Apr. 28, 2022.
U.S. Appl. No. 17/662,700, filed May 10, 2022.
U.S. Appl. No. 17/663,046, filed May 12, 2022.
U.S. Appl. No. 17/664,914, filed May 25, 2022.
U.S. Appl. No. 17/749,340, filed May 20, 2022.
U.S. Appl. No. 17/756,201, filed May 19, 2022.
U.S. Appl. No. 17/758,152, filed Jun. 29, 2022.
U.S. Appl. No. 17/758,316, filed Jul. 1, 2022.
U.S. Appl. No. 17/759,697, filed Jul. 28, 2022.
U.S. Appl. No. 17/878,268, filed Aug. 1, 2022.
U.S. Appl. No. 17/907,125, filed Sep. 23, 2022.
U.S. Appl. No. 17/912,147, filed Sep. 16, 2022.
U.S. Appl. No. 17/929,887, filed Sep. 6, 2022.
U.S. Appl. No. 17/930,238, filed Sep. 7, 2022.
U.S. Appl. No. 17/933,590, filed Sep. 20, 2022.
U.S. Appl. No. 17/996,064, filed Oct. 12, 2022.
U.S. Appl. No. 17/996,155, filed Oct. 13, 2022.
U.S. Appl. No. 17/996,253, filed Oct. 14, 2022.
U.S. Appl. No. 17/996,468, filed Oct. 18, 2022.
U.S. Appl. No. 17/996,556, filed Oct. 19, 2022.
U.S. Appl. No. 17/999,648, filed Nov. 22, 2022.
U.S. Appl. No. 62/926,767, filed Oct. 28, 2019.
U.S. Appl. No. 62/967,158, filed Jan. 26, 2020.
U.S. Appl. No. 62/991,754, filed Mar. 19, 2020.
U.S. Appl. No. 63/008,112, filed Apr. 10, 2020.
U.S. Appl. No. 63/191,558, filed May 21, 2021.
U.S. Appl. No. 63/192,289, filed May 24, 2021.
U.S. Appl. No. 63/230,897, filed Aug. 9, 2021.
U.S. Appl. No. 63/241,328, filed Sep. 7, 2021.
Advisory Action for U.S. Appl. No. 16/245,726 mailed Apr. 19, 2023.
Advisory Action for U.S. Appl. No. 16/369,676 mailed Mar. 24, 2023.
Advisory Action for U.S. Appl. No. 16/433,773 mailed Dec. 29, 2023.
Advisory Action for U.S. Appl. No. 16/433,773 mailed Feb. 15, 2023.
Advisory Action for U.S. Appl. No. 16/449,039 mailed Jan. 25, 2024.
Advisory Action for U.S. Appl. No. 16/452,258 mailed Apr. 8, 2024.
Advisory Action for U.S. Appl. No. 16/478,180 mailed Sep. 7, 2023.
Advisory Action for U.S. Appl. No. 16/904,868 mailed Jan. 2, 2024.
Advisory Action for U.S. Appl. No. 17/051,550 mailed Sep. 8, 2023.
Advisory Action for U.S. Appl. No. 17/051,585 mailed Oct. 17, 2023.
Advisory Action for U.S. Appl. No. 17/179,116 mailed Jan. 8, 2024.
Advisory Action for U.S. Appl. No. 17/444,792 mailed Aug. 25, 2023.
Advisory Action for U.S. Appl. No. 17/446,256 mailed Dec. 8, 2023.
Advisory Action for U.S. Appl. No. 17/446,654 mailed Apr. 15, 2024.
Advisory Action for U.S. Appl. No. 17/448,811 mailed Nov. 15, 2023.
Advisory Action for U.S. Appl. No. 17/450,864 mailed Mar. 21, 2024.
Advisory Action for U.S. Appl. No. 17/451,345 mailed Oct. 20, 2023.
Advisory Action for U.S. Appl. No. 17/451,354 mailed Jan. 30, 2024.
Advisory Action for U.S. Appl. No. 17/453,260 mailed Dec. 22, 2023.
Advisory Action for U.S. Appl. No. 17/501,591 mailed Feb. 22, 2024.
Advisory Action for U.S. Appl. No. 17/646,771 mailed Feb. 29, 2024.
Advisory Action for U.S. Appl. No. 17/653,137 mailed Dec. 1, 2023.
Advisory Action for U.S. Appl. No. 17/655,464 mailed Dec. 13, 2023.
Advisory Action for U.S. Appl. No. 17/661,090 mailed Feb. 26, 2024.
Advisory Action for U.S. Appl. No. 17/662,700 mailed Jan. 30, 2023.
Advisory Action for U.S. Appl. No. 17/663,330 mailed Feb. 27, 2024.
Advisory Action for U.S. Appl. No. 17/664,487 mailed Mar. 13, 2024.
Advisory Action for U.S. Appl. No. 18/139,523 mailed Apr. 24, 2024.
Advisory Action for U.S. Appl. No. 18/140,751 mailed Apr. 24, 2024.
Advisory Action for U.S. Appl. No. 18/164,800 mailed Feb. 12, 2024.
Communication of Notice of Opposition of European Application No. 17807547.9 mailed Jan. 5, 2024.
Corrected Notice of Allowability for U.S. Appl. No. 16/369,676 mailed Dec. 7, 2023.
Corrected Notice of Allowability for U.S. Appl. No. 17/326,980 mailed Feb. 8, 2024.
Corrected Notice of Allowability for U.S. Appl. No. 17/657,474 mailed Mar. 13, 2024.
Final Office Action for U.S. Appl. No. 16/369,676 mailed Aug. 31, 2023.
Final Office Action for U.S. Appl. No. 16/433,773 mailed Oct. 10, 2023.
Final Office Action for U.S. Appl. No. 16/449,039 mailed Nov. 21, 2023.
Final Office Action for U.S. Appl. No. 16/452,258 mailed Dec. 21, 2023.
Final Office Action for U.S. Appl. No. 16/478,180 mailed Feb. 28, 2024.
Final Office Action for U.S. Appl. No. 16/478,180 mailed May 31, 2023.
Final Office Action for U.S. Appl. No. 16/904,868 mailed Nov. 2, 2023.
Final Office Action for U.S. Appl. No. 17/051,399 mailed Jan. 8, 2024.
Final Office Action for U.S. Appl. No. 17/051,399 mailed Mar. 9, 2023.
Final Office Action for U.S. Appl. No. 17/051,550 mailed May 23, 2023.
Final Office Action for U.S. Appl. No. 17/051,585 mailed Jul. 27, 2023.
Final Office Action for U.S. Appl. No. 17/179,116 mailed Oct. 31, 2023.
Final Office Action for U.S. Appl. No. 17/444,792 mailed Apr. 3, 2024.
Final Office Action for U.S. Appl. No. 17/444,792 mailed Jun. 15, 2023.
Final Office Action for U.S. Appl. No. 17/446,256 mailed Sep. 19, 2023.
Final Office Action for U.S. Appl. No. 17/446,654 mailed Jan. 31, 2024.
Final Office Action for U.S. Appl. No. 17/448,811 mailed Aug. 3, 2023.
Final Office Action for U.S. Appl. No. 17/450,864 mailed Dec. 28, 2023.
Final Office Action for U.S. Appl. No. 17/451,345 mailed Apr. 18, 2024.
Final Office Action for U.S. Appl. No. 17/451,345 mailed May 3, 2023.
Final Office Action for U.S. Appl. No. 17/451,354 mailed Oct. 30, 2023.
Final Office Action for U.S. Appl. No. 17/453,260 mailed Oct. 5, 2023.

(56) References Cited

OTHER PUBLICATIONS

Final Office Action for U.S. Appl. No. 17/501,591 mailed Nov. 14, 2023.
Final Office Action for U.S. Appl. No. 17/645,821 mailed Apr. 3, 2024.
Final Office Action for U.S. Appl. No. 17/646,771 mailed Dec. 21, 2023.
Final Office Action for U.S. Appl. No. 17/653,137 mailed Sep. 21, 2023.
Final Office Action for U.S. Appl. No. 17/655,464 mailed Sep. 1, 2023.
Final Office Action for U.S. Appl. No. 17/661,090 mailed Dec. 11, 2023.
Final Office Action for U.S. Appl. No. 17/663,330 mailed Dec. 12, 2023.
Final Office Action for U.S. Appl. No. 17/664,487 mailed Jan. 4, 2024.
Final Office Action for U.S. Appl. No. 17/808,354 mailed Apr. 10, 2024.
Final Office Action for U.S. Appl. No. 18/139,523 mailed Dec. 22, 2023.
Final Office Action for U.S. Appl. No. 18/140,163 mailed Mar. 27, 2024.
Final Office Action for U.S. Appl. No. 18/140,751 mailed Jan. 17, 2024.
Final Office Action for U.S. Appl. No. 18/164,800 mailed Dec. 6, 2023.
International Search Report and Written Opinion from International Application No. PCT/US2022/015420 mailed Nov. 18, 2022.
International Search Report and Written Opinion from International Application No. PCT/US2022/018159 mailed Dec. 12, 2022.
International Search Report and Written Opinion from International Application No. PCT/US2022/034744 mailed Dec. 9, 2022.
International Search Report and Written Opinion from International Application No. PCT/US2022/039018 mailed Jan. 10, 2023.
International Search Report and Written Opinion from International Application No. PCT/US2022/039022 mailed Jan. 10, 2023.
International Search Report and Written Opinion from International Application No. PCT/US2022/039711 mailed Jan. 12, 2023.
International Search Report and Written Opinion from International Application No. PCT/US2022/039714 mailed Nov. 22, 2022.
International Search Report and Written Opinion from International Application No. PCT/US2022/041085 mailed Mar. 16, 2023.
International Search Report and Written Opinion from International Application No. PCT/US2022/041688 mailed Nov. 21, 2022.
International Search Report and Written Opinion from International Application No. PCT/US2022/042719 mailed Dec. 5, 2022.
International Search Report and Written Opinion from International Application No. PCT/US2022/042725 mailed Dec. 19, 2022.
International Search Report and Written Opinion from International Application No. PCT/US2022/043818 mailed Mar. 24, 2023.
International Search Report and Written Opinion from International Application No. PCT/US2022/044107 mailed Dec. 23, 2022.
International Search Report and Written Opinion from International Application No. PCT/US2022/044208 mailed May 8, 2023.
International Search Report and Written Opinion from International Application No. PCT/US2022/044212 mailed Jan. 20, 2023.
International Search Report and Written Opinion from International Application No. PCT/US2022/044243 mailed Feb. 24, 2023.
International Search Report and Written Opinion from International Application No. PCT/US2022/049300 mailed Jun. 6, 2023.
International Search Report and Written Opinion from International Application No. PCT/US2022/050909 mailed Jul. 24, 2023.
International Search Report and Written Opinion from International Application No. PCT/US2023/012696 mailed Jul. 6, 2023.
International Search Report and Written Opinion from International Application No. PCT/US2023/018474 mailed Sep. 11, 2023.
International Search Report and Written Opinion from International Application No. PCT/US2023/024805 mailed Dec. 14, 2023.
International Search Report and Written Opinion from International Application No. PCT/US2023/025192 mailed Feb. 7, 2024.
International Search Report and Written Opinion from International Application No. PCT/US2023/025939 mailed Feb. 7, 2024.
International Search Report and Written Opinion from International Application No. PCT/US2023/030373 mailed Mar. 13, 2024.
International Search Report and Written Opinion from International Application No. PCT/US2023/031433 mailed Mar. 4, 2024.
International Search Report and Written Opinion from International Application No. PCT/US2023/031740 mailed Mar. 4, 2024.
Issue Notification for U.S. Appl. No. 16/245,726 mailed Oct. 18, 2023.
Issue Notification for U.S. Appl. No. 16/899,956 mailed Mar. 29, 2023.
Issue Notification for U.S. Appl. No. 17/051,550 mailed Mar. 13, 2024.
Issue Notification for U.S. Appl. No. 17/051,554 mailed Mar. 6, 2024.
Issue Notification for U.S. Appl. No. 17/461,036 mailed Oct. 11, 2023.
Issue Notification for U.S. Appl. No. 17/663,046 mailed Dec. 20, 2023.
Issue Notification for U.S. Appl. No. 18/299,788 mailed Feb. 21, 2024.
Non-Final Office Action for U.S. Appl. No. 16/369,676 mailed Feb. 29, 2024.
Non-Final Office Action for U.S. Appl. No. 16/433,773 mailed Apr. 11, 2023.
Non-Final Office Action for U.S. Appl. No. 16/433,773 mailed Feb. 26, 2024.
Non-Final Office Action for U.S. Appl. No. 16/449,039 mailed Apr. 27, 2023.
Non-Final Office Action for U.S. Appl. No. 16/452,145 mailed Mar. 28, 2023.
Non-Final Office Action for U.S. Appl. No. 16/452,145 mailed Nov. 2, 2023.
Non-Final Office Action for U.S. Appl. No. 16/452,258 mailed Apr. 26, 2023.
Non-Final Office Action for U.S. Appl. No. 16/478,180 mailed Dec. 20, 2022.
Non-Final Office Action for U.S. Appl. No. 16/478,180 mailed Nov. 7, 2023.
Non-Final Office Action for U.S. Appl. No. 16/904,868 mailed Mar. 12, 2024.
Non-Final Office Action for U.S. Appl. No. 16/904,868 mailed Mar. 15, 2023.
Non-Final Office Action for U.S. Appl. No. 17/051,399 mailed Aug. 18, 2023.
Non-Final Office Action for U.S. Appl. No. 17/051,550 mailed Dec. 15, 2022.
Non-Final Office Action for U.S. Appl. No. 17/051,550 mailed Oct. 24, 2023.
Non-Final Office Action for U.S. Appl. No. 17/051,585 mailed Jan. 8, 2024.
Non-Final Office Action for U.S. Appl. No. 17/051,585 mailed Mar. 29, 2023.
Non-Final Office Action for U.S. Appl. No. 17/051,600 mailed Jan. 17, 2024.
Non-Final Office Action for U.S. Appl. No. 17/179,116 mailed Feb. 26, 2024.
Non-Final Office Action for U.S. Appl. No. 17/179,116 mailed Mar. 24, 2023.
Non-Final Office Action for U.S. Appl. No. 17/326,980 mailed Jul. 11, 2023.
Non-Final Office Action for U.S. Appl. No. 17/444,792 mailed Feb. 10, 2023.
Non-Final Office Action for U.S. Appl. No. 17/444,792 mailed Nov. 17, 2023.
Non-Final Office Action for U.S. Appl. No. 17/446,256 mailed Apr. 13, 2023.
Non-Final Office Action for U.S. Appl. No. 17/446,256 mailed Feb. 13, 2024.

(56) References Cited

OTHER PUBLICATIONS

Non-Final Office Action for U.S. Appl. No. 17/446,654 mailed Sep. 8, 2023.
Non-Final Office Action for U.S. Appl. No. 17/447,123 mailed Jan. 24, 2024.
Non-Final Office Action for U.S. Appl. No. 17/448,811 mailed Jan. 17, 2024.
Non-Final Office Action for U.S. Appl. No. 17/448,811 mailed Mar. 1, 2023.
Non-Final Office Action for U.S. Appl. No. 17/450,864 mailed May 10, 2023.
Non-Final Office Action for U.S. Appl. No. 17/451,345 mailed Jan. 17, 2024.
Non-Final Office Action for U.S. Appl. No. 17/451,354 mailed Apr. 4, 2024.
Non-Final Office Action for U.S. Appl. No. 17/451,354 mailed May 3, 2023.
Non-Final Office Action for U.S. Appl. No. 17/453,260 mailed Mar. 14, 2023.
Non-Final Office Action for U.S. Appl. No. 17/453,560 mailed Oct. 16, 2023.
Non-Final Office Action for U.S. Appl. No. 17/501,591 mailed Apr. 25, 2023.
Non-Final Office Action for U.S. Appl. No. 17/597,673 mailed Mar. 20, 2024.
Non-Final Office Action for U.S. Appl. No. 17/645,821 mailed Oct. 25, 2023.
Non-Final Office Action for U.S. Appl. No. 17/646,771 mailed Apr. 24, 2024.
Non-Final Office Action for U.S. Appl. No. 17/646,771 mailed Jul. 5, 2023.
Non-Final Office Action for U.S. Appl. No. 17/653,137 mailed Apr. 7, 2023.
Non-Final Office Action for U.S. Appl. No. 17/653,137 mailed Jan. 18, 2024.
Non-Final Office Action for U.S. Appl. No. 17/653,920 mailed Mar. 15, 2024.
Non-Final Office Action for U.S. Appl. No. 17/655,464 mailed Mar. 14, 2023.
Non-Final Office Action for U.S. Appl. No. 17/655,464 mailed Mar. 26, 2024.
Non-Final Office Action for U.S. Appl. No. 17/657,474 mailed Sep. 12, 2023.
Non-Final Office Action for U.S. Appl. No. 17/661,090 mailed Jul. 6, 2023.
Non-Final Office Action for U.S. Appl. No. 17/663,330 mailed Jun. 29, 2023.
Non-Final Office Action for U.S. Appl. No. 17/664,487 mailed Jun. 8, 2023.
Non-Final Office Action for U.S. Appl. No. 17/664,914 mailed Jan. 31, 2024.
Non-Final Office Action for U.S. Appl. No. 17/808,354 mailed Nov. 28, 2023.
Non-Final Office Action for U.S. Appl. No. 18/003,029 mailed Mar. 26, 2024.
Non-Final Office Action for U.S. Appl. No. 18/134,857 mailed Jan. 25, 2024.
Non-Final Office Action for U.S. Appl. No. 18/139,523 mailed Aug. 17, 2023.
Non-Final Office Action for U.S. Appl. No. 18/140,163 mailed Nov. 9, 2023.
Non-Final Office Action for U.S. Appl. No. 18/140,751 mailed Sep. 14, 2023.
Non-Final Office Action for U.S. Appl. No. 18/164,800 mailed Mar. 22, 2024.
Non-Final Office Action for U.S. Appl. No. 18/198,464 mailed Dec. 7, 2023.
Notice of Allowance for U.S. Appl. No. 16/245,726 mailed Jul. 6, 2023.
Notice of Allowance for U.S. Appl. No. 16/369,676 mailed Nov. 14, 2023.
Notice of Allowance for U.S. Appl. No. 16/449,039 mailed Dec. 15, 2022.
Notice of Allowance for U.S. Appl. No. 16/449,039 mailed Mar. 28, 2024.
Notice of Allowance for U.S. Appl. No. 17/051,550 mailed Feb. 7, 2024.
Notice of Allowance for U.S. Appl. No. 17/051,554 mailed Jul. 6, 2023.
Notice of Allowance for U.S. Appl. No. 17/051,554 mailed Oct. 18, 2023.
Notice of Allowance for U.S. Appl. No. 17/326,980 mailed Apr. 5, 2024.
Notice of Allowance for U.S. Appl. No. 17/326,980 mailed Jan. 29, 2024.
Notice of Allowance for U.S. Appl. No. 17/453,260 mailed Apr. 8, 2024.
Notice of Allowance for U.S. Appl. No. 17/453,560 mailed Jan. 31, 2024.
Notice of Allowance for U.S. Appl. No. 17/461,036 mailed Feb. 22, 2023.
Notice of Allowance for U.S. Appl. No. 17/461,036 mailed Jun. 30, 2023.
Notice of Allowance for U.S. Appl. No. 17/657,474 mailed Mar. 5, 2024.
Notice of Allowance for U.S. Appl. No. 17/657,474 mailed May 2, 2024.
Notice of Allowance for U.S. Appl. No. 17/662,700 mailed Jul. 28, 2023.
Notice of Allowance for U.S. Appl. No. 17/662,700 mailed Mar. 28, 2023.
Notice of Allowance for U.S. Appl. No. 17/662,700 mailed Mar. 6, 2024.
Notice of Allowance for U.S. Appl. No. 17/662,700 mailed Nov. 15, 2023.
Notice of Allowance for U.S. Appl. No. 17/663,046 mailed Jan. 30, 2023.
Notice of Allowance for U.S. Appl. No. 18/198,464 mailed Apr. 17, 2024.
Notice of Allowance for U.S. Appl. No. 18/299,788 mailed Jul. 24, 2023.
Notice of Allowance for U.S. Appl. No. 18/299,788 mailed Nov. 6, 2023.
Restriction Requirement for U.S. Appl. No. 17/051,600 mailed Sep. 21, 2023.
Restriction Requirement for U.S. Appl. No. 17/326,980 mailed Mar. 20, 2023.
Restriction Requirement for U.S. Appl. No. 17/446,256 mailed Jan. 23, 2023.
Restriction Requirement for U.S. Appl. No. 17/645,821 mailed Jul. 12, 2023.
Restriction Requirement for U.S. Appl. No. 17/646,771 mailed Apr. 6, 2023.
Restriction Requirement for U.S. Appl. No. 17/657,474 mailed Jun. 30, 2023.
Restriction Requirement for U.S. Appl. No. 17/667,097 mailed Mar. 20, 2024.
Restriction Requirement for U.S. Appl. No. 18/134,857 mailed Oct. 23, 2023.
Submission in Opposition Proceedings for European Application No. 17807547.9 filed Jan. 10, 2024.
Supplemental Notice of Allowance for U.S. Appl. No. 17/051,550 mailed Feb. 21, 2024.
Supplemental Notice of Allowance for U.S. Appl. No. 17/051,554 mailed Feb. 14, 2024.
Text Messages to Lorena Eckert Re Prototype PureWick Holder dated Apr. 16, 2022.
U.S. Appl. No. 17/444,792, filed Aug. 10, 2021.
U.S. Appl. No. 17/451,719, filed Oct. 19, 2021.
U.S. Appl. No. 17/664,487, filed May 23, 2022.
U.S. Appl. No. 18/003,029, filed Dec. 22, 2022.
U.S. Appl. No. 18/006,807, filed Jan. 25, 2023.

(56) References Cited

OTHER PUBLICATIONS

U.S. Appl. No. 18/007,105, filed Jan. 27, 2023.
U.S. Appl. No. 18/041,109, filed Feb. 9, 2023.
U.S. Appl. No. 18/042,842, filed Feb. 24, 2023.
U.S. Appl. No. 18/043,618, filed Mar. 1, 2023.
U.S. Appl. No. 18/115,444, filed Feb. 28, 2023.
U.S. Appl. No. 18/134,857, filed Apr. 14, 2023.
U.S. Appl. No. 18/140,163, filed Apr. 27, 2023.
U.S. Appl. No. 18/140,751, filed Apr. 28, 2023.
U.S. Appl. No. 18/164,800, filed Feb. 6, 2023.
U.S. Appl. No. 18/198,464, filed May 17, 2023.
U.S. Appl. No. 18/246,121, filed Mar. 21, 2023.
U.S. Appl. No. 18/247,986, filed Apr. 5, 2023.
U.S. Appl. No. 18/249,577, filed Oct. 19, 2021.
U.S. Appl. No. 18/259,626, filed Jun. 28, 2023.
U.S. Appl. No. 18/260,122, filed Jun. 30, 2023.
U.S. Appl. No. 18/260,391, filed Jul. 5, 2023.
U.S. Appl. No. 18/260,394, filed Jul. 5, 2023.
U.S. Appl. No. 18/263,800, filed Aug. 1, 2023.
U.S. Appl. No. 18/264,004, filed Aug. 2, 2023.
U.S. Appl. No. 18/265,736, filed Jun. 7, 2023.
U.S. Appl. No. 18/294,370, filed Feb. 1, 2024.
U.S. Appl. No. 18/294,403, filed Feb. 1, 2024.
U.S. Appl. No. 18/299,788, filed Apr. 13, 2023.
U.S. Appl. No. 18/335,579, filed Jun. 15, 2023.
U.S. Appl. No. 18/373,424, filed Sep. 27, 2023.
U.S. Appl. No. 18/376,274, filed Oct. 3, 2023.
U.S. Appl. No. 18/389,009, filed Nov. 13, 2023.
U.S. Appl. No. 18/415,080, filed Jan. 17, 2024.
U.S. Appl. No. 18/426,795, filed Jan. 30, 2024.
U.S. Appl. No. 18/548,152, filed Aug. 28, 2023.
U.S. Appl. No. 18/549,387, filed Sep. 7, 2023.
U.S. Appl. No. 18/549,658, filed Sep. 8, 2023.
U.S. Appl. No. 18/553,625, filed Oct. 2, 2023.
U.S. Appl. No. 18/556,945, filed Oct. 24, 2023.
U.S. Appl. No. 18/558,502, filed Nov. 1, 2023.
U.S. Appl. No. 18/562,626, filed Nov. 20, 2023.
U.S. Appl. No. 18/563,672, filed Nov. 22, 2023.
U.S. Appl. No. 18/569,711, filed Dec. 13, 2023.
U.S. Appl. No. 18/569,778, filed Dec. 13, 2023.
U.S. Appl. No. 18/584,002, filed Feb. 22, 2024.
U.S. Appl. No. 18/610,523, filed Mar. 20, 2024.
U.S. Appl. No. 18/681,987, filed Feb. 7, 2024.
U.S. Appl. No. 18/682,006, filed Feb. 7, 2024.
U.S. Appl. No. 18/687,117, filed Feb. 27, 2024.
U.S. Appl. No. 18/688,023, filed Feb. 29, 2024.
U.S. Appl. No. 18/693,638, filed Mar. 20, 2024.
U.S. Appl. No. 18/694,090, filed Mar. 21, 2024.
U.S. Appl. No. 63/150,640, filed Feb. 18, 2021.
U.S. Appl. No. 63/308,190, filed Feb. 9, 2022.
U.S. Appl. No. 63/561,893, filed Dec. 11, 2023.
U.S. Appl. No. 63/596,012, filed Nov. 3, 2023.
U.S. Appl. No. 63/608,553, filed Dec. 11, 2023.
*PureWick Corporation* v. *Sage Products, LLC* Transcripts vol. 2, Mar. 29, 2022.
*PureWick Corporation* v. *Sage Products, LLC* Transcripts vol. 3, Mar. 30, 2022.
*PureWick Corporation* v. *Sage Products, LLC* Transcripts vol. 4, Mar. 31, 2022.
*PureWick Corporation* v. *Sage Products, LLC* Transcripts vol. 5, Apr. 1, 2022.
*PureWick Corporation* v. *Sage Products, LLC* Transcripts vol. 1, Mar. 28, 2022.
"AMXD Control Starter Kit", Omni Medical Systems, Inc., 1 page.
"AMXDmax Advanced Mission Extender Device User & Maintenance Guide", Omni Medical, Jan. 11, 2010, 10 pages.
"AMXDmax Development History 2002-2014", Omni Medical Systems, Inc., 2 pages.
"Combat Force Multiplier in Flight Bladder Relief Cockpit Essential Equipment Brochure", Omni Medical, 20 pages.
"GSA Price List", Omni Medical, Apr. 2011, 2 pages.
"How is Polypropylene Fiber Made", https:www.yarnsandfibers.com/textile-resources/synthetic-fibers/polypropylene-fiber/polypropylene-fiber-production-raw-materials/how-is-polypropylene-fiber-made/ last accessed 2020, Oct. 7, 2020, 3 pages.
"Letter to Mark Harvie of Omni Measurement Systems", Department of Veterans Affairs, Nov. 1, 2007, 11 pages.
"Revised AMXDmax Advanced Mission Extender Device User & Maintenance Guide", Omni Medical Systems, Oct. 8, 2019, 52 pages.
Merriam-Webster Dictionary,, "Embed Definition & Meaning", https://www.merriam-webster.com/dictionary/embed last accessed Aug. 3, 2023, 2003.
Pieper, et al., "An external urine-collection device for women: A clinical trial", Journal of ER Nursing, vol. 20, No. 2, Mar./Apr. 1993, pp. 51-55.
Vinas, "A Solution for an Awkward—But Serious—Subject", http://www.aero-news.net/index.cfm?do=main.textpost&id=69ae2bb1-838b-4098-a7b5-7flbb2505688 last accessed Feb. 8, 2021.
Wikipedia Article,"Decibel", https://web.archive.org/web/20200415219l7/https://en.wikipedia/org/wiki/Decibel last accessed Mar. 11, 2024, 21 pages.
Wikipedia Article, "Fiberglass", https://web.archive.org.web/20200309194847/https://en.wikipedia.org/wiki/Fiberglass last accessed Mar. 11, 2024.
Wikipedia Article, "Zylinder (Geometrie)", https://de.wikipedia.org/w/index.php?title=Zylinder (Geometrie)&oldid=154862081, version of Jun. 1, 2016, 7 pages.
Advisory Action for U.S. Appl. No. 16/478,180 mailed Jun. 7, 2024.
Advisory Action for U.S. Appl. No. 17/051,585 mailed Oct. 8, 2024.
Advisory Action for U.S. Appl. No. 17/444,792 mailed Jul. 8, 2024.
Advisory Action for U.S. Appl. No. 17/446,256 mailed Nov. 19, 2024.
Advisory Action for U.S. Appl. No. 17/451,345 mailed Jul. 3, 2024.
Advisory Action for U.S. Appl. No. 17/597,673 mailed Jan. 7, 2025.
Advisory Action for U.S. Appl. No. 17/645,821 mailed Jul. 2, 2024.
Advisory Action for U.S. Appl. No. 17/653,137 mailed Nov. 20, 2024.
Advisory Action for U.S. Appl. No. 17/653,920 mailed Oct. 28, 2024.
Advisory Action for U.S. Appl. No. 17/808,354 mailed Jun. 12, 2024.
Advisory Action for U.S. Appl. No. 18/003,029 mailed Jan. 8, 2025.
Advisory Action for U.S. Appl. No. 18/134,857 mailed Oct. 23, 2024.
Advisory Action for U.S. Appl. No. 18/140,163 mailed Jun. 3, 2024.
Advisory Action for U.S. Appl. No. 18/164,800 mailed Jan. 8, 2025.
Corrected Notice of Allowability for U.S. Appl. No. 17/450,864 mailed Oct. 24, 2024.
Corrected Notice of Allowability for U.S. Appl. No. 17/501,591 mailed Aug. 9, 2024.
Corrected Notice of Allowability for U.S. Appl. No. 17/657,474 mailed May 14, 2024.
Corrected Notice of Allowability for U.S. Appl. No. 17/664,914 mailed Aug. 9, 2024.
Corrected Notice of Allowability for U.S. Appl. No. 18/426,795 mailed Dec. 4, 2024.
Final Office Action for U.S. Appl. No. 16/433,773 mailed Sep. 9, 2024.
Final Office Action for U.S. Appl. No. 16/452,258 mailed Jan. 6, 2025.
Final Office Action for U.S. Appl. No. 17/051,585 mailed Jul. 5, 2024.
Final Office Action for U.S. Appl. No. 17/051,600 mailed Jun. 27, 2024.
Final Office Action for U.S. Appl. No. 17/446,256 mailed Aug. 7, 2024.
Final Office Action for U.S. Appl. No. 17/446,654 mailed Dec. 18, 2024.
Final Office Action for U.S. Appl. No. 17/447,123 mailed May 14, 2024.
Final Office Action for U.S. Appl. No. 17/451,354 mailed Oct. 28, 2024.

(56) References Cited

OTHER PUBLICATIONS

Final Office Action for U.S. Appl. No. 17/597,673 mailed Oct. 22, 2024.
Final Office Action for U.S. Appl. No. 17/653,137 mailed Aug. 7, 2024.
Final Office Action for U.S. Appl. No. 17/653,920 mailed Aug. 14, 2024.
Final Office Action for U.S. Appl. No. 17/655,464 mailed Nov. 29, 2024.
Final Office Action for U.S. Appl. No. 17/664,487 mailed Jan. 13, 2025.
Final Office Action for U.S. Appl. No. 18/003,029 mailed Oct. 22, 2024.
Final Office Action for U.S. Appl. No. 18/134,857 mailed Jul. 25, 2024.
Final Office Action for U.S. Appl. No. 18/164,800 mailed Oct. 22, 2024.
Final Office Acton for U.S. Appl. No. 17/595,747 mailed Dec. 12, 2024.
International Search Report and Written Opinion from International Application No. PCT/US2023/030365 mailed Mar. 13, 2024.
International Search Report and Written Opinion from International Application No. PCT/US2023/036238 mailed Jul. 22, 2024.
International Search Report and Written Opinion from International Application No. PCT/US2023/036868 mailed Jun. 5, 2024.
International Search Report and Written Opinion from International Application No. PCT/US2023/075507 mailed Jun. 13, 2024.
International Search Report and Written Opinion from International Application No. PCT/US2023/077168 mailed Jun. 24, 2024.
International Search Report and Written Opinion from International Application No. PCT/US2023/077208 mailed May 10, 2024.
International Search Report and Written Opinion from International Application No. PCT/US2023/080680 mailed Jul. 22, 2024.
International Search Report and Written Opinion from International Application No. PCT/US2023/085516 mailed Aug. 26, 2024.
Issue Notification for U.S. Appl. No. 16/369,676 mailed Oct. 2, 2024.
Issue Notification for U.S. Appl. No. 16/449,039 mailed Jun. 19, 2024.
Issue Notification for U.S. Appl. No. 16/452,145 mailed Oct. 23, 2024.
Issue Notification for U.S. Appl. No. 17/179,116 mailed Dec. 25, 2024.
Issue Notification for U.S. Appl. No. 17/326,980 mailed Jul. 10, 2024.
Issue Notification for U.S. Appl. No. 17/447,123 mailed Nov. 13, 2024.
Issue Notification for U.S. Appl. No. 17/448,811 mailed Jul. 3, 2024.
Issue Notification for U.S. Appl. No. 17/450,864 mailed Jan. 8, 2025.
Issue Notification for U.S. Appl. No. 17/453,260 mailed Jul. 10, 2024.
Issue Notification for U.S. Appl. No. 17/453,560 mailed Aug. 7, 2024.
Issue Notification for U.S. Appl. No. 17/657,474 mailed Jun. 19, 2024.
Issue Notification for U.S. Appl. No. 17/662,700 mailed Oct. 23, 2024.
Issue Notification for U.S. Appl. No. 17/664,914 mailed Nov. 6, 2024.
Issue Notification for U.S. Appl. No. 17/667,097 mailed Dec. 11, 2024.
Issue Notification for U.S. Application No. 18/140, 163 mailed Dec. 4, 2024.
Issue Notification for U.S. Appl. No. 18/198,464 mailed Nov. 20, 2024.
Issue Notification for U.S. Appl. No. 18/389,009 mailed Dec. 18, 2024.
Non-Final Office Action for U.S. Appl. No. 16/452,258 mailed Jun. 20, 2024.
Non-Final Office Action for U.S. Appl. No. 16/478,180 mailed Aug. 7, 2024.
Non-Final Office Action for U.S. Appl. No. 17/378,015 mailed Jul. 5, 2024.
Non-Final Office Action for U.S. Appl. No. 17/444,792 mailed Oct. 30, 2024.
Non-Final Office Action for U.S. Appl. No. 17/446,256 mailed Dec. 13, 2024.
Non-Final Office Action for U.S. Appl. No. 17/446,654 mailed Jun. 25, 2024.
Non-Final Office Action for U.S. Appl. No. 17/450,864 mailed May 29, 2024.
Non-Final Office Action for U.S. Appl. No. 17/451,345 mailed Jul. 25, 2024.
Non-Final Office Action for U.S. Appl. No. 17/595,747 mailed Jun. 7, 2024.
Non-Final Office Action for U.S. Appl. No. 17/597,408 mailed Aug. 15, 2024.
Non-Final Office Action for U.S. Appl. No. 17/614,173 mailed Sep. 24, 2024.
Non-Final Office Action for U.S. Appl. No. 17/625,941 mailed Nov. 4, 2024.
Non-Final Office Action for U.S. Appl. No. 17/628,411 mailed Sep. 23, 2024.
Non-Final Office Action for U.S. Appl. No. 17/645,821 mailed Sep. 6, 2024.
Non-Final Office Action for U.S. Appl. No. 17/653,314 mailed Aug. 29, 2024.
Non-Final Office Action for U.S. Appl. No. 17/653,920 mailed Nov. 27, 2024.
Non-Final Office Action for U.S. Appl. No. 17/661,090 mailed May 22, 2024.
Non-Final Office Action for U.S. Appl. No. 17/663,330 mailed Jul. 1, 2024.
Non-Final Office Action for U.S. Appl. No. 17/664,487 mailed Jun. 17, 2024.
Non-Final Office Action for U.S. Appl. No. 17/749,340 mailed Aug. 14, 2024.
Non-Final Office Action for U.S. Appl. No. 17/757,311 mailed Oct. 22, 2024.
Non-Final Office Action for U.S. Appl. No. 17/758,316 mailed Aug. 28, 2024.
Non-Final Office Action for U.S. Appl. No. 17/759,697 mailed Dec. 4, 2024.
Non-Final Office Action for U.S. Appl. No. 17/808,354 mailed Dec. 13, 2024.
Non-Final Office Action for U.S. Appl. No. 17/907,125 mailed Dec. 13, 2024.
Non-Final Office Action for U.S. Appl. No. 18/139,523 mailed Aug. 26, 2024.
Non-Final Office Action for U.S. Appl. No. 18/140,751 mailed Jun. 21, 2024.
Non-Final Office Action for U.S. Appl. No. 18/389,009 mailed May 24, 2024.
Non-Final Office Action for U.S. Appl. No. 18/426,795 mailed Aug. 9, 2024.
Non-Final Office Action for U.S. Appl. No. 18/451,080 mailed Jul. 30, 2024.
Non-Final Office Action for U.S. Appl. No. 18/584,002 mailed Sep. 19, 2024.
Notice of Allowance for U.S. Appl. No. 16/369,676 mailed Jun. 17, 2024.
Notice of Allowance for U.S. Appl. No. 16/452,145 mailed Jul. 11, 2024.
Notice of Allowance for U.S. Appl. No. 16/478,180 mailed Dec. 16, 2024.
Notice of Allowance for U.S. Appl. No. 16/904,868 mailed Sep. 29, 2024.
Notice of Allowance for U.S. Appl. No. 17/051,585 mailed Dec. 26, 2024.

(56) References Cited

OTHER PUBLICATIONS

Notice of Allowance for U.S. Appl. No. 17/179,116 mailed Sep. 13, 2024.
Notice of Allowance for U.S. Appl. No. 17/447,123 mailed Jul. 26, 2024.
Notice of Allowance for U.S. Appl. No. 17/448,811 mailed Jun. 14, 2024.
Notice of Allowance for U.S. Appl. No. 17/450,864 mailed Sep. 18, 2024.
Notice of Allowance for U.S. Appl. No. 17/501,591 mailed Jul. 31, 2024.
Notice of Allowance for U.S. Appl. No. 17/501,591 mailed Nov. 20, 2024.
Notice of Allowance for U.S. Appl. No. 17/527,769 mailed Nov. 20, 2024.
Notice of Allowance for U.S. Appl. No. 17/646,771 mailed Dec. 17, 2024.
Notice of Allowance for U.S. Appl. No. 17/661,090 mailed Oct. 30, 2024.
Notice of Allowance for U.S. Appl. No. 17/662,700 mailed Jun. 12, 2024.
Notice of Allowance for U.S. Appl. No. 17/663,330 mailed Nov. 20, 2024.
Notice of Allowance for U.S. Appl. No. 17/664,914 mailed Jul. 26, 2024.
Notice of Allowance for U.S. Appl. No. 17/667,097 mailed Aug. 28, 2024.
Notice of Allowance for U.S. Application No. 18/140, 163 mailed Aug. 21, 2024.
Notice of Allowance for U.S. Appl. No. 18/140,751 mailed Nov. 1, 2024.
Notice of Allowance for U.S. Appl. No. 18/198,464 mailed Jul. 30, 2024.
Notice of Allowance for U.S. Appl. No. 18/389,009 mailed Aug. 28, 2024.
Notice of Allowance for U.S. Appl. No. 18/415,080 mailed Dec. 30, 2024.
Notice of Allowance for U.S. Appl. No. 18/426,795 mailed Nov. 20, 2024.
Notice of Allowance for U.S. Appl. No. 18/584,002 mailed Jan. 8, 2025.
Restriction Requirement for U.S. Appl. No. 17/527,769 mailed Jun. 17, 2024.
Restriction Requirement for U.S. Appl. No. 17/596,629 mailed Sep. 19, 2024.
Restriction Requirement for U.S. Appl. No. 17/625,941 mailed Aug. 7, 2024.
Restriction Requirement for U.S. Appl. No. 17/756,201 mailed Oct. 4, 2024.
Restriction Requirement for U.S. Application No. 17/758, 152 mailed Nov. 5, 2024.
Restriction Requirement for U.S. Appl. No. 17/809,083 mailed Dec. 31, 2024.
Restriction Requirement for U.S. Appl. No. 17/878,268 mailed Sep. 20, 2024.
U.S. Appl. No. 17/013,822, filed Sep. 7, 2020.
U.S. Appl. No. 18/662,216, filed May 13, 2024.
U.S. Appl. No. 18/728,604, filed Jul. 12, 2024.
U.S. Appl. No. 18/757,964, filed Jun. 28, 2024.
U.S. Appl. No. 18/758,025, filed Jun. 28, 2024.
U.S. Appl. No. 18/828,559, filed Sep. 9, 2024.
U.S. Appl. No. 18/834,115, filed Jul. 29, 2024.
U.S. Appl. No. 18/834,176, filed Jul. 29, 2024.
U.S. Appl. No. 18/834,340, filed Jul. 30, 2024.
U.S. Appl. No. 18/835,068, filed Aug. 1, 2024.
U.S. Appl. No. 18/835,444, filed Aug. 2, 2024.
U.S. Appl. No. 18/836,204, filed Aug. 6, 2024.
U.S. Appl. No. 18/841,630, filed Aug. 26, 2024.
U.S. Appl. No. 18/851,197, filed Sep. 26, 2024.
U.S. Appl. No. 18/886,306, filed Sep. 16, 2024.
U.S. Appl. No. 18/903,592, filed Oct. 1, 2024.
U.S. Appl. No. 18/925,921, filed Oct. 24, 2024.
U.S. Appl. No. 18/930,014, filed Oct. 29, 2024.
U.S. Appl. No. 18/931,853, filed Oct. 30, 2024.
U.S. Appl. No. 18/951,944, filed Nov. 19, 2024.
U.S. Appl. No. 18/957,011, filed Nov. 22, 2024.
U.S. Appl. No. 18/974,367, filed Dec. 9, 2024.
U.S. Appl. No. 18/982,930, filed Dec. 16, 2024.
U.S. Appl. No. 63/564,696, filed Mar. 13, 2024.
U.S. Appl. No. 63/568,615, filed Mar. 22, 2024.
U.S. Appl. No. 63/683,428, filed Aug. 15, 2024.
U.S. Appl. No. 63/711,438, filed Oct. 24, 2024.
U.S. Appl. No. 63/711,445, filed Oct. 24, 2024.
U.S. Appl. No. 63/720,004, filed Nov. 13, 2024.
"Dictionary.com, ABUT Definition and Meaning", Dictionary.com, https://www.dictionary.com/browse/abut, 2024, 1 page.
"Oblong", Cambridge Dictionary, https://dictionary.cambridge.org/dictionary/english/oblong, 2024, 1 page.
Britannica, "Polyolefin", Britannica Online Encyclopedia, T. Editors of Encyclopaedia, https://www.britannica.com/science/polyolefin, Jul. 26, 2012.
Martin, et al., "Chapter 5 Applications of Polyethylene Oxide (POLYOX) in Hydrophilic Matrices", Hydrophilic Matrix Tablets for Oral Controlled Release, AAPS Advances in the Pharmaceutical Sciences vol. 16, 2014, pp. 123-141.
"Proximate Definition & Meaning" <https://www.merriam-webster.com/dictionary/> 2025.
"Surface Energy Data for Cellulose acetate, CAS # 9004-35-7", Diviersified Enterprises, 2009, 1 page.
"Tube Definition & Meaning" Merriam Webster Dictionary, 2025, <https://www.merriam-webster.com/dictionary/tube>.
Advisory Action for U.S. Appl. No. 16/452,258 mailed Apr. 17, 2026.
Advisory Action for U.S. Appl. No. 16/452,258 mailed May 5, 2025.
Advisory Action for U.S. Appl. No. 17/378,015 mailed Oct. 28, 2025.
Advisory Action for U.S. Appl. No. 17/394,055 mailed Jan. 9, 2026.
Advisory Action for U.S. Appl. No. 17/446,256 mailed Nov. 6, 2025.
Advisory Action for U.S. Appl. No. 17/446,654 mailed Apr. 16, 2026.
Advisory Action for U.S. Appl. No. 17/446,654 mailed Feb. 28, 2025.
Advisory Action for U.S. Appl. No. 17/451,345 mailed May 13, 2025.
Advisory Action for U.S. Appl. No. 17/595,747 mailed Mar. 17, 2025.
Advisory Action for U.S. Appl. No. 17/653,314 mailed Apr. 8, 2025.
Advisory Action for U.S. Appl. No. 17/655,464 mailed Feb. 25, 2025.
Advisory Action for U.S. Appl. No. 17/664,487 mailed Apr. 24, 2025.
Advisory Action for U.S. Appl. No. 17/664,487 mailed Apr. 9, 2026.
Advisory Action for U.S. Appl. No. 17/757,311 mailed Jul. 2, 2025.
Advisory Action for U.S. Appl. No. 17/929,887 mailed Apr. 16, 2026.
Advisory Action for U.S. Appl. No. 18/042,842 mailed Apr. 14, 2026.
Advisory Action for U.S. Appl. No. 18/164,800 mailed Apr. 9, 2026.
Advisory Action for U.S. Appl. No. 18/247,986 mailed Apr. 1, 2026.
Advisory Action for U.S. Appl. No. 18/265,736 mailed Mar. 4, 2026.
Corrected Notice of Allowability for U.S. Appl. No. 17/444,792 mailed Jun. 24, 2025.
Corrected Notice of Allowability for U.S. Appl. No. 17/646,771 mailed Jan. 17, 2025.
Corrected Notice of Allowability for U.S. Appl. No. 17/653,314 mailed Oct. 29, 2025.
Corrected Notice of Allowability for U.S. Appl. No. 17/808,354 mailed Nov. 25, 2025.
Corrected Notice of Allowability for U.S. Appl. No. 17/996,253 mailed Apr. 28, 2025.

(56) References Cited

OTHER PUBLICATIONS

Corrected Notice of Allowability for U.S. Application No. 18/041,109 mailed Apr. 2, 2026.
Corrected Notice of Allowability for U.S. Appl. No. 18/134,857 mailed Mar. 14, 2025.
Corrected Notice of Allowability for U.S. Appl. No. 18/249,577 mailed Apr. 15, 2026.
Corrected Notice of Allowability for U.S. Application No. 18/260,122 mailed Aug. 11, 2025.
Corrected Notice of Allowability for U.S. Appl. No. 18/264,004 mailed Feb. 10, 2026.
Corrected Notice of Allowability for U.S. Appl. No. 18/264,004 mailed Feb. 3, 2026.
Corrected Notice of Allowability for U.S. Appl. No. 18/294,370 mailed Mar. 31, 2026.
Di Mauro, et al., "Penile length and circumference dimensions: A large study in young Italian men" Reconstructive Urology, Men's Health Working Parties of the European Association of Urology (EAU) Young Academic Urologists (YAU). pp. 1-7, Mar. 8, 2021.
Final Office Action for U.S. Appl. No. 16/452,258 mailed Feb. 11, 2026.
Final Office Action for U.S. Appl. No. 17/051,600 mailed Aug. 6, 2025.
Final Office Action for U.S. Appl. No. 17/378,015 mailed Jun. 18, 2025.
Final Office Action for U.S. Appl. No. 17/394,055 mailed Sep. 24, 2025.
Final Office Action for U.S. Appl. No. 17/446,256 mailed Jun. 11, 2025.
Final Office Action for U.S. Appl. No. 17/446,654 mailed Dec. 22, 2025.
Final Office Action for U.S. Appl. No. 17/451,345 mailed Feb. 6, 2025.
Final Office Action for U.S. Appl. No. 17/595,747 mailed Feb. 19, 2026.
Final Office Action for U.S. Appl. No. 17/597,408 mailed Mar. 24, 2025.
Final Office Action for U.S. Appl. No. 17/614,173 mailed May 20, 2025.
Final Office Action for U.S. Appl. No. 17/625,941 mailed Feb. 18, 2025.
Final Office Action for U.S. Appl. No. 17/628,411 mailed Apr. 30, 2025.
Final Office Action for U.S. Appl. No. 17/628,411 mailed Apr. 7, 2026.
Final Office Action for U.S. Appl. No. 17/631,619 mailed Oct. 1, 2025.
Final Office Action for U.S. Appl. No. 17/653,137 mailed Jun. 25, 2025.
Final Office Action for U.S. Appl. No. 17/653,314 mailed Jan. 30, 2025.
Final Office Action for U.S. Appl. No. 17/653,920 mailed Apr. 24, 2025.
Final Office Action for U.S. Appl. No. 17/655,464 mailed Feb. 17, 2026.
Final Office Action for U.S. Appl. No. 17/664,487 mailed Jan. 5, 2026.
Final Office Action for U.S. Appl. No. 17/756,201 mailed Dec. 30, 2025.
Final Office Action for U.S. Appl. No. 17/757,311 mailed Mar. 31, 2025.
Final Office Action for U.S. Appl. No. 17/758,152 mailed Apr. 7, 2026.
Final Office Action for U.S. Appl. No. 17/759,697 mailed Jun. 4, 2025.
Final Office Action for U.S. Appl. No. 17/808,354 mailed Jun. 13, 2025.
Final Office Action for U.S. Appl. No. 17/809,083 mailed Jan. 23, 2026.
Final Office Action for U.S. Appl. No. 17/907,125 mailed Apr. 30, 2025.
Final Office Action for U.S. Appl. No. 17/929,887, filed Jan. 13, 2026.
Final Office Action for U.S. Appl. No. 17/933,590 mailed Feb. 19, 2026.
Final Office Action for U.S. Appl. No. 18/003,029 mailed Nov. 26, 2025.
Final Office Action for U.S. Appl. No. 18/006,807 mailed Dec. 23, 2025.
Final Office Action for U.S. Appl. No. 18/042,842 mailed Jan. 27, 2026.
Final Office Action for U.S. Appl. No. 18/043,618 mailed Nov. 26, 2025.
Final Office Action for U.S. Appl. No. 18/139,523 mailed May 8, 2025.
Final Office Action for U.S. Appl. No. 18/150,360 mailed Apr. 10, 2026.
Final Office Action for U.S. Appl. No. 18/164,800 mailed Dec. 5, 2025.
Final Office Action for U.S. Appl. No. 18/247,986 mailed Jan. 7, 2026.
Final Office Action for U.S. Appl. No. 18/254,638 mailed Apr. 8, 2026.
Final Office Action for U.S. Appl. No. 18/265,736 mailed Dec. 1, 2025.
Final Office Action for U.S. Appl. No. 18/548,152 mailed Apr. 15, 2026.
Foamtech, "Foam Packaging Isnert: Best Selection Guide", https://web/archive.org/web/20170922162235/http://www.foamtechchina/com:80/foam-packaging-insert/, Sep. 22, 2017, 25 pages.
International Search Report and Written Opinion from International Application No. PCT/US2023/031432 mailed Feb. 29, 2024.
International Search Report and Written Opinion from International Application No. PCT/US2023/036875 mailed May 31, 2024.
International Search Report and Written Opinion from International Application No. PCT/US2023/077205 mailed Jul. 19, 2024.
International Search Report and Written Opinion from International Application No. PCT/US2024/053681 mailed Jan. 27, 2025.
International Search Report and Written Opinion from International Application No. PCT/US2024/058598 mailed Mar. 28, 2025.
International Search Report and Written Opinion from International Application No. PCT/US2025/018907 mailed May 16, 2025.
International Search Report and Written Opinion from International Application No. PCT/US2025/018909 mailed May 20, 2025.
International Search Report and Written Opinion from International Application No. PCT/US2025/018913 mailed Jun. 18, 2025.
Issue Notification for U.S. Appl. No. 16/433,773 mailed Jan. 21, 2026.
Issue Notification for U.S. Appl. No. 16/478,180 mailed Mar. 5, 2025.
Issue Notification for U.S. Appl. No. 16/904,868 mailed Apr. 30, 2025.
Issue Notification for U.S. Appl. No. 17/051,399 mailed Mar. 4, 2026.
Issue Notification for U.S. Appl. No. 17/051,585 mailed Mar. 26, 2025.
Issue Notification for U.S. Appl. No. 17/444,792 mailed Jun. 25, 2025.
Issue Notification for U.S. Appl. No. 17/451,354 mailed Feb. 25, 2026.
Issue Notification for U.S. Appl. No. 17/501,591 mailed Mar. 5, 2025.
Issue Notification for U.S. Appl. No. 17/529,769 mailed Feb. 19, 2025.
Issue Notification for U.S. Appl. No. 17/597,673 mailed Jun. 4, 2025.
Issue Notification for U.S. Appl. No. 17/625,941 mailed Feb. 25, 2026.
Issue Notification for U.S. Appl. No. 17/645,821 mailed Apr. 1, 2026.
Issue Notification for U.S. Appl. No. 17/646,771 mailed Mar. 19, 2025.

(56) References Cited

OTHER PUBLICATIONS

Issue Notification for U.S. Appl. No. 17/653,137 mailed Feb. 4, 2025.
Issue Notification for U.S. Appl. No. 17/653,314 mailed Feb. 11, 2026.
Issue Notification for U.S. Appl. No. 17/653,920 mailed Oct. 22, 2025.
Issue Notification for U.S. Appl. No. 17/661,090 mailed Feb. 5, 2025.
Issue Notification for U.S. Appl. No. 17/663,330 mailed Feb. 26, 2025.
Issue Notification for U.S. Appl. No. 17/749,340 mailed May 28, 2025.
Issue Notification for U.S. Appl. No. 17/755,236 mailed Oct. 29, 2025.
Issue Notification for U.S. Appl. No. 17/758,316 mailed Jun. 25, 2025.
Issue Notification for U.S. Appl. No. 17/808,354 mailed Mar. 4, 2026.
Issue Notification for U.S. Appl. No. 17/878,268 mailed Feb. 4, 2026.
Issue Notification for U.S. Appl. No. 17/907,125 mailed Dec. 30, 2025.
Issue Notification for U.S. Appl. No. 17/912,147 mailed Mar. 18, 2026.
Issue Notification for U.S. Appl. No. 17/996,064 mailed Nov. 5, 2025.
Issue Notification for U.S. Appl. No. 17/996,155 mailed Oct. 8, 2025.
Issue Notification for U.S. Appl. No. 17/996,253 mailed Oct. 29, 2025.
Issue Notification for U.S. Appl. No. 17/996,468 mailed Nov. 26, 2025.
Issue Notification for U.S. Appl. No. 18/007,105 mailed Oct. 1, 2025.
Issue Notification for U.S. Appl. No. 18/044,413 mailed Dec. 30, 2025.
Issue Notification for U.S. Appl. No. 18/134,857 mailed May 28, 2025.
Issue Notification for U.S. Appl. No. 18/140,751 mailed Feb. 12, 2025.
Issue Notification for U.S. Appl. No. 18/260,122 mailed Nov. 12, 2025.
Issue Notification for U.S. Appl. No. 18/415,080 mailed Apr. 9, 2025.
Issue Notification for U.S. Appl. No. 18/426,795 mailed Feb. 19, 2025.
Issue Notification for U.S. Appl. No. 18/584,002 mailed Apr. 16, 2025.
Non-Final Office Action for U.S. Appl. No. 16/433,773 mailed Feb. 28, 2025.
Non-Final Office Action for U.S. Appl. No. 16/452,258 mailed Sep. 24, 2025.
Non-Final Office Action for U.S. Appl. No. 17/051,600 mailed Feb. 28, 2025.
Non-Final Office Action for U.S. Appl. No. 17/378,015 mailed Dec. 12, 2025.
Non-Final Office Action for U.S. Appl. No. 17/394,055 mailed Mar. 13, 2025.
Non-Final Office Action for U.S. Appl. No. 17/394,055 mailed Mar. 19, 2025.
Non-Final Office Action for U.S. Appl. No. 17/446,256 mailed Dec. 2, 2025.
Non-Final Office Action for U.S. Appl. No. 17/446,654 mailed May 1, 2025.
Non-Final Office Action for U.S. Appl. No. 17/451,354 mailed Mar. 19, 2025.
Non-Final Office Action for U.S. Appl. No. 17/595,747 mailed Jun. 12, 2025.
Non-Final Office Action for U.S. Appl. No. 17/597,408 mailed Apr. 7, 2026.
Non-Final Office Action for U.S. Appl. No. 17/614,173 mailed Dec. 29, 2025.
Non-Final Office Action for U.S. Appl. No. 17/628,411 mailed Dec. 22, 2025.
Non-Final Office Action for U.S. Appl. No. 17/631,619 mailed Mar. 19, 2025.
Non-Final Office Action for U.S. Appl. No. 17/635,866 mailed Jul. 29, 2025.
Non-Final Office Action for U.S. Appl. No. 17/645,821 mailed Mar. 31, 2025.
Non-Final Office Action for U.S. Appl. No. 17/653,137 mailed Jan. 28, 2025.
Non-Final Office Action for U.S. Appl. No. 17/653,314 mailed May 8, 2025.
Non-Final Office Action for U.S. Appl. No. 17/655,464 mailed Mar. 20, 2025.
Non-Final Office Action for U.S. Appl. No. 17/664,487 mailed May 19, 2025.
Non-Final Office Action for U.S. Appl. No. 17/756,201 mailed Apr. 24, 2025.
Non-Final Office Action for U.S. Appl. No. 17/757,311 mailed Sep. 2, 2025.
Non-Final Office Action for U.S. Appl. No. 17/758,152 mailed Apr. 8, 2025.
Non-Final Office Action for U.S. Appl. No. 17/759,587 mailed Jan. 26, 2026.
Non-Final Office Action for U.S. Appl. No. 17/759,697 mailed Sep. 17, 2025.
Non-Final Office Action for U.S. Appl. No. 17/809,083 mailed Apr. 2, 2025.
Non-Final Office Action for U.S. Appl. No. 17/809,083 mailed Mar. 7, 2025.
Non-Final Office Action for U.S. Appl. No. 17/878,268 mailed Mar. 17, 2025.
Non-Final Office Action for U.S. Appl. No. 17/912,147 mailed May 29, 2025.
Non-Final Office Action for U.S. Appl. No. 17/929,887 mailed Jun. 25, 2025.
Non-Final Office Action for U.S. Appl. No. 17/930,238 mailed Jun. 30, 2025.
Non-Final Office Action for U.S. Appl. No. 17/933,590 mailed Jul. 29, 2025.
Non-Final Office Action for U.S. Appl. No. 17/996,064 mailed Mar. 6, 2025.
Non-Final Office Action for U.S. Appl. No. 17/996,556 mailed Dec. 22, 2025.
Non-Final Office Action for U.S. Appl. No. 18/003,029 mailed Apr. 18, 2025.
Non-Final Office Action for U.S. Appl. No. 18/003,029 mailed Apr. 20, 2026.
Non-Final Office Action for U.S. Appl. No. 18/006,807 mailed May 29, 2025.
Non-Final Office Action for U.S. Appl. No. 18/034,902 mailed Mar. 20, 2026.
Non-Final Office Action for U.S. Appl. No. 18/042,842 mailed May 22, 2025.
Non-Final Office Action for U.S. Appl. No. 18/043,618 mailed May 19, 2025.
Non-Final Office Action for U.S. Appl. No. 18/043,807 mailed Feb. 10, 2026.
Non-Final Office Action for U.S. Appl. No. 18/115,444 mailed Oct. 22, 2025.
Non-Final Office Action for U.S. Appl. No. 18/139,523 mailed Nov. 19, 2025.
Non-Final Office Action for U.S. Appl. No. 18/150,360 mailed Nov. 5, 2025.
Non-Final Office Action for U.S. Appl. No. 18/164,800 mailed Apr. 25, 2025.
Non-Final Office Action for U.S. Appl. No. 18/246,121 mailed Jan. 22, 2026.

(56) References Cited

OTHER PUBLICATIONS

Non-Final Office Action for U.S. Appl. No. 18/247,986 mailed Jun. 4, 2025.
Non-Final Office Action for U.S. Appl. No. 18/249,577 mailed Nov. 17, 2025.
Non-Final Office Action for U.S. Appl. No. 18/254,638 mailed Nov. 17, 2025.
Non-Final Office Action for U.S. Appl. No. 18/259,626 mailed Jan. 30, 2026.
Non-Final Office Action for U.S. Appl. No. 18/259,626 mailed Jul. 11, 2025.
Non-Final Office Action for U.S. Appl. No. 18/260,394, filed Jan. 13, 2026.
Non-Final Office Action for U.S. Appl. No. 18/263,800 mailed Feb. 5, 2026.
Non-Final Office Action for U.S. Appl. No. 18/264,004 mailed May 15, 2025.
Non-Final Office Action for U.S. Appl. No. 18/264,278 mailed Nov. 10, 2025.
Non-Final Office Action for U.S. Appl. No. 18/265,736 mailed Jul. 1, 2025.
Non-Final Office Action for U.S. Appl. No. 18/376,274 mailed Mar. 9, 2026.
Non-Final Office Action for U.S. Appl. No. 18/546,465 mailed Apr. 1, 2026.
Non-Final Office Action for U.S. Appl. No. 18/548,152 mailed Sep. 16, 2025.
Non-Final Office Action for U.S. Appl. No. 18/549,387 mailed Mar. 4, 2026.
Non-Final Office Action for U.S. Appl. No. 18/551,492 mailed Mar. 19, 2026.
Non-Final Office Action for U.S. Appl. No. 18/553,625 mailed Oct. 2, 2025.
Non-Final Office Action for U.S. Appl. No. 18/556,945 mailed Dec. 19, 2025.
Non-Final Office Action for U.S. Appl. No. 18/562,626 mailed Feb. 11, 2026.
Non-Final Office Action for U.S. Appl. No. 18/563,672 mailed Feb. 12, 2026.
Non-Final Office Action for U.S. Appl. No. 18/569,711 mailed Mar. 30, 2026.
Non-Final Office Action for U.S. Appl. No. 18/662,216 mailed Mar. 9, 2026.
Non-Final Office Action for U.S. Appl. No. 18/681,987 mailed Mar. 30, 2026.
Non-Final Office Action for U.S. Appl. No. 18/682,006 mailed Mar. 4, 2026.
Non-Final Office Action for U.S. Appl. No. 18/689,532 mailed Mar. 19, 2026.
Non-Final Office Action for U.S. Appl. No. 18/690,392 mailed Feb. 9, 2026.
Non-Final Office Action for U.S. Appl. No. 18/694,090 mailed Mar. 17, 2026.
Non-Final Office Action for U.S. Appl. No. 18/757,964 mailed Aug. 20, 2025.
Non-Final Office Action for U.S. Appl. No. 18/757,964 mailed Mar. 27, 2026.
Non-Final Office Action for U.S. Appl. No. 19/237,368 mailed Apr. 6, 2026.
Non-Final Office Action for U.S. Appl. No. 29/892,478 mailed Mar. 12, 2026.
Notice of Allowance for U.S. Appl. No. 16/433,773 mailed Oct. 10, 2025.
Notice of Allowance for U.S. Appl. No. 16/904,868 mailed Jan. 21, 2025.
Notice of Allowance for U.S. Appl. No. 17/051,399 mailed Nov. 17, 2025.
Notice of Allowance for U.S. Appl. No. 17/051,600 mailed Jan. 5, 2026.
Notice of Allowance for U.S. Appl. No. 17/394,055 mailed Mar. 20, 2026.
Notice of Allowance for U.S. Appl. No. 17/444,792 mailed Mar. 28, 2025.
Notice of Allowance for U.S. Appl. No. 17/451,345 mailed Jun. 24, 2025.
Notice of Allowance for U.S. Appl. No. 17/451,354 mailed Nov. 18, 2025.
Notice of Allowance for U.S. Appl. No. 17/596,629 mailed Jan. 29, 2025.
Notice of Allowance for U.S. Appl. No. 17/596,629 mailed May 27, 2025.
Notice of Allowance for U.S. Appl. No. 17/597,673 mailed Feb. 26, 2025.
Notice of Allowance for U.S. Appl. No. 17/625,887 mailed Mar. 3, 2026.
Notice of Allowance for U.S. Appl. No. 17/625,941 mailed Nov. 13, 2025.
Notice of Allowance for U.S. Appl. No. 17/635,866 mailed Mar. 2, 2026.
Notice of Allowance for U.S. Appl. No. 17/645,821 mailed Nov. 24, 2025.
Notice of Allowance for U.S. Appl. No. 17/653,137 mailed Oct. 22, 2025.
Notice of Allowance for U.S. Appl. No. 17/653,314 mailed Oct. 20, 2025.
Notice of Allowance for U.S. Appl. No. 17/653,920 mailed Jul. 9, 2025.
Notice of Allowance for U.S. Appl. No. 17/749,340 mailed Feb. 14, 2025.
Notice of Allowance for U.S. Appl. No. 17/755,236 mailed Jul. 17, 2025.
Notice of Allowance for U.S. Appl. No. 17/758,316 mailed Mar. 24, 2025.
Notice of Allowance for U.S. Appl. No. 17/759,697 mailed Jan. 30, 2026.
Notice of Allowance for U.S. Appl. No. 17/808,354 mailed Nov. 12, 2025.
Notice of Allowance for U.S. Appl. No. 17/878,268 mailed Oct. 15, 2025.
Notice of Allowance for U.S. Appl. No. 17/907,125 mailed Sep. 26, 2025.
Notice of Allowance for U.S. Appl. No. 17/912,147 mailed Dec. 3, 2025.
Notice of Allowance for U.S. Appl. No. 17/930,238 mailed Dec. 16, 2025.
Notice of Allowance for U.S. Appl. No. 17/996,064 mailed Jul. 29, 2025.
Notice of Allowance for U.S. Appl. No. 17/996,155 mailed Jun. 24, 2025.
Notice of Allowance for U.S. Appl. No. 17/996,155 mailed Mar. 11, 2025.
Notice of Allowance for U.S. Appl. No. 17/996,253 mailed Apr. 11, 2025.
Notice of Allowance for U.S. Appl. No. 17/996,253 mailed Jul. 11, 2025.
Notice of Allowance for U.S. Appl. No. 17/996,468 mailed Apr. 14, 2025.
Notice of Allowance for U.S. Appl. No. 17/996,468 mailed Jul. 15, 2025.
Notice of Allowance for U.S. Appl. No. 18/007,105 mailed Jun. 17, 2025.
Notice of Allowance for U.S. Appl. No. 18/041,109 mailed Mar. 25, 2026.
Notice of Allowance for U.S. Appl. No. 18/044,413 mailed Sep. 16, 2025.
Notice of Allowance for U.S. Appl. No. 18/134,857 mailed Feb. 20, 2025.
Notice of Allowance for U.S. Appl. No. 18/249,577 mailed Mar. 31, 2026.
Notice of Allowance for U.S. Appl. No. 18/260,122 mailed Jul. 30, 2025.

(56) References Cited

OTHER PUBLICATIONS

Notice of Allowance for U.S. Appl. No. 18/264,004 mailed Jan. 30, 2026.
Notice of Allowance for U.S. Appl. No. 18/294,370 mailed Mar. 17, 2026.
Notice of Allowance for U.S. Appl. No. 18/553,625 mailed Apr. 15, 2026.
Notice of Allowance for U.S. Appl. No. 18/610,523 mailed Mar. 4, 2026.
Restriction Requirement for U.S. Appl. No. 17/625,887 mailed Sep. 2, 2025.
Restriction Requirement for U.S. Appl. No. 17/755,236 mailed Apr. 24, 2025.
Restriction Requirement for U.S. Appl. No. 17/929,887 mailed Mar. 10, 2025.
Restriction Requirement for U.S. Appl. No. 17/930,238 mailed Apr. 17, 2025.
Restriction Requirement for U.S. Appl. No. 17/996,556 mailed Aug. 11, 2025.
Restriction Requirement for U.S. Appl. No. 18/034,902 mailed Nov. 6, 2025.
Restriction Requirement for U.S. Appl. No. 18/041,109 mailed Jun. 4, 2025.
Restriction Requirement for U.S. Appl. No. 18/041,109 mailed Oct. 23, 2025.
Restriction Requirement for U.S. Appl. No. 18/150,360 mailed May 19, 2025.
Restriction Requirement for U.S. Appl. No. 18/246,121 mailed Jul. 25, 2025.
Restriction Requirement for U.S. Appl. No. 18/249,577 mailed Aug. 25, 2025.
Restriction Requirement for U.S. Appl. No. 18/254,638 mailed Jul. 21, 2025.
Restriction Requirement for U.S. Appl. No. 18/260,394 mailed Jul. 25, 2025.
Restriction Requirement for U.S. Appl. No. 18/294,370 mailed Nov. 26, 2025.
Restriction Requirement for U.S. Appl. No. 18/294,403 mailed Jan. 27, 2026.
Restriction Requirement for U.S. Appl. No. 18/335,579 mailed Nov. 26, 2025.
Restriction Requirement for U.S. Appl. No. 18/373,424 mailed Nov. 14, 2025.
Restriction Requirement for U.S. Appl. No. 18/376,274 mailed Dec. 10, 2025.
Restriction Requirement for U.S. Appl. No. 18/549,387 mailed Dec. 9, 2025.
Restriction Requirement for U.S. Appl. No. 18/551,492 mailed Nov. 10, 2025.
Restriction Requirement for U.S. Appl. No. 18/558,502 mailed Jan. 29, 2026.
Restriction Requirement for U.S. Appl. No. 18/569,711 mailed Jan. 6, 2026.
Restriction Requirement for U.S. Appl. No. 18/569,778 mailed Jan. 15, 2026.
Restriction Requirement for U.S. Appl. No. 18/662,216 mailed Nov. 26, 2025.
Restriction Requirement for U.S. Appl. No. 18/687,117 mailed Mar. 26, 2026.
Restriction Requirement for U.S. Appl. No. 19/237,368 mailed Dec. 18, 2025.
Supplemental Notice of Allowance for U.S. Appl. No. 17/597,673 mailed Apr. 10, 2025.
U.S. Appl. No. 17/051,399, filed Oct. 28, 2020.
U.S. Appl. No. 17/596,629, filed Dec. 15, 2021.
U.S. Appl. No. 17/625,941, filed Jan. 10, 2022.
U.S. Appl. No. 18/034,902, filed May 2, 2023.
U.S. Appl. No. 18/546,465, filed Aug. 15, 2023.
U.S. Appl. No. 19/038,774, filed Jan. 28, 2025.
U.S. Appl. No. 19/039,165 filed Jan. 28, 2025.
U.S. Appl. No. 19/046,047, filed Feb. 5, 2025.
U.S. Appl. No. 19/047,728, filed Feb. 7, 2025.
U.S. Appl. No. 19/048,004, filed Feb. 7, 2025.
U.S. Appl. No. 19/049,501, filed Feb. 10, 2025.
U.S. Appl. No. 19/049,783, filed Feb. 10, 2025.
U.S. Appl. No. 19/058,726, filed Feb. 20, 2025.
U.S. Appl. No. 19/069,480, filed Mar. 4, 2025.
U.S. Appl. No. 19/078,602, filed Mar. 13, 2025.
U.S. Appl. No. 19/092,262, filed Mar. 27, 2025.
U.S. Appl. No. 19/103,165 filed Feb. 11, 2025.
U.S. Appl. No. 19/110,938, filed Mar. 12, 2025.
U.S. Appl. No. 19/111,921, filed Mar. 14, 2025.
U.S. Appl. No. 19/127,234, filed May 5, 2025.
U.S. Appl. No. 19/171,983, filed Apr. 7, 2025.
U.S. Appl. No. 19/179,540, filed Apr. 15, 2025.
U.S. Appl. No. 19/202,862, filed May 8, 2025.
U.S. Appl. No. 19/207,699, filed May 14, 2025.
U.S. Appl. No. 19/215,723, filed May 22, 2025.
U.S. Appl. No. 19/237,368, filed Jun. 13, 2025.
U.S. Appl. No. 19/240,380, filed Jun. 17, 2025.
U.S. Appl. No. 19/329,723, filed Sep. 16, 2025.
U.S. Appl. No. 19/337,217, filed Sep. 23, 2025.
U.S. Appl. No. 19/353,151 filed Oct. 8, 2025.
U.S. Appl. No. 19/356,506, filed Oct. 13, 2025.
U.S. Appl. No. 19/358,647, filed Oct. 15, 2025.
U.S. Appl. No. 19/370,361, filed Oct. 27, 2025.
U.S. Appl. No. 19/418,150 filed Dec. 12, 2025.
U.S. Appl. No. 19/443,729, filed Jan. 8, 2026.
U.S. Appl. No. 19/447,347, filed Jan. 13, 2026.
U.S. Appl. No. 19/451,614, filed Jan. 16, 2026.
U.S. Appl. No. 19/491,481, filed Dec. 9, 2025.
U.S. Appl. No. 19/494,631, filed Dec. 18, 2025.
U.S. Appl. No. 19/510,850, filed Feb. 12, 2026.
U.S. Appl. No. 19/513,755, filed Feb. 24, 2026.
U.S. Appl. No. 19/513,838, filed Feb. 24, 2026.
U.S. Appl. No. 19/514,100 filed Feb. 25, 2026.
U.S. Appl. No. 19/534,156 filed Feb. 9, 2026.
U.S. Appl. No. 19/535,649, filed Feb. 10, 2026.
U.S. Appl. No. 19/539,961, filed Feb. 13, 2026.
U.S. Appl. No. 19/541,655, filed Feb. 17, 2026.
U.S. Appl. No. 19/544,501, filed Feb. 19, 2026.
U.S. Appl. No. 19/554,125 filed Mar. 2, 2026.
U.S. Appl. No. 19/579,050, filed Apr. 16, 2026.
U.S. Appl. No. 19/638,741, filed Apr. 3, 2026.
U.S. Appl. No. 62/665,711, filed May 2, 2018.
U.S. Appl. No. 63/181,709, filed Apr. 29, 2021.
Advisory Action for U.S. Appl. No. 14/722,613 mailed Mar. 4, 2019.
Advisory Action for U.S. Appl. No. 14/952,591 mailed Jun. 1, 2018.
Advisory Action for U.S. Appl. No. 15/238,427 mailed Apr. 10, 2019.
Advisory Action for U.S. Appl. No. 16/899,956 mailed Jul. 9, 2021.
Advisory Action for U.S. Appl. No. 16/904,868 mailed Jul. 2, 2021.
Advisory Action for U.S. Appl. No. 16/905,400 mailed Feb. 16, 2022.
Advisory Action for U.S. Appl. No. 16/905,400 mailed Jun. 9, 2021.
Corrected International Search Report and Written Opinion for International Application No. PCT/US2017/043025 mailed Jan. 11, 2018.
Corrected Notice of Allowability for U.S. Appl. No. 15/221,106 mailed Jul. 2, 2019.
Corrected Notice of Allowability for U.S. Appl. No. 15/612,325 mailed Mar. 17, 2021.
Corrected Notice of Allowability for U.S. Appl. No. 17/330,657 mailed Dec. 9, 2021.
Final Office Action for U.S. Appl. No. 14/722,613 mailed on Nov. 29, 2018.
Final Office Action for U.S. Appl. No. 14/947,759 mailed Apr. 8, 2016.
Final Office Action for U.S. Appl. No. 14/952,591 mailed Feb. 23, 2018.
Final Office Action for U.S. Appl. No. 14/952,591 mailed Nov. 1, 2019.

(56) References Cited

OTHER PUBLICATIONS

Final Office Action for U.S. Appl. No. 14/952,591 mailed Nov. 27, 2020.
Final Office Action for U.S. Appl. No. 15/171,968 mailed Feb. 14, 2020.
Final Office Action for U.S. Appl. No. 15/171,968 mailed Mar. 19, 2019.
Final Office Action for U.S. Appl. No. 15/221,106 mailed Jan. 23, 2019.
Final Office Action for U.S. Appl. No. 15/238,427 mailed Jan. 2, 2019.
Final Office Action for U.S. Appl. No. 15/260,103 mailed Feb. 14, 2019.
Final Office Action for U.S. Appl. No. 15/612,325 mailed Sep. 17, 2020.
Final Office Action for U.S. Appl. No. 16/452,145 mailed Mar. 25, 2022.
Final Office Action for U.S. Appl. No. 16/899,956 mailed Apr. 19, 2021.
Final Office Action for U.S. Appl. No. 16/904,868 mailed Mar. 10, 2022.
Final Office Action for U.S. Appl. No. 16/904,868 mailed Mar. 26, 2021.
Final Office Action for U.S. Appl. No. 16/905,400 mailed Apr. 6, 2021.
Final Office Action for U.S. Appl. No. 16/905,400 mailed Dec. 9, 2021.
Final Office Action for U.S. Appl. No. 17/088,272 mailed May 25, 2021.
Final Office Action for U.S. Appl. No. 29/624,661 mailed Feb. 18, 2020.
International Search Report and Written Opinion from International Application No. PCT/US2016/049274 mailed Dec. 1, 2016.
International Search Report and Written Opinion from International Application No. PCT/US2017/035625 mailed Aug. 15, 2017.
International Search Report and Written Opinion from International Application No. PCT/US2017/043025 mailed Oct. 18, 2017.
International Search Report and Written Opinion from International Application No. PCT/US2018/015968 mailed Apr. 6, 2018.
International Search Report and Written Opinion from International Application No. PCT/US2019/029608 mailed Sep. 3, 2019.
International Search Report and Written Opinion from International Application No. PCT/US2019/029609 mailed Sep. 3, 2019.
International Search Report and Written Opinion from International Application No. PCT/US2019/029610 mailed Sep. 3, 2019.
International Search Report and Written Opinion from International Application No. PCT/US2019/029611 mailed Jul. 3, 2019.
International Search Report and Written Opinion from International Application No. PCT/US2019/029613 mailed Jul. 3, 2019.
International Search Report and Written Opinion from International Application No. PCT/US2019/029614 mailed Sep. 26, 2019.
International Search Report and Written Opinion from International Application No. PCT/US2019/029616 mailed Aug. 30, 2019.
International Search Report and Written Opinion from International Application No. PCT/US2020/023572 mailed Jul. 6, 2020.
International Search Report and Written Opinion from International Application No. PCT/US2020/033064 mailed Aug. 31, 2020.
International Search Report and Written Opinion from International Application No. PCT/US2020/033122 mailed Aug. 31, 2020.
International Search Report and Written Opinion from International Application No. PCT/US2020/040860 mailed Oct. 2, 2020.
International Search Report and Written Opinion from International Application No. PCT/US2020/041242 mailed Nov. 17, 2020.
International Search Report and Written Opinion from International Application No. PCT/US2020/041249 mailed Oct. 2, 2020.
International Search Report and Written Opinion from International Application No. PCT/US2020/042262 mailed Oct. 14, 2020.
International Search Report and Written Opinion from International Application No. PCT/US2020/043059 mailed Oct. 6, 2020.
International Search Report and Written Opinion from International Application No. PCT/US2020/044024 mailed Nov. 12, 2020.
International Search Report and Written Opinion from International Application No. PCT/US2020/046914 mailed Dec. 1, 2020.
International Search Report and Written Opinion from International Application No. PCT/US2020/055680 mailed Dec. 15, 2020.
International Search Report and Written Opinion from International Application No. PCT/US2020/061563 mailed Feb. 19, 2021.
International Search Report and Written Opinion from International Application No. PCT/US2020/065234 mailed Apr. 12, 2021.
International Search Report and Written Opinion from International Application No. PCT/US2020/067451 mailed Mar. 25, 2021.
International Search Report and Written Opinion from International Application No. PCT/US2020/067454 mailed Mar. 29, 2021.
International Search Report and Written Opinion from International Application No. PCT/US2020/067455 mailed Mar. 26, 2021.
International Search Report and Written Opinion from International Application No. PCT/US2021/015024 mailed May 18, 2021.
International Search Report and Written Opinion from International Application No. PCT/US2021/015787 mailed May 27, 2021.
International Search Report and Written Opinion from International Application No. PCT/US2021/023001 mailed Jun. 21, 2021.
International Search Report and Written Opinion from International Application No. PCT/US2021/024162 mailed Jul. 8, 2021.
International Search Report and Written Opinion from International Application No. PCT/US2021/027061 mailed Jul. 19, 2021.
International Search Report and Written Opinion from International Application No. PCT/US2021/027104 mailed Jul. 6, 2021.
International Search Report and Written Opinion from International Application No. PCT/US2021/027314 mailed Jul. 6, 2021.
International Search Report and Written Opinion from International Application No. PCT/US2021/027422 mailed Aug. 12, 2021.
International Search Report and Written Opinion from International Application No. PCT/US2021/027425 mailed Aug. 11, 2021.
International Search Report and Written Opinion from International Application No. PCT/US2021/027913 mailed Jul. 12, 2021.
International Search Report and Written Opinion from International Application No. PCT/US2021/027917 mailed Aug. 19, 2021.
International Search Report and Written Opinion from International Application No. PCT/US2021/035181 mailed Sep. 16, 2021.
International Search Report and Written Opinion from International Application No. PCT/US2021/043893 mailed Nov. 22, 2021.
International Search Report and Written Opinion from International Application No. PCT/US2021/044699 mailed Nov. 22, 2021.
International Search Report and Written Opinion from International Application No. PCT/US2021/045188 mailed Jan. 26, 2022.
International Search Report and Written Opinion from International Application No. PCT/US2021/047536 mailed Dec. 23, 2021.
International Search Report and Written Opinion from International Application No. PCT/US2021/048211 mailed Dec. 22, 2021.
International Search Report and Written Opinion from International Application No. PCT/US2021/048661 mailed Feb. 14, 2022.
International Search Report and Written Opinion from International Application No. PCT/US2021/056566 mailed Feb. 11, 2022.
International Search Report and Written Opinion from International Application No. PCT/US2021/060993 mailed Mar. 18, 2022.
Issue Notification for U.S. Appl. No. 14/952,591 mailed Jul. 28, 2021.
Issue Notification for U.S. Appl. No. 15/171,968 mailed Mar. 3, 2021.
Issue Notification for U.S. Appl. No. 15/221,106 mailed Jul. 24, 2019.
Issue Notification for U.S. Appl. No. 15/238,427 mailed Jul. 24, 2019.
Issue Notification for U.S. Appl. No. 15/260,103 mailed Aug. 7, 2019.
Issue Notification for U.S. Appl. No. 15/611,587 mailed Feb. 20, 2019.
Issue Notification for U.S. Appl. No. 15/612,325 mailed Mar. 24, 2021.
Issue Notification for U.S. Appl. No. 29/624,661 mailed Aug. 4, 2021.

(56) References Cited

OTHER PUBLICATIONS

Non-Final Office Action for U.S. Appl. No. 14/592,591 mailed Mar. 20, 2020.
Non-Final Office Action for U.S. Appl. No. 14/722,613 mailed Jun. 13, 2019.
Non-Final Office Action for U.S. Appl. No. 14/947,759 mailed Mar. 17, 2016.
Non-Final Office Action for U.S. Appl. No. 14/952,591 mailed Aug. 1, 2017.
Non-Final Office Action for U.S. Appl. No. 14/952,591 mailed Mar. 20, 2020.
Non-Final Office Action for U.S. Appl. No. 14/952,591 mailed Mar. 21, 2019.
Non-Final Office Action for U.S. Appl. No. 14/952,591 mailed Sep. 28, 2018.
Non-Final Office Action for U.S. Appl. No. 15/171,968 mailed May 11, 2020.
Non-Final Office Action for U.S. Appl. No. 15/171,968 mailed Aug. 20, 2019.
Non-Final Office Action for U.S. Appl. No. 15/171,968 mailed Jun. 12, 2018.
Non-Final Office Action for U.S. Appl. No. 15/221,106 mailed Jun. 5, 2018.
Non-Final Office Action for U.S. Appl. No. 15/238,427 mailed Aug. 8, 2018.
Non-Final Office Action for U.S. Appl. No. 15/260,103 mailed Sep. 26, 2018.
Non-Final Office Action for U.S. Appl. No. 15/611,587 mailed Dec. 29, 2017.
Non-Final Office Action for U.S. Appl. No. 15/611,587 mailed Jul. 13, 2018.
Non-Final Office Action for U.S. Appl. No. 15/612,325 mailed Mar. 19, 2020.
Non-Final Office Action for U.S. Appl. No. 16/245,726 mailed Jan. 21, 2022.
Non-Final Office Action for U.S. Appl. No. 16/369,676 mailed Mar. 31, 2022.
Non-Final Office Action for U.S. Appl. No. 16/449,039 mailed Dec. 8, 2021.
Non-Final Office Action for U.S. Appl. No. 16/452,145 mailed Sep. 28, 2021.
Non-Final Office Action for U.S. Appl. No. 16/452,258 mailed Sep. 28, 2021.
Non-Final Office Action for U.S. Appl. No. 16/478,180 mailed Oct. 22, 2021.
Non-Final Office Action for U.S. Appl. No. 16/899,956 mailed Oct. 16, 2020.
Non-Final Office Action for U.S. Appl. No. 16/899,956 mailed Sep. 2, 2021.
Non-Final Office Action for U.S. Appl. No. 16/904,868 mailed Nov. 25, 2020.
Non-Final Office Action for U.S. Appl. No. 16/904,868 mailed Oct. 5, 2021.
Non-Final Office Action for U.S. Appl. No. 16/905,400 mailed Dec. 2, 2020.
Non-Final Office Action for U.S. Appl. No. 16/905,400 mailed Jul. 22, 2021.
Non-Final Office Action for U.S. Appl. No. 17/088,272 mailed Jan. 25, 2021.
Non-Final Office Action for U.S. Appl. No. 17/330,657 mailed Aug. 11, 2021.
Non-Final Office Action for U.S. Appl. No. 29/624,661 mailed Jul. 18, 2019.
Non-Final Office Action for U.S. Appl. No. 29/694,002 mailed Jun. 24, 2020.
Non-Final Office Action for U.S. Appl. No. 29/741,751 mailed Jan. 18, 2022.
Notice of Allowance for U.S. Appl. No. 14/952,591 mailed Apr. 5, 2021.
Notice of Allowance for U.S. Appl. No. 14/952,591 mailed Jul. 8, 2021.
Notice of Allowance for U.S. Appl. No. 15/171,968 mailed Feb. 16, 2021.
Notice of Allowance for U.S. Appl. No. 15/171,968 mailed Nov. 6, 2020.
Notice of Allowance for U.S. Appl. No. 15/221,106 mailed May 1, 2019.
Notice of Allowance for U.S. Appl. No. 15/238,427 mailed May 23, 2019.
Notice of Allowance for U.S. Appl. No. 15/260,103 mailed Jun. 7, 2019.
Notice of Allowance for U.S. Appl. No. 15/611,587 mailed Dec. 21, 2018.
Notice of Allowance for U.S. Appl. No. 15/612,325 mailed Feb. 19, 2021.
Notice of Allowance for U.S. Appl. No. 15/612,325 mailed Jan. 21, 2021.
Notice of Allowance for U.S. Appl. No. 16/899,956 mailed Dec. 29, 2021.
Notice of Allowance for U.S. Appl. No. 17/088,272 mailed Aug. 5, 2021.
Notice of Allowance for U.S. Appl. No. 17/088,272 mailed Mar. 4, 2022.
Notice of Allowance for U.S. Appl. No. 17/088,272 mailed Nov. 24, 2021.
Notice of Allowance for U.S. Appl. No. 17/330,657 mailed Mar. 16, 2022.
Notice of Allowance for U.S. Appl. No. 17/330,657 mailed Nov. 26, 2021.
Notice of Allowance for U.S. Appl. No. 29/624,661 mailed Apr. 28, 2021.
Notice of Allowance for U.S. Appl. No. 29/624,661 mailed Jul. 10, 2020.
Notice of Allowance for U.S. Appl. No. 29/624,661 mailed May 14, 2020.
Notice of Allowance for U.S. Appl. No. 29/624,661 mailed Sep. 29, 2020.
Notice of Allowance for U.S. Appl. No. 29/694,002 mailed Apr. 29, 2021.
Notice of Allowance for U.S. Appl. No. 29/694,002 mailed Jan. 29, 2021.
Notice of Allowance for U.S. Appl. No. 29/694,002 mailed Oct. 16, 2020.
Notice to File Missing Parts for U.S. Appl. No. 17/179,116 mailed Mar. 3, 2021.
Restriction Requirement for U.S. Appl. No. 16/433,773 mailed Dec. 7, 2021.
Restriction Requirement for U.S. Appl. No. 16/478,180 mailed May 25, 2021.
U.S. Appl. No. 14/625,469, filed Feb. 28, 2015.
U.S. Appl. No. 14/947,759, filed Nov. 20, 2015.
U.S. Appl. No. 14/952,591, filed Nov. 25, 2015.
U.S. Appl. No. 15/171,968, filed Jun. 2, 2016.
U.S. Appl. No. 15/221,106, filed Jul. 27, 2016.
U.S. Appl. No. 15/260,103, filed Sep. 8, 2016.
U.S. Appl. No. 15/384,196 filed Dec. 19, 2016.
U.S. Appl. No. 15/611,587, filed Jun. 1, 2017.
U.S. Appl. No. 15/612,325, filed Jun. 2, 2017.
U.S. Appl. No. 16/245,726, filed Jan. 11, 2019.
U.S. Appl. No. 16/369,676, filed Mar. 29, 2019.
U.S. Appl. No. 16/433,773, filed Jun. 6, 2019.
U.S. Appl. No. 16/449,039, filed Jun. 21, 2019.
U.S. Appl. No. 16/452,145, filed Jun. 25, 2019.
U.S. Appl. No. 16/452,258, filed Jun. 25, 2019.
U.S. Appl. No. 16/478,180 filed Jul. 16, 2019.
U.S. Appl. No. 16/904,868, filed Jun. 18, 2020.
U.S. Appl. No. 16/905,400, filed Jun. 18, 2020.
U.S. Appl. No. 17/051,550, filed Oct. 29, 2020.
U.S. Appl. No. 17/051,554, filed Oct. 29, 2020.
U.S. Appl. No. 17/051,585, filed Oct. 29, 2020.
U.S. Appl. No. 17/051,600, filed Oct. 29, 2020.
U.S. Appl. No. 17/088,272, filed Nov. 3, 2020.

(56) References Cited

OTHER PUBLICATIONS

U.S. Appl. No. 17/179,116, filed Feb. 18, 2021.
U.S. Appl. No. 17/330,657, filed May 26, 2021.
U.S. Appl. No. 17/378,015, filed Jul. 16, 2021.
U.S. Appl. No. 17/394,055, filed Aug. 4, 2021.
U.S. Appl. No. 17/412,864, filed Aug. 26, 2021.
U.S. Appl. No. 17/444,825, filed Aug. 10, 2021.
U.S. Appl. No. 17/446,256, filed Aug. 27, 2021.
U.S. Appl. No. 17/446,654, filed Sep. 1, 2021.
U.S. Appl. No. 17/447,123, filed Sep. 8, 2021.
U.S. Appl. No. 17/450,864, filed Oct. 14, 2021.
U.S. Appl. No. 17/451,345, filed Oct. 19, 2021.
U.S. Appl. No. 17/451,354, filed Oct. 19, 2021.
U.S. Appl. No. 17/453,260, filed Nov. 2, 2021.
U.S. Appl. No. 17/453,560, filed Nov. 4, 2021.
U.S. Appl. No. 17/461,036 mailed Aug. 30, 2021.
U.S. Appl. No. 17/494,578, filed Oct. 5, 2021.
U.S. Appl. No. 17/501,591, filed Oct. 14, 2021.
U.S. Appl. No. 17/595,747, filed Nov. 23, 2021.
U.S. Appl. No. 17/597,408, filed Jan. 5, 2022.
U.S. Appl. No. 17/597,673, filed Jan. 18, 2022.
U.S. Appl. No. 17/614,173, filed Nov. 24, 2021.
U.S. Appl. No. 17/631,619, filed Jan. 31, 2022.
U.S. Appl. No. 17/645,821, filed Dec. 23, 2021.
U.S. Appl. No. 17/646,771, filed Jan. 3, 2022.
U.S. Appl. No. 17/653,314, filed Mar. 3, 2022.
U.S. Appl. No. 17/653,920, filed Mar. 8, 2022.
U.S. Appl. No. 17/654,156 filed Mar. 9, 2022.
U.S. Appl. No. 17/655,464, filed Mar. 18, 2022.
U.S. Appl. No. 17/657,474, filed Mar. 31, 2022.
U.S. Appl. No. 29/741,751, filed Jul. 15, 2020.
U.S. Appl. No. 61/955,537, filed Mar. 19, 2014.
U.S. Appl. No. 62/082,279, filed Nov. 20, 2014.
U.S. Appl. No. 62/084,078, filed Nov. 25, 2014.
U.S. Appl. No. 62/414,963, filed Oct. 31, 2016.
U.S. Appl. No. 62/452,437, filed Jan. 31, 2017.
U.S. Appl. No. 62/485,578, filed Apr. 14, 2017.
U.S. Appl. No. 62/665,297, filed May 1, 2018.
U.S. Appl. No. 62/665,302, filed May 1, 2018.
U.S. Appl. No. 62/665,317, filed May 1, 2018.
U.S. Appl. No. 62/665,321, filed May 1, 2018.
U.S. Appl. No. 62/665,331, filed May 1, 2018.
U.S. Appl. No. 62/665,335, filed May 1, 2018.
U.S. Appl. No. 62/853,279, filed May 28, 2019.
U.S. Appl. No. 62/853,889, filed May 29, 2019.
U.S. Appl. No. 62/864,656, filed Jun. 21, 2019.
U.S. Appl. No. 62/873,045, filed Jul. 11, 2019.
U.S. Appl. No. 62/873,048, filed Jul. 11, 2019.
U.S. Appl. No. 62/876,500, filed Jul. 19, 2019.
U.S. Appl. No. 62/877,558, filed Jul. 23, 2019.
U.S. Appl. No. 62/883,172, filed Aug. 6, 2019.
U.S. Appl. No. 62/889,149, filed Aug. 20, 2019.
U.S. Appl. No. 62/923,279, filed Oct. 18, 2019.
U.S. Appl. No. 62/935,337, filed Nov. 14, 2019.
U.S. Appl. No. 62/938,447, filed Nov. 21, 2019.
U.S. Appl. No. 62/949,187, filed Dec. 17, 2019.
U.S. Appl. No. 62/956,756, filed Jan. 3, 2020.
U.S. Appl. No. 62/956,767, filed Jan. 3, 2020.
U.S. Appl. No. 62/956,770, filed Jan. 3, 2020.
U.S. Appl. No. 62/967,977, filed Jan. 30, 2020.
U.S. Appl. No. 62/994,912, filed Mar. 26, 2020.
U.S. Appl. No. 63/011,445, filed Apr. 17, 2020.
U.S. Appl. No. 63/011,487, filed Apr. 17, 2020.
U.S. Appl. No. 63/011,571, filed Apr. 17, 2020.
U.S. Appl. No. 63/011,657, filed Apr. 17, 2020.
U.S. Appl. No. 63/011,760, filed Apr. 17, 2020.
U.S. Appl. No. 63/012,347, filed Apr. 20, 2020.
U.S. Appl. No. 63/012,384, filed Apr. 20, 2020.
U.S. Appl. No. 63/030,685, filed May 27, 2020.
U.S. Appl. No. 63/033,310, filed Jun. 2, 2020.
U.S. Appl. No. 63/047,374, filed Jul. 2, 2020.
U.S. Appl. No. 63/061,241, filed Aug. 5, 2020.
U.S. Appl. No. 63/061,244, filed Aug. 5, 2020.
U.S. Appl. No. 63/061,834, filed Aug. 6, 2020.
U.S. Appl. No. 63/064,017, filed Aug. 11, 2020.
U.S. Appl. No. 63/064,126 filed Aug. 11, 2020.
U.S. Appl. No. 63/067,542, filed Aug. 19, 2020.
U.S. Appl. No. 63/071,438, filed Aug. 28, 2020.
U.S. Appl. No. 63/071,821, filed Aug. 28, 2020.
U.S. Appl. No. 63/073,545, filed Sep. 2, 2020.
U.S. Appl. No. 63/073,553, filed Sep. 2, 2020.
U.S. Appl. No. 63/074,051, filed Sep. 3, 2020.
U.S. Appl. No. 63/074,066, filed Sep. 3, 2020.
U.S. Appl. No. 63/076,032, filed Sep. 9, 2020.
U.S. Appl. No. 63/076,474, filed Sep. 10, 2020.
U.S. Appl. No. 63/076,477, filed Sep. 10, 2020.
U.S. Appl. No. 63/082,261, filed Sep. 23, 2020.
U.S. Appl. No. 63/088,506, filed Oct. 7, 2020.
U.S. Appl. No. 63/088,511, filed Oct. 7, 2020.
U.S. Appl. No. 63/088,539, filed Oct. 7, 2020.
U.S. Appl. No. 63/094,464, filed Oct. 21, 2020.
U.S. Appl. No. 63/094,498, filed Oct. 21, 2020.
U.S. Appl. No. 63/094,594, filed Oct. 21, 2020.
U.S. Appl. No. 63/094,608, filed Oct. 21, 2020.
U.S. Appl. No. 63/094,626, filed Oct. 21, 2020.
U.S. Appl. No. 63/094,646, filed Oct. 21, 2020.
U.S. Appl. No. 63/109,066, filed Nov. 3, 2020.
U.S. Appl. No. 63/109,084, filed Nov. 3, 2020.
U.S. Appl. No. 63/112,417, filed Nov. 11, 2020.
U.S. Appl. No. 63/119,161, filed Nov. 30, 2020.
U.S. Appl. No. 63/124,271, filed Dec. 11, 2020.
U.S. Appl. No. 63/133,892, filed Jan. 5, 2021.
U.S. Appl. No. 63/134,287, filed Jan. 6, 2021.
U.S. Appl. No. 63/134,450, filed Jan. 6, 2021.
U.S. Appl. No. 63/134,631, filed Jan. 7, 2021.
U.S. Appl. No. 63/134,632, filed Jan. 7, 2021.
U.S. Appl. No. 63/134,754, filed Jan. 7, 2021.
U.S. Appl. No. 63/138,878, filed Jan. 19, 2021.
U.S. Appl. No. 63/146,946, filed Feb. 8, 2021.
U.S. Appl. No. 63/147,013, filed Feb. 8, 2021.
U.S. Appl. No. 63/147,299, filed Feb. 9, 2021.
U.S. Appl. No. 63/148,723, filed Feb. 12, 2021.
U.S. Appl. No. 63/154,248, filed Feb. 26, 2021.
U.S. Appl. No. 63/155,395, filed Mar. 2, 2021.
U.S. Appl. No. 63/157,007, filed Mar. 5, 2021.
U.S. Appl. No. 63/157,014, filed Mar. 5, 2021.
U.S. Appl. No. 63/159,142, filed Mar. 10, 2021.
U.S. Appl. No. 63/159,186, filed Mar. 10, 2021.
U.S. Appl. No. 63/159,210, filed Mar. 10, 2021.
U.S. Appl. No. 63/159,280, filed Mar. 10, 2021.
U.S. Appl. No. 63/165,273, filed Mar. 24, 2021.
U.S. Appl. No. 63/165,384, filed Mar. 24, 2021.
U.S. Appl. No. 63/171,165, filed Apr. 6, 2021.
U.S. Appl. No. 63/172,975, filed Apr. 9, 2021.
U.S. Appl. No. 63/181,695, filed Apr. 29, 2021.
U.S. Appl. No. 63/192,274, filed May 24, 2021.
U.S. Appl. No. 63/193,235, filed May 26, 2021.
U.S. Appl. No. 63/193,406, filed May 26, 2021.
U.S. Appl. No. 63/193,891, filed May 27, 2021.
U.S. Appl. No. 63/208,262, filed Jun. 8, 2021.
U.S. Appl. No. 63/214,551, filed Jun. 24, 2021.
U.S. Appl. No. 63/214,570, filed Jun. 24, 2021.
U.S. Appl. No. 63/215,017, filed Jun. 25, 2021.
U.S. Appl. No. 63/228,244, filed Aug. 2, 2021.
U.S. Appl. No. 63/228,252, filed Aug. 2, 2021.
U.S. Appl. No. 63/228,258, filed Aug. 2, 2021.
U.S. Appl. No. 63/230,894, filed Aug. 9, 2021.
U.S. Appl. No. 63/238,457, filed Aug. 30, 2021.
U.S. Appl. No. 63/238,477, filed Aug. 30, 2021.
U.S. Appl. No. 63/241,562, filed Sep. 8, 2021.
U.S. Appl. No. 63/241,564, filed Sep. 8, 2021.
U.S. Appl. No. 63/241,575, filed Sep. 8, 2021.
U.S. Appl. No. 63/246,972, filed Sep. 22, 2021.

(56) References Cited

OTHER PUBLICATIONS

U.S. Appl. No. 63/247,375, filed Sep. 23, 2021.
U.S. Appl. No. 63/247,478, filed Sep. 23, 2021.
U.S. Appl. No. 63/247,491, filed Sep. 23, 2021.
U.S. Appl. No. 63/299,208, filed Jan. 13, 2022.
Sage's Second Supplemental Invalidity Contentions Regarding U.S. Pat. Nos. 8,287,508, 10,226,375, 10,390,989, and 10,376,407, 292 pages.
Plaintiff's Identification of Claim Terms and Proposed Constructions, 3 pages.
Sage's Preliminary Identification of Claim Elements and Proposed Constructions for U.S. Pat. Nos. 8,287,508, 10,226,376, 10,390,989 and 10,376,407, 7 pages.
Corrected Certificate of Service, 2020, 2 pages.
Excerpts from the 508 (Pat. No. 8,278,508) Patent's Prosecution History, 2020, 99 pages.
Declaration of Diane K. Newman Curriculum Vitae, 2020, pp. 1-199.
Sage's Supplemental and Initial Invalidity Contentions Regarding U.S. Pat. No's 8,287,508; 10,226,375; 10,390,989 and Initial Invalidity Contentions Regarding U.S. Pat. No. 10,376,407, Aug. 21, 2020, 277 pages.
Decision Granting Institution of Inter Partes Review for U.S. Pat. No. 8,287,508, Feb. 17, 2021, 39 pages.
Memorandum Order, Feb. 2021, 14 pgs.
Boehringer CareDry System—Second Generation for Non-Invasive Urinary Management for Females, Mar. 2021, 3 pgs.
PureWick's Response to Interrogatory No. 9 in *PureWick, LLC*v. *Sage Products, LLC*, Mar. 23, 2020, 6 pages.
Sage's Initial Invalidity Contentions Regarding U.S. Pat. Nos. 8,287,508; 10,226,375; and 10,390,989, May 29, 2020, 193 pages.
Defendant and Counterclaim Plaintiff Sage Products, Llc's Answer, Defenses, and Counterclaims To Plaintiff's Amended Complaint, Nov. 1, 2019.
Plaintiff's Opening Claim Construction Brief, Oct. 16, 2020, 26 pages.
"3 Devices Take Top Honors in Dare-To-Dream Medtech Design Contest", R+D Digest, Nov. 2013, 1 page.
"Advanced Mission Extender Device (AMDX) Products", Omni Medical Systems, Inc., 15 pages.
"AMXD Control Starter Kit Brochure", https://www.omnimedicalsys.com/index.php?page=products, 8 pages.
"AMXDmax In-Flight Bladder Relief", Omni Medical; Omni Medical Systems, Inc, 2015.
"AMXDX—Advanced Mission Extender Device Brochure", Omni Medical, 2 pages.
"External Urine Management for Female Anatomy", https://www.stryker.com/us/en/sage/products/sage-primafit.html, Jul. 2020, 4 pages.
"High Absorbancy Cellulose Acetate Electrospun Nanofibers for Feminine Hygiene Application", https://www.sciencedirect.com/science/article/abs/pii/S2352940716300701?via%3Dihub, Jul. 2016, 3 pages.
"How Period Panties Work", www.shethinx.com/pages/thinx-itworks, 2020, 10 pages.
"Hydrogel properties of electrospun polyvinylpyrrolidone and polyvinylpyrrolidone/poly(acrylic acid) blend nanofibers", https://pubs.rscorg/en/content/articlelanding/2015/ra/c5ra07514a#!divAbstract, 2015, 5 pages.
"In Flight Bladder Relief", Omni Medical, 14 pages.
"Making Women's Sanitary Products Safer and Cheaper", https://www.elsevier.com/connect/making-womens-sanitary-products-safer-and-cheaper, Sep. 2016, 10 pages.
"Novel Nanofibers Make Safe and Effective Absorbent for Sanitary Products", https://www.materialstoday.com/nanomaterials/news/nanofibers-make-safe-and-effective-absorbent/, Oct. 2016, 3 pages.
"Research and Development Work Relating to Assistive Technology 2005-06", British Department of Health, Nov. 2006, 40 pages.
"Rising Warrior Insulated Gallon Jug Cover", https://www.amazon.com/Rising-Warrior-Insulated-Sleeve, 2021, 2 pages.
"Step by Step How Ur24 WorksHome", http://medicalpatentur24.com, Aug. 30, 2017, 4 pages.
"Underwear that absorbs your period", Thinx!, 7 pages.
"Urine Bag Cover-Catheter Bag Cover 2000 ml vol. Medline Style-Multiple Sclerosis-Spine Injury-Suprapublic Catheter-Bladder Incontinence", https://www.etsy.com/listing/1142934658/urine-bag-cover-caatheter-bag-cover-2000, 2022, 1 page.
Chaudhary, et al., "Bioinspired dry adhesive: Poly(dimethylsiloxane) grafted with poly(2-ethylhexyl acrylate) brushes", European Polymer Journal, 2015, pp. 432-440.
Dai , et al., "Non-sticky and Non-slippery Biomimetic Patterned Surfaces", Journal of Bionic Engineering, Mar. 2020, pp. 326-334.
Espinoza-Ramirez , "Nanobiodiversity and Biomimetic Adhesives Development: From Nature to Production and Application", Journal of Biomaterials and Nanobiotechnology, pp. 78-101, 2019.
Hollister , "Female Urinary and Pouch and Male Urinary Pouch Brochure", 2011, 1 page.
Hollister , "Male Urinary Pouch External Collection Device", http://www.hollister.com/en/products/Continence-Care-Products/Urine-Collectors/Urine-Collection-Accessories/Male-Urinary-Pouch-External-Collection-Device.
Hollister , "Retracted Penis Pouch by Hollister", Vitality Medical.com, 6 pages.
Hwang , et al., "Multifunctional Smart Skin Adhesive Patches for Advanced Health Care", Adv. Healthcare Mater, 2018, pp. 1-20.
Jagota , et al., "Adhesion, friction, and compliance of bio-mimetic and bio-inspired structured interfaces", Materials Science and Engineering, 2011, pp. 253-292.
Jeong , et al., "A nontransferring dry adhesive with hierarchical polymer nanohairs", PNAS, Apr. 7, 2009, pp. 5639-5644.
Jeong , et al., "Nanohairs and nanotubes: Efficient structural elements for gecko-inspired artificial dry adhesives", Science Direct, 2009, pp. 335-346.
Karp , et al., "Dry solution to a sticky problem", Nature., 2011, pp. 42-43.
Lee , et al., "Continuous Fabrication of Wide-Tip Microstructures for Bio-Inspired Dry Adhesives via Tip Inking Process", Journal of Chemistry, Jan. 2, 2019, pp. 1-5.
MacAulay , et al., "A Noninvasive Continence Management System: Development and Evaluation of a Novel Toileting Device for Women", The Wound, Ostomy and Continence Nurses Society, 2007, pp. 641-648.
Newman , et al., "The Urinary Incontinence Sourcebook", Petition for Interparties Review, 1997, 23 pages.
Newton , et al., "Measuring Safety, Effectiveness and Ease of Use of PureWick in the Management of Urinary Incontinence in Bedbound Women: Case Studies", Jan. 8, 2016, 11 pages.
Parmar , "10 Finalists Chosen for Dare-to-Dream Medtech Design Challenge (PureWick)", Design Services, Nov. 10, 2014, 3 pages.
Parness , et al., "A microfabricated wedge-shaped adhesive array displaying gecko-like dynamic adhesion, directionality", J.R. Soc. Interface, 2009, pp. 1223-1232.
Purewick , "Incontinence Relief for Women", Presentation, Sep. 23, 2015, 7 pages.
Pytlik , "Super Absorbent Polymers", University of Buffalo.
Sachtman , "New Relief for Pilots? It Depends", Wired, 2008, 2 pages.
Tsipenyuk, et al., "Use of biomimetic hexagonal surface texture in friction against lubricated skin", Journal of The Royal Society—Interface, 2014, pp. 1-6.
"User & Maintenance Guide", Omni Medical, 2007, 16 pages.
"Vinyl Dust Cover, Janome #741811000, Janome, Sewing Parts Online", https://www.sewingpartsonline.com/vinyl-dust-cover-janome-74181000, 2020, 2 pages.
"Winners Announced for Dare-to-Dream Medtech Design Challenge", https://www.mddionline.com/design-engineering/winners-announced-dare-dream-medtech-design-challenge, 2014, 4 pages.
Ali , "Sustainability Assessment: Seventh Generation Diapers versus gDiapers", The University of Vermont, Dec. 6, 2011, pp. 1-31.
Autumn , et al., "Frictional adhesion: a new angle on gecko attachment", The Journal of Experimental Biology, 2006, pp. 3569-3579.

(56) References Cited

OTHER PUBLICATIONS

Cañas , et al., "Effect of nano- and micro-roughness on adhesion of bioinspired micropatterned surfaces", Acta Biomaterialia 8, 2012, pp. 282-288.
Advisory Action for U.S. Appl. No. 17/595,747 mailed Jun. 16, 2026.
Advisory Action for U.S. Appl. No. 17/933,590 mailed Jun. 2, 2026.
Advisory Action for U.S. Appl. No. 18/006,807 mailed May 4, 2026.
Advisory Action for U.S. Appl. No. 18/150,360 mailed Jun. 15, 2026.
Corrected Notice of Allowability for U.S. Appl. No. 17/614,173 mailed Jun. 30, 2026.
Corrected Notice of Allowability for U.S. Appl. No. 18/294,370 mailed Jun. 29, 2026.
Final Office Action for U.S. Appl. No. 18/115,444 mailed May 19, 2026.
Final Office Action for U.S. Appl. No. 18/556,945 mailed May 29, 2026.
Final Office Action for U.S. Appl. No. 18/682,006 mailed Jun. 23, 2026.
International Search Report and Written Opinion from International Application No. PCT/US2025/035383 mailed Oct. 10, 2025.
Issue Notification for U.S. Appl. No. 17/051,600 mailed Apr. 29, 2026.
Issue Notification for U.S. Appl. No. 17/759,697 mailed May 6, 2026.
Laerdal Medical, "LSCU 4—Laerdal Compact Suction Unit", Aug. 17, 2012, Youtube, https://www.youtube.com/watch?v= EWCAcc-Crwys.
Non-Final Office Action for U.S. Appl. No. 16/452,258 mailed Jun. 3, 2026.
Non-Final Office Action for U.S. Appl. No. 17/446,654 mailed May 14, 2026.
Non-Final Office Action for U.S. Appl. No. 17/631,619 mailed Jun. 29, 2026.
Non-Final Office Action for U.S. Appl. No. 17/809,083 mailed May 21, 2026.
Non-Final Office Action for U.S. Appl. No. 17/933,590 mailed Jun. 30, 2026.
Non-Final Office Action for U.S. Appl. No. 18/006,807 mailed Jun. 29, 2026.
Non-Final Office Action for U.S. Appl. No. 18/042,842 mailed Jun. 12, 2026.
Non-Final Office Action for U.S. Appl. No. 18/043,618 mailed May 1, 2026.
Non-Final Office Action for U.S. Appl. No. 18/260,391 mailed Apr. 29, 2026.
Non-Final Office Action for U.S. Appl. No. 18/265,736 mailed Jun. 2, 2026.
Non-Final Office Action for U.S. Appl. No. 18/294,403 mailed May 15, 2026.
Non-Final Office Action for U.S. Appl. No. 18/335,579 mailed Apr. 24, 2026.
Non-Final Office Action for U.S. Appl. No. 18/373,424 mailed Jun. 3, 2026.
Non-Final Office Action for U.S. Appl. No. 18/549,658 mailed May 29, 2026.
Non-Final Office Action for U.S. Appl. No. 18/569,778 mailed May 1, 2026.
Non-Final Office Action for U.S. Appl. No. 18/680,411 mailed Jun. 23, 2026.
Non-Final Office Action for U.S. Appl. No. 18/828,559 mailed Jun. 24, 2026.
Non-Final Office Action for U.S. Appl. No. 18/834,176 mailed May 18, 2026.
Non-Final Office Action for U.S. Appl. No. 18/835,068 mailed May 19, 2026.
Non-Final Office Action for U.S. Appl. No. 18/835,444 mailed Apr. 24, 2026.
Non-Final Office Action for U.S. Appl. No. 18/836,204 mailed Jun. 9, 2026.
Non-Final Office Action for U.S. Appl. No. 18/903,592 mailed Jun. 30, 2026.
Non-Final Office Action for U.S. Appl. No. 19/353,151 mailed May 15, 2026.
Notice of Allowance for U.S. Appl. No. 17/378,015 mailed Jun. 8, 2026.
Notice of Allowance for U.S. Appl. No. 17/446,256 mailed Jun. 16, 2026.
Notice of Allowance for U.S. Appl. No. 17/614,173 mailed May 7, 2026.
Notice of Allowance for U.S. Appl. No. 17/625,887 mailed Jun. 12, 2026.
Notice of Allowance for U.S. Appl. No. 17/635,866 mailed Jun. 23, 2026.
Notice of Allowance for U.S. Appl. No. 17/664,487 mailed Jun. 1, 2026.
Notice of Allowance for U.S. Appl. No. 17/757,311 mailed May 5, 2025.
Notice of Allowance for U.S. Appl. No. 17/758,152 mailed Jun. 16, 2026.
Notice of Allowance for U.S. Appl. No. 17/929,887 mailed Jun. 30, 2026.
Notice of Allowance for U.S. Appl. No. 18/139,523 mailed Jun. 5, 2026.
Notice of Allowance for U.S. Appl. No. 18/164,800 mailed Jun. 11, 2026.
Notice of Allowance for U.S. Appl. No. 18/246,121 mailed May 12, 2026.
Notice of Allowance for U.S. Appl. No. 18/247,986 mailed Jun. 30, 2026.
Notice of Allowance for U.S. Appl. No. 18/264,278 mailed Apr. 24, 2026.
Notice of Allowance for U.S. Appl. No. 18/558,502 mailed May 6, 2026.
Notice of Allowance for U.S. Appl. No. 18/610,523 mailed Jun. 30, 2026.
Notice of Allowance for U.S. Appl. No. 18/688,023 mailed Jun. 11, 2026.
Notice of Allowance for U.S. Appl. No. 18/758,025 mailed Jun. 17, 2026.
Restriction Requirement for U.S. Appl. No. 18/693,638 mailed Jun. 11, 2026.
U.S. Appl. No. 17/635,866, filed Feb. 16, 2022.
U.S. Appl. No. 17/759,587, filed Jul. 27, 2022.
U.S. Appl. No. 19/490,075, filed Dec. 4, 2025.
U.S. Appl. No. 19/582,525, filed Apr. 28, 2026.
U.S. Appl. No. 19/584,751, filed May 5, 2026.
U.S. Appl. No. 19/584,819, filed May 5, 2026.
U.S. Appl. No. 19/588,736 mailed May 19, 2026.
U.S. Appl. No. 19/595,261, filed Jun. 10, 2026.
U.S. Appl. No. 19/598,761, filed Jun. 18, 2026.
U.S. Appl. No. 19/657,823, filed Apr. 24, 2026.
U.S. Appl. No. 19/695,314, filed Jun. 2, 2026.
U.S. Appl. No. 19/708,236, filed Jun. 15, 2026.
U.S. Appl. No. 19/712,218, filed Jun. 18, 2026.
U.S. Appl. No. 19/716,830, filed Jun. 23, 2026.
U.S. Appl. No. 19/723,440, filed Jun. 29, 2026.

* cited by examiner

FLUID COLLECTION DEVICE HAVING ADJUSTABLE SHAFT PORTION, AND RELATED SYSTEMS AND METHODS

CROSS-REFERENCE TO RELATED APPLICATIONS

This application is a U.S. Nationalization of PCT International Application No. PCT/US2020/055680, filed on Oct. 15, 2020, which claims priority to U.S. Provisional Application No. 62/923,279 filed on Oct. 18, 2019, the entire disclosure of which is incorporated herein by this reference.

BACKGROUND

An individual may have limited or impaired mobility such that typical urination processes are challenging or impossible. For example, the individual may have surgery or a disability that impairs mobility. In another example, the individual may have restricted travel conditions such as those experience by pilots, drivers, and workers in hazardous areas. Additionally, fluid collection from the individual may be needed for monitoring purposes or clinical testing.

Bed pans and urinary catheters, such as a Foley catheter, may be used to address some of these circumstances. However, bed pans and urinary catheters have several problems associated therewith. For example, bed pans may be prone to discomfort, spills, and other hygiene issues. Urinary catheters be may be uncomfortable, painful, and may cause urinary tract infections.

Thus, users and manufacturers of fluid collection devices continue to seek new and improved devices, systems, and methods to collect urine.

SUMMARY

Embodiments disclosed herein are related to fluid collection devices and methods of using fluid collection devices. In an embodiment, a fluid collection device is disclosed. The fluid collection device includes a tubular shaft and a receptacle. The tubular shaft has an open end and an inner surface. The tubular shaft is adjustable between a first configuration having a first inner circumference sized to receive at least a portion of a penis within the tubular shaft and a second configuration having a second inner circumference smaller than the first inner circumference and sized to contact the penis with the inner surface. The receptacle is connected to the tubular shaft distal to the open end. The receptacle is configured to collect urine discharged from the penis when the penis is positioned within the tubular shaft.

In an embodiment, a method is disclosed. The method includes inserting a penis into a urine collection device such that a head of the penis is disposed within a receptacle of the urine collection device and a shaft of the penis is disposed within a tubular shaft of the urine collection device. The tubular shaft is cylindrical and has an open end and an inner surface, and the receptacle is connected to the tubular shaft distal to the open end of the tubular shaft. The method also includes adjusting the tubular shaft from a first configuration having a first inner circumference sized larger than a circumference of the shaft of the penis to a second configuration having a second inner circumference smaller than the first inner circumference and contacting the penis with the inner surface of the tubular shaft. The method also includes receiving urine discharged from the penis in the receptacle of the urine collection device. The method also includes removing the received urine from the receptacle of the urine collection device.

In an embodiment, a method of manufacturing a fluid collection device is disclosed. The method may include providing a tubular shaft having an open end and an inner surface, the tubular shaft being adjustable between a first configuration having a first inner circumference sized to receive at least a portion of a penis within the tubular shaft and a second configuration having a second inner circumference smaller than the first inner circumference and sized to contact the penis with the inner surface. The method also may include connecting a receptacle to the tubular shaft distal to the open end, the receptacle being configured to collect urine discharged from the penis when the penis is positioned within the tubular shaft.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the present disclosure, wherein identical reference numerals refer to identical or similar elements or features in different views or embodiments shown in the drawings.

DETAILED DESCRIPTION

Embodiments disclosed herein are related to fluid collection devices and methods of using the same. The devices and systems disclosed herein are configured to collect fluids from an individual. The fluids collected by the fluid collection devices may include at least one of urine, vaginal discharge, penile discharge, reproductive fluids, blood, sweat, or other bodily fluids.

The fluid collection devices have a generally cylindrical and expandable tubular shaft having an open end and an inner surface. The tubular shaft is adjustable between a first configuration and a second configuration. The first configuration of the tubular shaft includes a first inner circumference sized to receive at least a portion of a penis with the tubular shaft. In the first configuration, the tubular shaft is compressed longitudinally, thereby increasing the radius of the tubular shaft to allow insertion of the head and/or shaft of the penis into a central cavity of the tubular shaft. The second configuration of the tubular shaft includes a second inner circumference that is smaller than the first inner circumference and, in the second configuration, the second inner circumference is sized to contact the penis with the inner surface of the tubular shaft. In the second configuration, the tubular shaft is lengthened longitudinally, thereby decreasing the radius of the tubular shaft until the tubular shaft is secured to the shaft of the penis. The cylindrical and expandable tubular shaft allows the fluid collection device to be secured to the penis of a wearer without an adhesive or other separate securement device or strap. The cylindrical and expandable tubular shaft also allows the fluid collection device to be secured to the wearer without adhering or securing the device to the area around the penis of the wearer.

Figure 1A:
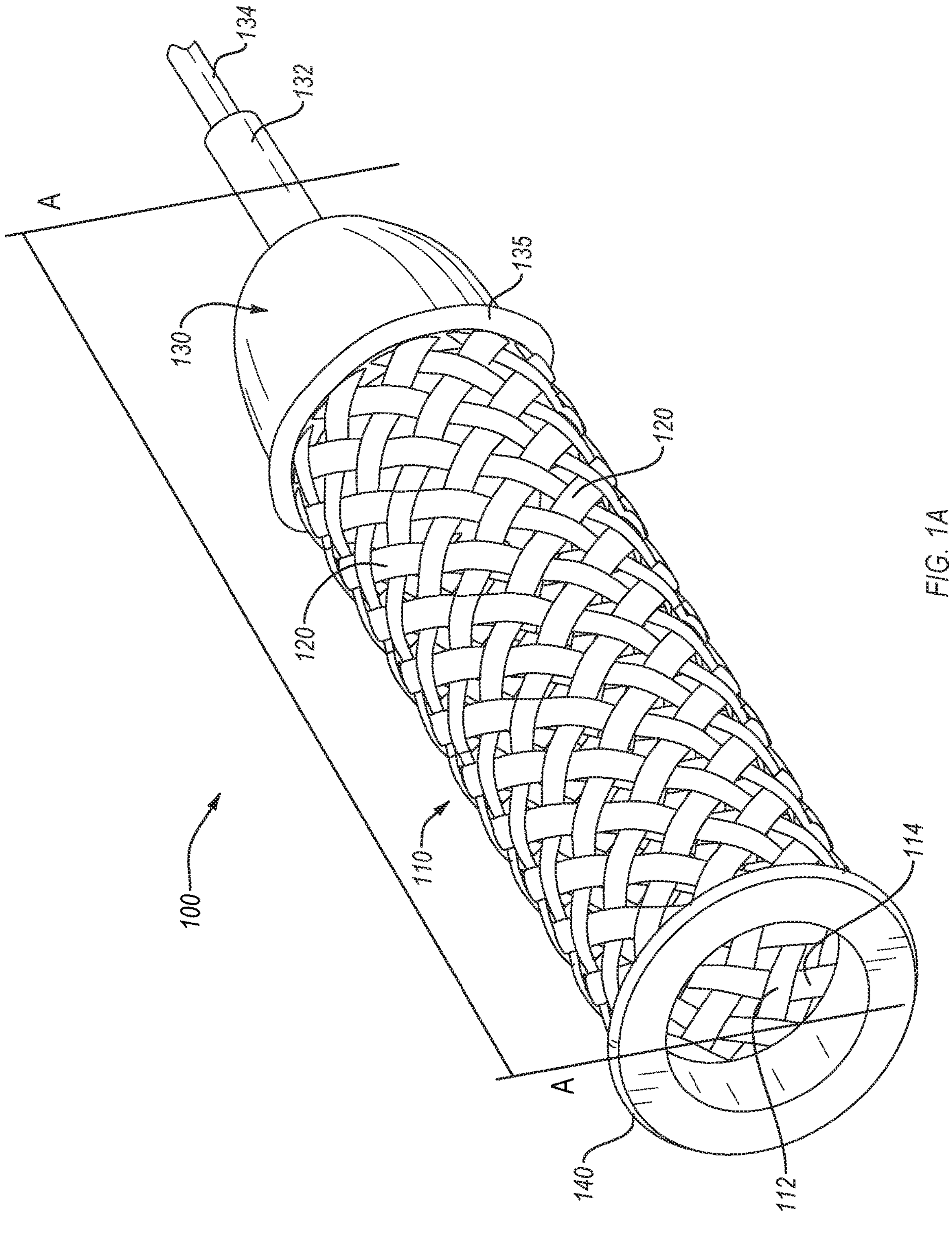
FIG. 1A is an isometric view of a fluid collection device, according to an embodiment.
Figure 1B:
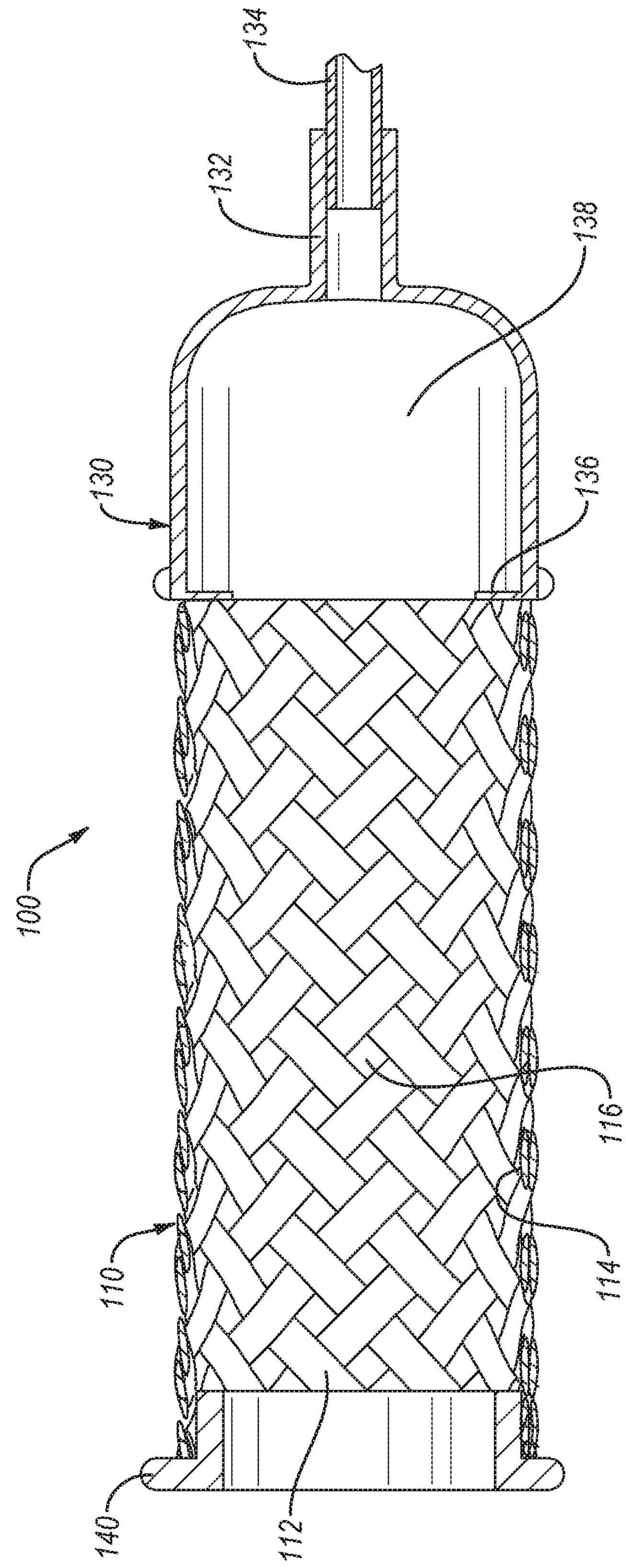
FIG. 1B is a cross-sectional view of the fluid collection device of FIG. 1A taken along the plane A-A, according to an embodiment.

FIG. 1A is an isometric view of a fluid collection device 100, according to an embodiment. FIG. 1B is a cross-sectional view of the fluid collection device 100 of FIG. 1A, taken along plane A-A. References to both FIGS. 1A and 1B are made below. The fluid collection device 100 includes a tubular shaft 110 and a receptacle 130. The tubular shaft 110 includes an open end 112 and a cylindrical, helically wound braid of a plurality of strips 120 of one or more materials. The helically wound braid of the plurality of strips 120 form an inner surface 114 of the tubular shaft 110 that defines a central cavity 116 of the tubular shaft 110. The plurality of strips 120 may be interwoven in a cross-hatched helical pattern, thereby forming and defining the central cavity 116 of the tubular shaft 110.

The helically wound braid of the plurality of strips 120 allows the tubular shaft 110 to be adjustable and selectively expanded or retracted with respect to an inner diameter of the tubular shaft 110. For example, the tubular shaft 110 is adjustable between a first configuration or position and a second configuration or position. In the first configuration, the tubular shaft 110 includes a first diameter or first inner circumference that is sized to receive the head of a penis and at least a portion of a shaft of the penis therein, allowing the head of the penis to pass through the central cavity 116 of the tubular shaft 110 and into the receptacle 130. In the second configuration, the tubular shaft 110 includes a second diameter or second inner circumference that is smaller or less than the first diameter or first inner circumference, and also sized to contact the shaft of the penis with the inner surface 114 of the tubular shaft 110, thereby securing the tubular shaft 110 to the shaft of the penis. The second diameter or second inner circumference may vary according to the preference or anatomy of the wearer. In some embodiments, the tubular shaft 110 is biased to the second configuration in which the tubular shaft 110 is sized to contact the shaft of the penis. Accordingly, the tubular shaft 110 may remain in the second configuration in which the tubular shaft 110 is sized to contact the shaft of the penis unless acted upon by the wearer or caregiver adjusting the tubular shaft 110 to the first configuration.

In some embodiments, in the second configuration the tubular shaft 110 includes a longitudinal length of about 2 cm to about 22 cm, such as about 2 cm to about 12 cm, about 12 cm to about 22 cm, about 2 cm to about 7 cm, about 7 cm to about 12 cm, about 12 cm to about 17 cm, about 17 cm to about 22 cm, about 2 cm to about 4 cm, about 4 cm to about 6 cm, about 6 cm to about 8 cm, about 8 cm to about 10 cm, about 10 cm to about 12 cm, about 12 cm to about 14 cm, about 14 cm to about 16 cm, about 16 cm to about 18 cm, about 18 cm to about 20 cm, about 20 cm to about 22 cm, at least about 2 cm, at least about 5 cm, at least about 10 cm, at least about 15 cm, at least about 20 cm, about 2 cm, about 3 cm, about 4 cm, about 5 cm, about 6 cm, about 7 cm, about 8 cm, about 9 cm, about 10 cm, about 11 cm, about 12 cm, about 13 cm, about 14 cm, about 15 cm, about 16 cm, about 17 cm, about 18 cm, about 19 cm, about 20 cm, about 21 cm, or about 22 cm.

In some embodiments, in the second configuration the tubular shaft 110 includes an inner diameter of about 1.5 cm to about 8 cm, about 1.5 cm to about 4 cm, about 4 cm to about 8 cm, about 1.5 cm to about 2.5 cm, about 2 cm to about 3 cm, about 3 cm to about 4 cm, about 4 cm to about 5 cm, about 5 cm to about 6 cm, about 6 cm to about 7 cm, about 7 cm to about 8 cm, less than about 9 cm, less than about 8 cm, less than about 7 cm, less than about 6 cm, less than about 5 cm, less than about 4 cm, less than about 3 cm, or less than about 2 cm. In some embodiments, in the first configuration the tubular shaft 110 includes an inner diameter of about 5 cm to about 13 cm, about 5 cm to about 9 cm, about 9 cm to about 13 cm, about 5 cm to about 7 cm, about 7 cm to about 9 cm, about 9 cm to about 11 cm, about 11 cm to about 13 cm, about 5 cm to about 6 cm, about 6 cm to about 7 cm, about 7 cm to about 8 cm, about 8 cm to about 9 cm, about 9 cm to about 10 cm, about 10 cm to about 11 cm, about 11 cm to about 12 cm, about 12 cm to about 13 cm, at least about 5 cm, at least about 6 cm, at least about 7 cm, at least about 8 cm, at least about 9 cm, at least about 10 cm, at least about 11 cm, at least about 12 cm, or at least about 13 cm. The tubular shaft 110 may be adjustable between any of the dimensions provided above.

In some embodiments, the helically wound braid of the plurality of strips 120 includes a weaving having a sufficiently tight braid that substantially all fluids (e.g. urine) are prevented from leaking through the tubular shaft 110 when the tubular shaft 110 is in the second configuration and contacting the shaft of the penis. Preventing substantially all fluid from leaking through tubular shaft 110 may include preventing at least 90%, at least 95%, at least 99%, or 100% of fluid leaking through the tubular shaft 110 when the urine collection device 100 is worn by a wearer.

Figure 1C:
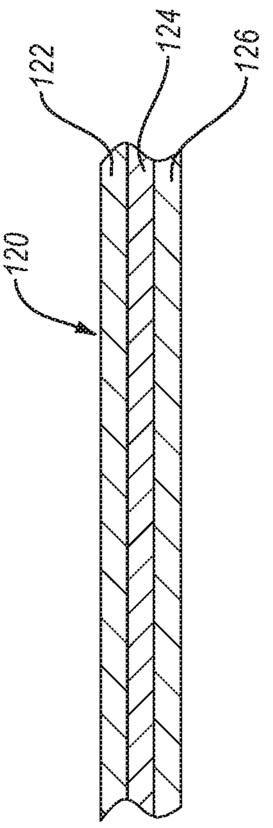
FIG. 1C is cross-sectional view of a strip of material of FIG. 1A, according to an embodiment.

Each strip of the plurality of strips 120 in the helically wound braid may be configured to allow the strip to slide past one or more other strips of the plurality of strips 120 when the tubular shaft 110 expands or contracts. In some embodiments, such as the fluid collection device 100 in FIGS. 1A and 1B, a gap or space may exist between adjacent helical strips 120. In some embodiments, adjacent helical strips 120 may generally interface or contact one another. Turning ahead to FIG. 1C, in the fluid collection device 100, each strip of the plurality of strips 120 of one or more materials in the tubular shaft 110 includes a tri-layer strip of three materials. The tri-layer strip of three materials may include first or inner layer 122 of wicking material, a second or intermediate layer 124 of a pad material, and a third or outer layer 126 of a fluid impermeable material. Together, the first or inner layer 122 of the plurality of strips 120 may form the inner surface 114 of the tubular shaft 110, thereby at least partially defining the central cavity 116. The three materials in each strip may be held together with an adhesive, an ultrasonic weld, a heat weld, or stitching.

The first or inner layer 122 of wicking material can include a fluid permeable membrane that is configured to wick any fluid away from the open end 112 and the central cavity 116, thereby preventing fluid from escaping out of the open end 112 of the tubular shaft 110. The first or inner layer 122 also may wick any fluid in the tubular shaft 110 generally towards the receptacle 130, as discussed in more detail below. The first or inner layer 122 may include any material that can wick fluid. For example, the first or inner layer 122 can include fabric, such as gauze (e.g., a silk, linen, polyester, or cotton gauze), another soft fabric (e.g., jersey knit fabric or the like), or another smooth fabric (e.g., rayon, satin, or the like). In some examples, the first or inner layer 122 can include an open cell foam. Forming the first or inner layer 122 from gauze, soft fabric, and/or smooth fabric can reduce chafing caused by the fluid collection device 100. In some embodiments, the first or inner layer 122 may be omitted or absent from each strip of the plurality of strips 120. In some embodiments, the second or intermediate layer 124 and the third or outer layer 126 may be omitted or absent from each strip of the plurality of strips 120, and each strip of the plurality of strips 120 includes only the fluid permeable membrane of the first or inner layer 122.

The second or intermediate layer 124 may include a fluid permeable support layer configured to support the first or inner layer 122 since the first or inner layer 122 may be formed from a foldable, flimsy or otherwise easily deformable material. The second or intermediate layer 124 can be formed from any fluid permeable material that is less deformable than the first or inner layer 122. For example, the second or intermediate layer 124 can include a porous nylon structure or an open cell foam. In embodiments, the second or intermediate layer 124 may be omitted or absent from each strip of the plurality of strips 120. In some embodiments, the first or inner layer 122 and the third or outer layer 126 may be omitted or absent from each strip of the plurality of strips 120, and each strip of the plurality of strips 120 includes only the fluid permeable support of the second or intermediate layer 124.

The third or outer layer 126 may include a fluid impermeable layer configured to retain fluids in the fluid collection device 100. For example, the third or outer layer 126 may be formed of any suitable fluid impermeable materials, such as a fluid impermeable polymer (e.g., silicone, polypropylene, polyethylene, polyethylene terephthalate (PET), polyurethane, a polycarbonate, a polyvinyl chloride, latex, silicone, etc.), a metal film, another suitable material, or combinations thereof. As such, the third or outer layer 126 may prevent at least some of the fluid(s) from exiting the tubular shaft 110 of the fluid collection device.

In some embodiments, the third or outer layer 126 may be air permeable and fluid impermeable. In such embodiments, the third or outer layer 126 may be formed of a hydrophobic material that defines a plurality of pores. In an example, one or more portions of at least an outer surface of the third or outer layer 126 may be formed from a soft and/or smooth material thereby reducing chafing of the skin of the user. In embodiments, the third or outer layer 126 may be omitted or absent from each strip of the plurality of strips 120. In some embodiments, the first or inner layer 122 and the second or intermediate layer 124 may be omitted or absent from each strip of the plurality of strips 120, and each strip of the plurality of strips 120 includes only the fluid impermeable layer of the third or outer layer 124.

Although each strip of the plurality of strips 120 in the fluid collection device 100 may include multiple layers of different materials, in some embodiments, the helically wound braid of the plurality of strips 120 may be formed from a single material. For example, the tubular shaft 110 can include a helically wound braid of a plurality of cords or strips 120 of a singular material, such as PET or any of the other materials referenced with respect to the first or inner layer 122, the second or intermediate layer 124, or the third or outer layer 126. In some embodiments, the tubular shaft 110 can include a helically wound braid of a plurality of strips 120 of a singular material that is different from any of the materials referenced with respect to the first or inner layer 122, the second or intermediate layer 124, or the third or outer layer 126

Returning to FIGS. 1A and 1B, the fluid collection device 100 also may include a ring 140 secured to the open end 112 of the tubular shaft 110. The ring 140 can be formed from a flexible polymer that exhibits a Young's modulus that is greater than the tubular shaft 110. As such, the ring 140 can provide some structure at or near the open end 112 of the tubular shaft 110. The increased rigidity of the ring 140 can cause the open end to remain open, thereby facilitating insertion of a penis into the fluid collection device 100. Further, in an embodiment, the increased rigidity of the ring 140 can enable the ring 140 to act as an attachment mechanism. In some embodiments, the ring 140 is omitted or absent from the fluid collection device 100.

The fluid collection device 100 also includes a receptacle 130 secured to the tubular shaft 110 distal to the open end 112 of the tubular shaft 110. The receptacle 130 may be secured to the tubular shaft 110 with at least one of an ultrasonic weld, a heat weld, an adhesive, stitching, etc. The receptacle 130 defines a chamber 138 within fluid collection device 100. The chamber 138 is in fluid communication with the central cavity 116 of the tubular shaft 110 when a penis is absent from the fluid collection device 100. The chamber 138 is sized and dimensioned to hold at least a portion of the head of the penis therein.

The receptacle 130 includes at least a fluid impermeable layer. In the fluid collection device 100 shown in FIGS. 1A and 1B, the receptacle 130 includes at least a head of a condom catheter. The receptacle 130 includes an outlet 132 configured connect to a tube 134 for drainage of urine from the urine collection device 100. The outlet 132 is generally positioned distal to the open end 112 of the tubular shaft 110. The receptacle 130 may include an elastic material the stretches or shrinks to secure to the head of the penis. In some embodiments, the receptacle 130 includes a roll 135 of material that may be rolled over at least a portion of the tubular shaft 110 after the penis is disposed within the fluid collection device 100.

The receptacle 130 may include a flexible or elastic material, such as polyurethane, resin, polyisoprene, latex, or combinations thereof. In some embodiments, the receptacle 130 includes one or more materials configured to retain a shape of the receptacle 130 when a penis is not positioned within the fluid collection device. In these and other embodiments, the receptacle 130 includes one or more of silicone, polypropylene, polyethylene, PET, polyurethane, a polycarbonate, a polyvinyl chloride, latex, silicone, etc. The receptacle 130 also may include an annular flap 136 between at least a portion of the receptacle 130 and the tubular shaft 110. The annular flap 136 may be a fluid impermeable flexible material that acts as seal between the chamber 138 and the central cavity 116 when a penis is inserted into the fluid collection device. In some embodiments, the annular flap 136 may be omitted from the fluid collection device 100.

In use, a penis is inserted through the open end 112 of the fluid collection device 100 at least partially into the tubular shaft 110. In some embodiments, the penis is inserted through the open end 112 of the fluid collection device 100 until the head of the penis passes through the tubular shaft 110 and is at least partially positioned within the chamber 138 of the receptacle 130. To insert the penis into the fluid collection device 100, the tubular shaft 110 may be compressed along a longitudinal axis, thereby increasing the inner circumference or diameter of the tubular shaft 110. In some embodiments, with the head of the penis at least partially positioned within the chamber 138 of the receptacle 130, the annular flap 136 may contact the penis and seal the chamber 138 from the central cavity 116 of the tubular shaft 110. In some embodiments, the receptacle 130 forms a seal between the chamber 138 and the central cavity 116 without the annular flap 136. In some embodiments, the weave of the tubular shaft 110 forms a seal that prevents fluids from exiting the fluid collection device 100 when the tubular shaft 110 is in the second configuration and contacting the penis positioned within the tubular shaft 110.

With the head of the penis positioned within the tubular shaft 110 or the chamber 138 of the receptacle 130, the tubular shaft 110 may be adjusted to the second configuration to secure the tubular shaft 110 to the shaft of the penis. As noted above, the tubular shaft 110 may be lengthened to decrease the inner circumference or diameter of the tubular shaft 110, thereby securing the tubular shaft to the penis without an adhesive. The tubular shaft 110 may be lengthened by pulling one end of the tubular shaft 110 away from the other end of the tubular shaft 110. The tubular shaft 110 also may be lengthened by compressing radially the tubular shaft 110. The adjustable tubular shaft 110 also allows a wearer to adjust the tubular shaft 110 to a desired comfortable tightness around the penis. Once the tubular shaft 110 is adjusted to tighten around the penis and the head of the penis is within the receptacle 130, urine discharged from the penis may exit through the outlet 132 of the receptacle 130, as described in greater detail below. The fluid collection device 100 may be fluidly coupled to a vacuum source that pulls or sucks discharged urine from the receptacle 130. In embodiments of the fluid collection device 100 having a plurality of strips 120 of three layers of material, urine in the tubular shaft 110 may be wicked from the tubular shaft 110 to the chamber 138 for removal from the urine collection device 100.

Figure 2A:
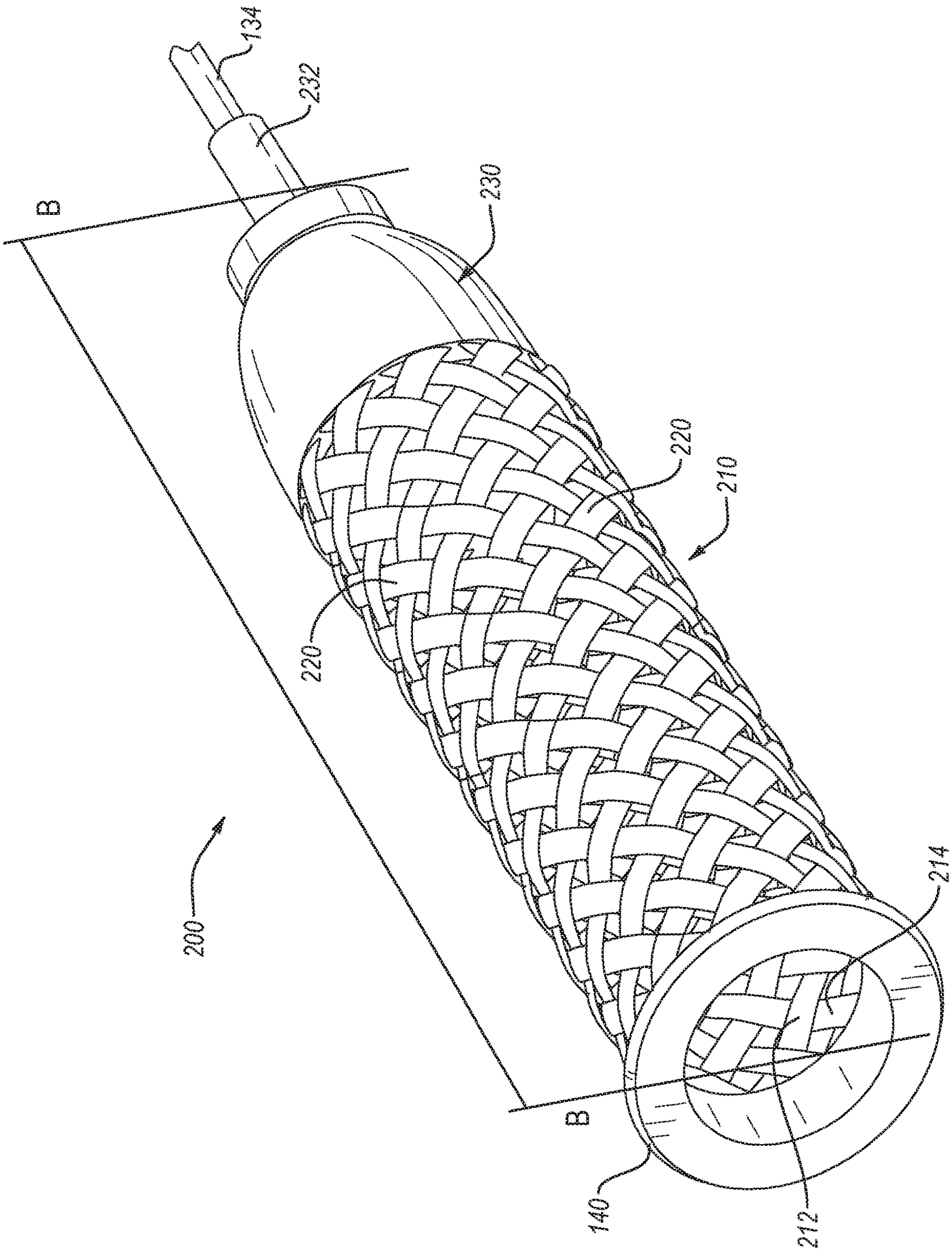
FIG. 2A is an isometric view of a fluid collection device, according to an embodiment.
Figure 2B:
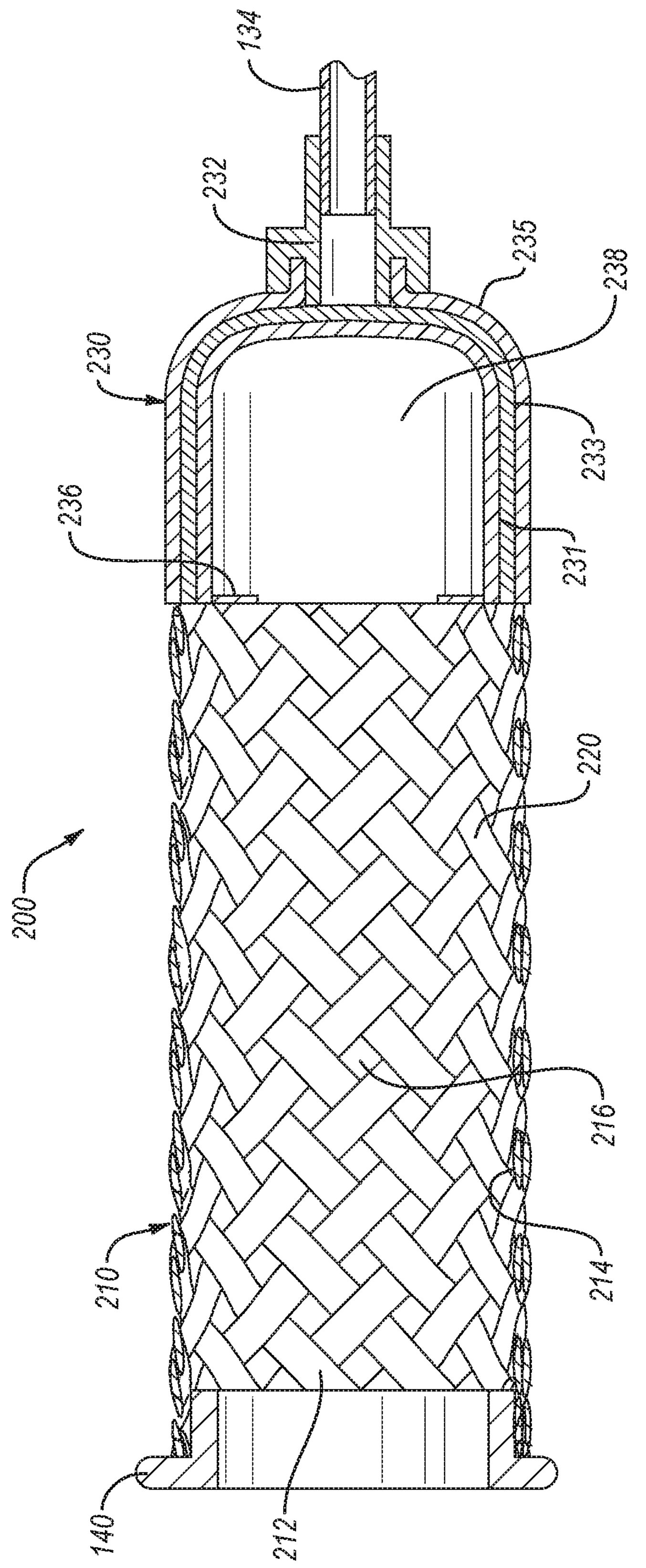
FIG. 2B is a cross-sectional view of the fluid collection device of FIG. 2A taken along the plane B-B, according to an embodiment.
Figure 2C:
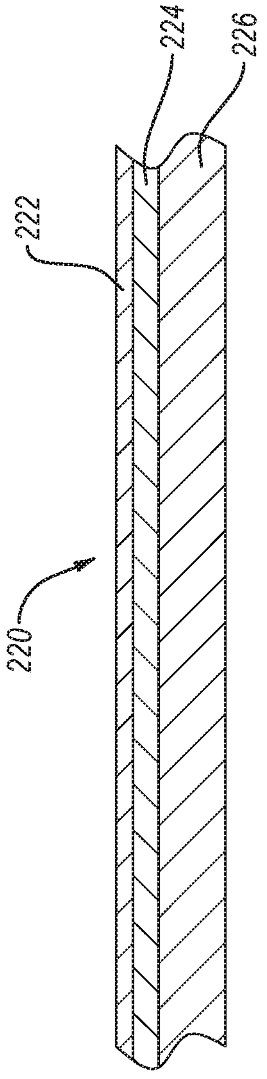
FIG. 2C is a cross-sectional view of a strip of material of FIG. 2A, according to an embodiment.

FIG. 2A is an isometric view of a fluid collection device 200, according to an embodiment. FIG. 2B is a cross-sectional view of the fluid collection device 200 of FIG. 2A, taken along plane B-B. References to both FIGS. 2A and 2B are made below. The fluid collection device 200 may include any of the features described above in relation to fluid collection device 100. For example, the fluid collection device 200 includes a tubular shaft 210 having an open end 212 and a cylindrical, helically wound braid of a plurality of strips 220 of one or more materials that form an inner surface 214 and define a central cavity 216. The helically wound braid of the plurality of strips 220 allows the tubular shaft 210 to be adjustable and selectively expanded or retracted with respect to an inner diameter of the tubular shaft 210, as described above in relation to the tubular shaft 110 of the fluid collection device 100. The tubular shaft 210 may include of the dimensions in the first configuration and/or the second configuration as provided above in relation to the tubular shaft 110. Turning to FIG. 2C, each strip of the plurality of strips 220 in the tubular shaft 210 may include a first or inner layer 222, a support wire 224, and a third or outer layer 226. The first or inner layer 222 may include any of the materials, features, or characteristics described above in relation to the first or inner layer 122, the second or intermediate layer 124, or the third or outer layer 126 of the tubular shaft 110. The support wire 224 is embedded in the strip between the first or inner layer 122 and the third or outer layer 226. The support wire 224 is configured to provide support to the tubular shaft 210 to allow the tubular shaft 210 to retain a generally cylindrical shape. The support wire 224 may include a metal wire, a plastic wire, a rubber wire, or combinations thereof. The third or outer layer 226 may include any of the materials, features, or characteristics described above in relation to the first or inner layer 122, the second or intermediate layer 124, or the third or outer layer 126 of the tubular shaft 110. In some embodiments, at least one of the first or inner layer 222 or the third or outer layer 226 are omitted or absent from the plurality of strips 220. In some embodiments, the helically wound braid of the plurality of strips 220 includes a weave having a sufficiently tight braid that substantially all fluids (e.g. urine) are prevented from leaking through the tubular shaft 210 when the tubular shaft 210 is in the second configuration and contacting the shaft of the penis.

Returning to FIGS. 2A and 2B, the fluid collection device 200 also includes a receptacle 230 having an outlet 232. The receptacle 230 may be secured to the tubular shaft 210 with at least one of an ultrasonic weld, a heat weld, an adhesive, stitching, etc. The receptacle 230 includes first or inner layer 231 of wicking material, a second or intermediate layer 233 of a pad material, and a third or outer layer 235 of a fluid impermeable material. In some embodiments, at least one (e.g., both) of the first or inner layer 231 and the second or intermediate layer 233 cover at least a portion (e.g., all) of the outlet 232. In some embodiments, the first or inner layer 231 and the second or intermediate layer 233 do not cover at least a portion (e.g., all) of the outlet 232 such that the tube 134 has unrestricted fluid communication with the chamber 238.

The first or inner layer 231 at least partially defines a chamber 238 of the receptacle 230. The outlet 232 may be secured to at least one of the first or inner layer 230, the second or intermediate layer 233, or the third or outer layer 235 of the receptacle 230. The outlet 232 is configured to connect to the tube 134 for drainage of urine from the urine collection device 200. The receptacle 230 also may include an annular flap 236 between at least a portion of the receptacle 230 and the tubular shaft 210. The annular flap 230 may be a fluid impermeable flexible material that acts as seal between the chamber 238 and the central cavity 216 when a penis is inserted into the fluid collection device. The annular flap 236 may be secured to and/or extend from at least one of the first or inner layer 230, the second or intermediate layer 233, or the third or outer layer 235 of the receptacle 230. In some embodiments, the annular flap 236 may be omitted or absent from the fluid collection device 200.

The first or inner layer 231 of wicking material can include a fluid permeable membrane that is configured to wick any fluid away from the head of the penis and the chamber 238. The first or inner layer 231 also may wick any fluid in the tubular shaft 110 generally towards the outlet 232. The first or inner layer 231 may include any material that can wick fluid. For example, the first or inner layer 231 can include fabric, such as gauze (e.g., a silk, linen, polyester, or cotton gauze), another soft fabric (e.g., jersey knit fabric or the like), or another smooth fabric (e.g., rayon, satin, or the like). In some examples, the first or inner layer 231 can include an open cell foam. Forming the first or inner layer 231 from gauze, soft fabric, and/or smooth fabric can reduce chafing cause by the fluid collection device 100. In some embodiments, the first or inner layer 231 may be omitted or absent from the receptacle 230.

The second or intermediate layer 233 may include a fluid permeable support layer configured to support the first or inner layer 231 since the first or inner layer 231 may be formed from a foldable, flimsy or otherwise easily deformable material. The second or intermediate layer 233 can be formed from any fluid permeable material that is less deformable than the first or inner layer 231. For example, the second or intermediate layer 233 can include a porous nylon structure or an open cell foam. In embodiments, the second or intermediate layer 233 may be omitted or absent from the receptacle 230.

The third or outer layer 235 may include a fluid impermeable layer. For example, the third or outer layer 235 may be formed of any suitable fluid impermeable materials, such as a fluid impermeable polymer (e.g., silicone, polypropylene, polyethylene, polyethylene terephthalate (PET), polyurethane, a polycarbonate, a polyvinyl chloride, latex, silicone, etc.), a metal film, another suitable material, or combinations thereof. As such, the third or outer layer 235 may prevent at least some of the fluid(s) from exiting the tubular shaft 110 of the fluid collection device.

In some embodiments, the third or outer layer 235 may be air permeable and fluid impermeable. In such embodiments, the third or outer layer 235 may be formed of a hydrophobic material that defines a plurality of pores. In an example, one or more portions of at least an outer surface of the third or outer layer 235 may be formed from a soft and/or smooth material thereby reducing chafing of the skin of the user. In some embodiments, the first or inner layer 231 and the second or intermediate layer 235 may be omitted from the receptacle 230, and the receptacle 230 includes only the fluid impermeable layer of the third or outer layer 230. In some embodiments, the receptacle 230 of the fluid collection device 200 may include any of the features described above in relation to the receptacle 130. In some embodiments, the receptacle 130 of the fluid collection device 100 (FIG. 1) may include any of the features described in relation to the receptacle 230.

The fluid collection device 200 may be used as described in relation to the fluid collection device 100. For example, a penis is inserted into the open end 212 of the fluid collection device 200 until the head of the penis is positioned in the tubular shaft 210 or passes through the tubular shaft 210 and is positioned within the chamber 238 of the receptacle 230. The tubular shaft 210 of the fluid collection device 200 may be adjusted to secure the tubular shaft 210 to the shaft of the penis as described in relation to the tubular shaft 110 of the fluid collection device 100.

Figure 3A:
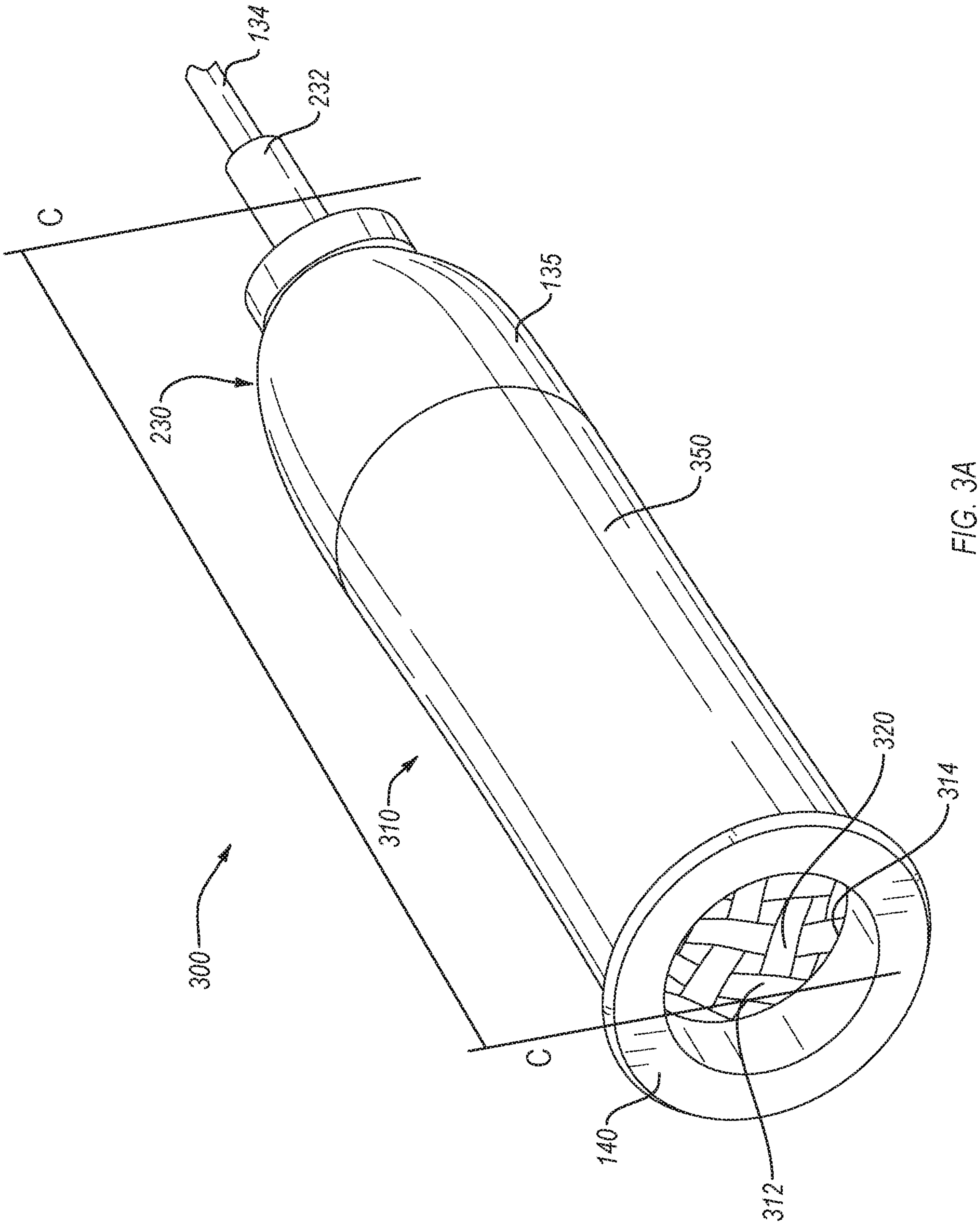
FIG. 3A is an isometric view of a fluid collection device, according to an embodiment.
Figure 3B:
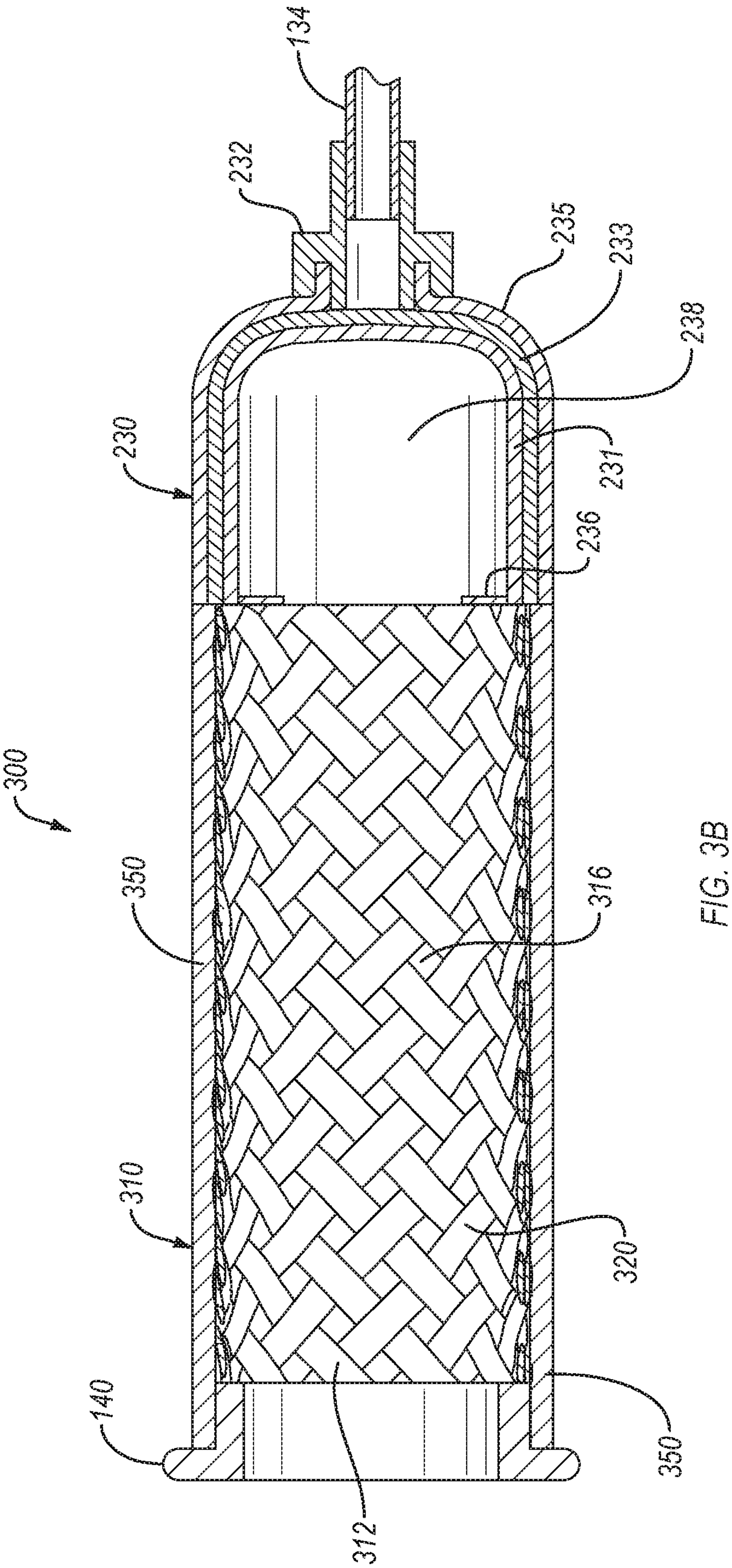
FIG. 3B is a cross-sectional view of the fluid collection device of FIG. 3A taken along plane C-C, according to an embodiment.

FIG. 3A is an isometric view of a fluid collection device 300, according to an embodiment. FIG. 3B is a cross-sectional view of the fluid collection device 300 of FIG. 3A, taken along plane C-C. References to both FIGS. 3A and 3B are made below. Unless otherwise noted, the fluid collection device 300 may include any of the features described above in relation to fluid collection devices 100 and 200. For example, the fluid collection device 300 includes a receptacle 230 having an outlet 232 configured to connect to a tube 134. Alternatively, the fluid collection device 300 may include a receptacle 130 described above.

The fluid collection device 300 also includes a tubular shaft 310 connected to the receptacle 230. The tubular shaft 310 includes an open end 312 and a cylindrical, helically wound braid of a plurality of strips 320 of one or more materials that form an inner surface 314 and define a central cavity 316 of the tubular shaft 310. The cylindrical, helically wound braid of a plurality of strips 320 of one or more materials may include any of the materials or features described in reference to the plurality of strips 120 or 220 of one or materials described above. The tubular shaft 310 may include of the dimensions in the first configuration and/or the second configuration as provided above in relation to the tubular shaft 110.

The plurality of strips 320 of one or more materials may be coated with a coating that prevents or inhibits urine from leaking through the helically wound braid of the plurality of strips 320. The coating may include at least one of a hydrophobic coating or a fluid impermeable coating. The coating may be applied to each strip of the plurality of strips 320 before the plurality of strips 320 are woven together to form the helically wound braid of the plurality of strips 320. Additionally or alternatively, the coating may be applied to the plurality of strips 320 after the plurality of strips 320 have been woven together to form the helically wound braid of the plurality of strips 320. For example, the tubular shaft 310 can include a helically wound braid of the plurality of strips 320 of a singular material, such as PET, that is coated with a hydrophobic coating or a fluid impermeable coating before or after the plurality of strips 320 of PET are woven together to form the helically wound braid of the plurality of strips 320. The helically wound braid of the plurality of strips 320 of the fluid collection device 300 also may be replace the helically wound braid of the plurality of strips 120 or 220 in the fluid collection devices 100 or 200, respectively.

The tubular shaft 310 also includes a fluid impermeable outer layer 350. The fluid impermeable outer layer 350 may be secured to opposing ends of the helically wound braid of the plurality of strips 320. The fluid impermeable outer layer 350 may include a collapsible material and a longitudinal length that is at least equal to a maximum longitudinal length of the helically wound braid of the plurality of strips 320. A fluid impermeable outer layer 350 having a longitudinal length that is at least equal to a maximum longitudinal length of the helically wound braid of the plurality of strips 320 allows the helically wound braid of the plurality of strips 320 to be elongated and retracted without interference from the fluid impermeable outer layer 350. In some embodiments, the fluid impermeable outer layer 350 includes an elastic or flexible material configured to elongate or retract with the helically wound braid of the plurality of strips 320. The outer layer 350 may be formed of any suitable fluid impermeable materials, such as a fluid impermeable polymer (e.g., silicone, polypropylene, polyethylene, polyethylene terephthalate (PET), polyurethane, a polycarbonate, a polyvinyl chloride, latex, silicone, etc.), a metal film, another suitable material, or combinations thereof. As such, the fluid impermeable outer layer 350 may prevent at least some of the fluid(s) from exiting the tubular shaft 310 of the fluid collection device 300. In some embodiments, the fluid impermeable outer layer 350 may be omitted from the fluid collection device 300. The fluid impermeable outer layer 350 also may be included in the fluid collection devices 100 and 200.

The fluid collection device 300 may be used as described in relation to the fluid collection devices 100 and 200. For example, a penis is inserted into the open end 312 of the fluid collection device 300 until the head of the penis is positioned within the tubular shaft 310 or passes through the tubular shaft 310 and is positioned within the chamber 238 of the receptacle 230. The tubular shaft 310 of the fluid collection device 300 may be adjusted to secure the tubular shaft 310 to the shaft of the penis as described in relation to the tubular shaft 110 of the fluid collection device 100.

Figure 4A:
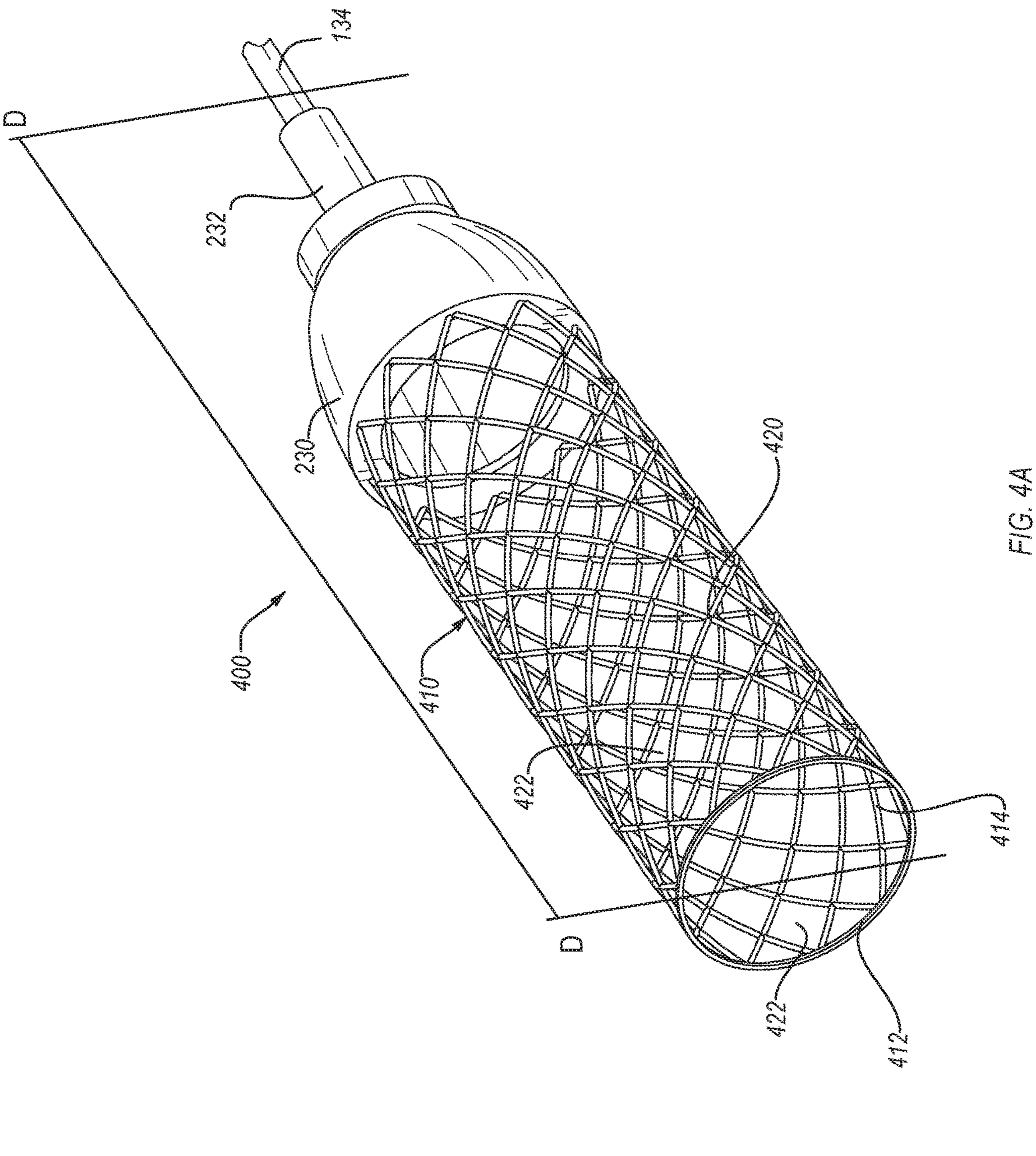
FIG. 4A is an isometric view of a fluid collection device, according to an embodiment.
Figure 4B:
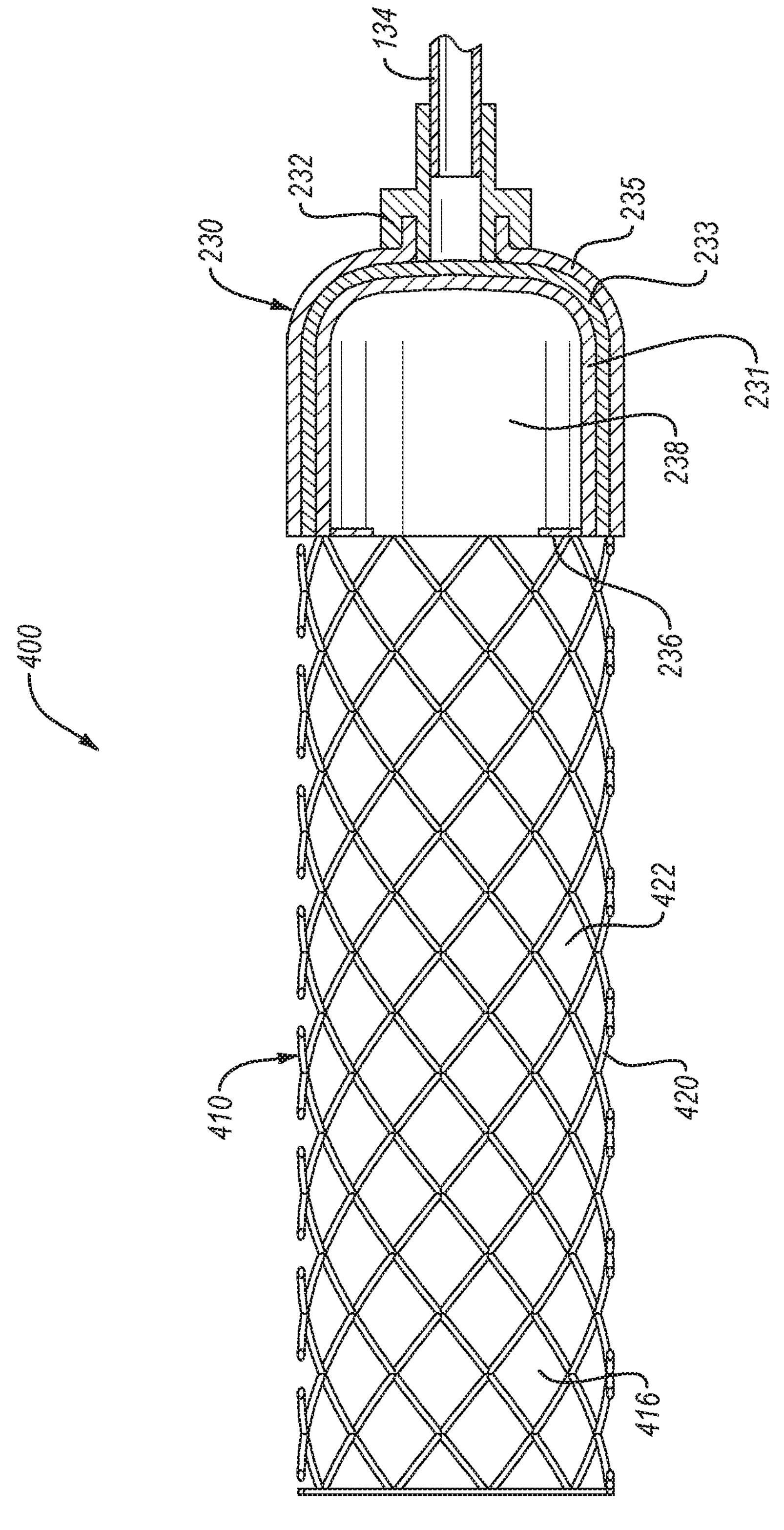
FIG. 4B is a cross-section view of the fluid collection device of FIG. 4A taken along plane D-D, according to an embodiment.

FIG. 4A is an isometric view of a fluid collection device 400, according to an embodiment. FIG. 4B is a cross-sectional view of the fluid collection device 400 of FIG. 4A, taken along plane D-D. References to both FIGS. 4A and 4B are made below. Unless otherwise noted, the fluid collection device 400 may include any of the features described above in relation to fluid collection devices 100, 200, and 300. For example, the fluid collection device 400 includes a receptacle 230 having an outlet 232 configured to connect to a tube 134. Alternatively, the fluid collection device 400 may include a receptacle 130 described above.

The fluid collection device 400 also includes a tubular shaft 410 connected to the receptacle 230. The tubular shaft 410 includes an open end 412 and sleeve of netting 420 forming an inner surface 414 of the tubular shaft 410 and at least partially defining a central cavity 416 of the tubular shaft 410. The sleeve of netting 420 may include of a plurality of openings 422 extending therethrough. The plurality of openings 422 may be formed in a plurality of shapes that enhance the elasticity of the sleeve of netting 420, such as generally circular, oval, diamond-shaped, or other polygonal shapes. The tubular shaft 410 may include of the dimensions in the first configuration and/or the second configuration as provided above in relation to the tubular shaft 110.

The sleeve of netting 420 allows the tubular shaft 410 to be adjustable and selectively expanded or retracted with respect to an inner diameter of the tubular shaft 410. For example, the tubular shaft 410 is adjustable between a first configuration or position and a second configuration or position. In the first configuration, the tubular shaft 410 includes a first diameter or first inner circumference that is sized to receive the head of a penis and at least a portion of a shaft of the penis therein, allowing the head of the penis to pass through the central cavity 416 of the tubular shaft 410 and into the receptacle 230. In the second configuration, the tubular shaft 410 includes a second diameter or second inner circumference that is sized to contact the shaft of the penis with the inner surface 414 of the tubular shaft 410, thereby securing the tubular shaft 410 to the shaft of the penis. In some embodiments, the sleeve of netting is biased towards the second configuration.

In use, a penis is inserted through the open end 412 of the fluid collection device 400 until the head of the penis passes through the tubular shaft 410 and is positioned within the chamber 238 of the receptacle 230. The sleeve of netting 420 stretches to allow passage of the head of the penis and at least a portion of the shaft of the penis therethrough. The sleeve of netting 420 may be biased to the described second configuration, thereby contracting around at least a portion of the shaft of the penis to secure the fluid collection device 400 to the penis. Once the tubular shaft 410 is secured around the shaft of the penis and the head of the penis is within the receptacle 230, urine discharged from the penis may exit through the outlet 232 of the receptacle 230.

In some embodiments, with the head of the penis positioned within the chamber 238 of the receptacle 230, the annular flap 236 may contact the penis and seal the chamber 238 from the central cavity 416 of the tubular shaft 410. In some embodiments, the receptacle 230 forms a seal between the chamber 238 and the central cavity 416 without the annular flap 236. In some embodiments, the tubular shaft 410 may include an outer fluid impermeable layer secured to the tubular shaft 410, such as the outer layer 350 described above.

Figure 5:
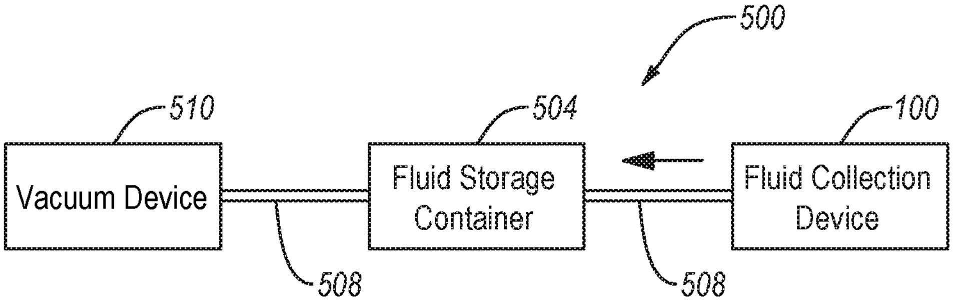
FIG. 5 is a block diagram of a system for fluid collection, according to an embodiment.

FIG. 5 is a block diagram of a system 500 for fluid collection, according to an embodiment. The system 500 includes a fluid collection device 100. Although the fluid collection device 100 is shown in FIG. 5, the system 500 may include any of the fluid collection devices 100, 200, 300, or 400. The fluid collection device 100 is fluidly coupled to a fluid storage container 504 through a conduit 508. At least a portion of the conduit 508 may include the tube 134 connected the fluid collection device 100. The fluid storage container 504 is fluidly coupled to a vacuum device 510 through a conduit 108. When activated, the vacuum device 510 is configured to pull a vacuum from the outlet 132 of the fluid collection device 100 through the fluid storage container 504. Accordingly, in use, the system 500 is configured to withdraw fluid, such as urine, from the fluid collection device 100 for storage within the fluid storage container 504. For example, as a user discharges urine in the fluid collection device, the vacuum device 510 pulls urine through the outlet 132 of the fluid collection device into the conduit 508 and into the fluid storage container 504.

Figure 6:
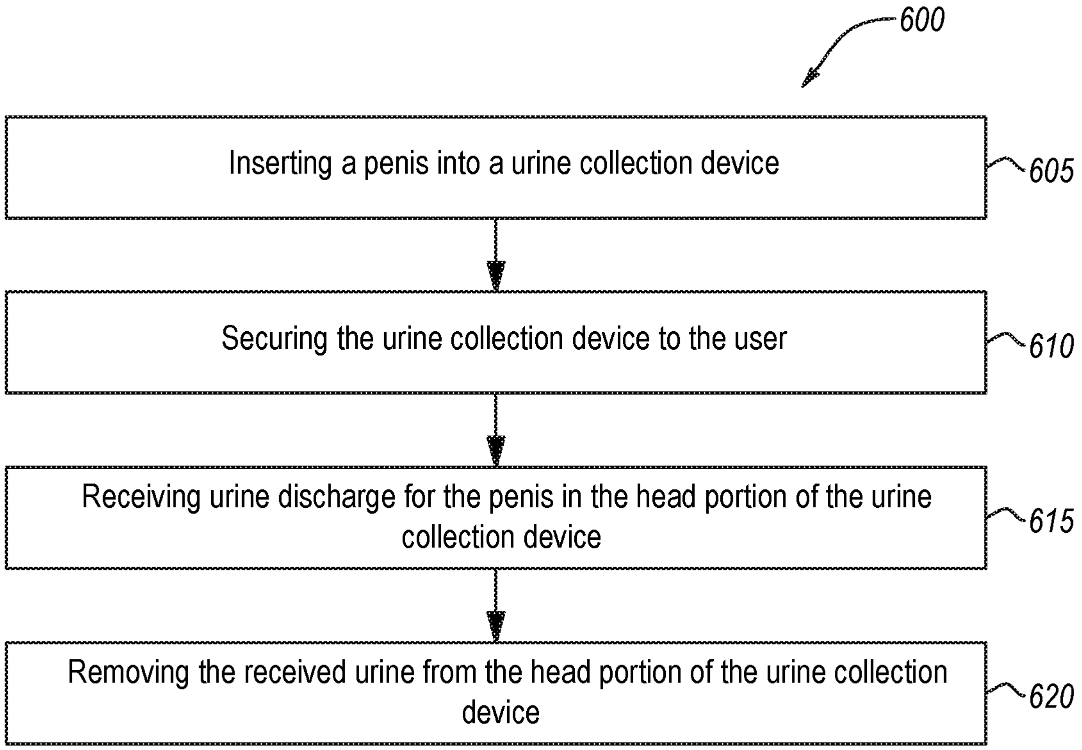
FIG. 6 is a flow diagram of a method to making a fluid collection device, according to an embodiment.

FIG. 6 is a flow diagram of a method 600 for collecting fluids. The method 600 includes an act 605 of inserting a penis into a urine collection device. The act 605 may include inserting a penis into a urine collection device such that a head of the penis is disposed within a tubular shaft or a receptacle of the urine collection device and at least a portion of a shaft of the penis is disposed within the tubular shaft of the urine collection device. The tubular shaft of the urine collection device is cylindrical and has an open end and an inner surface, and the receptacle may be connected to the tubular shaft distal to the open end of the tubular shaft. The method 600 also includes an act 610 of securing the urine collection device to the user. The act 610 of securing the urine collection device to the user may include adjusting the tubular shaft from a first configuration having a first inner circumference sized larger than a circumference of the shaft of the penis to a second configuration having a second inner circumference smaller than the first inner circumference and contacting the penis with the inner surface of the tubular shaft. The method 600 also includes an act 615 of receiving urine discharged from the penis in the receptacle of the urine collection device. The method also includes an act 620 of removing the received urine from the receptacle of the urine collection device. In some embodiments, the method 600 also includes an act of fluidly coupling a vacuum source to a suction port on the receptacle of the urine collection device to assist in withdrawing the urine from the receptacle via the fluid outlet.

Acts 605, 610, 615, and 620 of the method 600 are for illustrative purposes. For example, the acts 605, 610, 615, and 620 of the method 600 can be performed in different orders, split into multiple acts, modified, supplemented, or combined. In an embodiment, one or more of the acts 605, 610, 615, and 620 of the method 600 can be omitted from the method 600. Any of the acts 605, 610, 615, and 620 can include using any of the fluid collection devices or systems disclosed herein.

Also disclosed herein is are one or more embodiments of a method of manufacturing a urine collection device. The urine collection device manufactured according to the method may include any urine collection devices described herein, such as the urine collection devices 100, 200, 300, 400. In some embodiments, the method of manufacturing a urine collection device includes providing a tubular shaft having an open end and an inner surface, the tubular shaft being adjustable between a first configuration having a first inner circumference sized to receive at least a portion of a penis within the tubular shaft and a second configuration having a second inner circumference smaller than the first inner circumference and sized to contact the penis with the inner surface.

In some embodiments, providing a tubular shaft having an open end and an inner surface includes providing a cylindrical, helically wound braid of a plurality of a strips of one or more materials. More particularly, providing a cylindrical, helically wound braid of a plurality of a strips of one or more materials may include helically braiding the plurality of strips of one or more materials to form the cylindrical, helically wound braid of a plurality of a strips of one or more materials that is adjustable between the first configuration having the first inner circumference sized to receive at least a portion of the penis within the tubular shaft and the second configuration having the second inner circumference smaller than the first inner circumference and sized to contact the penis with the inner surface.

In some embodiments, the method may include securing a fluid impermeable layer radially outwardly to the cylindrical, helically wound braid of the plurality of strips of one or more materials of the tubular shaft. In some embodiments, the method of manufacturing a urine collection device may include securing a wicking material to the tubular shaft such that the wicking material defines at least a portion of the inner surface of the tubular shaft. In some embodiments, the method may include securing a padded material to the tubular shaft such that the padded material defines at least a portion of the inner surface of the tubular shaft. In some embodiments, the method of manufacturing a urine collection device may include securing a fluid impermeable layer positioned within the cylindrical, helically wound braid of the plurality of strips of one or more materials such that the fluid impermeable layer defines at least a portion of the inner surface of the tubular shaft.

In some embodiments, the method may include coating at least an outer surface of each strip of one or more materials of the plurality of strips of one or more materials with at least one of a hydrophobic coating or a fluid impermeable coating before the cylindrical, helically wound braid of the plurality of strips of one or more materials is formed. In some embodiments, the method o may include coating the cylindrical, helically wound braid of the plurality of strips of one or more materials with at least one of a hydrophobic coating or a fluid impermeable coating after the cylindrical, helically wound braid of the plurality of strips of one or more materials is formed. In some embodiments, the method of manufacturing a urine collection device may include securing one or more support wires to the tubular shaft to extend longitudinally through the cylindrical, helically wound braid of the plurality of strips of one or more materials.

The method may include connecting a receptacle to the tubular shaft distal to the open end, the receptacle being configured to collect urine discharged from the penis when the penis is positioned within the tubular shaft. In some embodiments, connecting a receptacle to the tubular shaft distal to the open end may include connecting the receptacle to the tubular shaft with at least one of an ultrasonic weld, a heat weld, or an adhesive.

As used herein, the term "about" or "substantially" refers to an allowable variance of the term modified by "about" or "substantially" by ±10% or ±5%. Further, the terms "less than," "or less," "greater than," "more than," or "or more" include, as an endpoint, the value that is modified by the terms "less than," "or less," "greater than," "more than," or "or more."

While various aspects and embodiments have been disclosed herein, other aspects and embodiments are contemplated. The various aspects and embodiments disclosed herein are for purposes of illustration and are not intended to be limiting.

What is claimed is:

1. A urine collection device, comprising:

a tubular shaft having an open end and an inner surface, the tubular shaft being adjustable between a first configuration having a first inner circumference sized to receive at least a portion of a penis within the tubular shaft and a second configuration having a second inner circumference smaller than the first inner circumference and sized to contact the penis with the inner surface, wherein the tubular shaft further includes a wicking material defining at least a portion of the inner surface of the tubular shaft, an outer layer that is fluid impermeable, and a cylindrical, helically wound braid of a plurality of strips of one or more materials positioned between the wicking material and the outer layer; and a receptacle connected to the tubular shaft distal to the open end, the receptacle being configured to collect urine discharged from the penis when the penis is positioned within the tubular shaft, wherein the tubular shaft includes one of:

the outer layer that is fluid impermeable includes an elastic or flexible material secured to opposing ends of the cylindrical, helically wound braid and having a longitudinal length that is at least equal to a maximum longitudinal length of the cylindrical, helically wound braid, the elastic or flexible material of the outer layer being configured to elongate or retract as the cylindrical, helically, wound braid elongates or retracts; or each strip of the plurality of strips comprising a tri-layer strip including the outer layer that is fluid impermeable, the wicking material, and an intermediate pad layer between the outer layer and the wicking material secured together to form the strip.

2. The urine collection device of claim 1, wherein the tubular shaft includes the outer layer that is fluid impermeable positioned radially outwardly to the cylindrical, helically wound braid of the plurality of strips of one or more materials, the outer layer including the elastic or flexible material secured to the opposing ends of the cylindrical, helically wound braid and having the longitudinal length that is at least equal to the maximum longitudinal length of the cylindrical, helically wound braid, the elastic or flexible material of the outer layer being configured to elongate or retract as the cylindrical, helically, wound braid elongates or retracts.

3. The urine collection device of claim 1, wherein the tubular shaft further includes a padded material defining at least a portion of the inner surface of the tubular shaft.

4. The urine collection device of claim 1, wherein the tubular shaft includes a fluid impermeable layer positioned within the cylindrical, helically wound braid of the plurality of strips of one or more materials and defining at least a portion of the inner surface of the tubular shaft.

5. The urine collection device of claim 1, wherein each strip of one or more materials of the plurality of strips of one or more materials is coated on at least an outer surface with at least one of a hydrophobic coating or a fluid impermeable coating before the cylindrical, helically wound braid of the plurality of strips of one or more materials is formed.

6. The urine collection device of claim 1, wherein the cylindrical, helically wound braid of the plurality of strips of one or more materials is coated with at least one of a hydrophobic coating or a fluid impermeable coating after the cylindrical, helically wound braid of the plurality of strips of one or more materials is formed.

7. The urine collection device of claim 1, wherein the tubular shaft further includes one or more support wires extending longitudinally through the cylindrical, helically wound braid of the plurality of strips of one or more materials.

8. The urine collection device of claim 1, wherein at least one strip of the plurality of strips of one or more materials includes a longitudinally extending support wire.

9. The urine collection device of claim 1, wherein the first configuration includes a first longitudinal length and the second configuration includes a second longitudinal length that is greater than the first longitudinal length.

10. The urine collection device of claim 1, wherein the receptacle includes a fluid impermeable layer and a suction port.

11. The urine collection device of claim 10, wherein the receptacle further includes a wicking material defining at least a portion of an inner surface of the receptacle and a pad material positioned between the wicking material and the fluid impermeable layer.

12. The urine collection device of claim 1, further comprising at least one of an ultrasonic weld, a heat weld, or an adhesive connecting the receptacle to the tubular shaft.

13. The urine collection device of claim 1, further comprising an annular flange positioned within the urine collection device and a chamber sized to receive a head of the penis when the penis is positioned within the tubular shaft, the chamber being defined at least partially by a portion of the receptacle and a portion of the annular flange and the annular flange being positioned between the receptacle and the tubular shaft including the cylindrical, helically wound braid, the outer layer that is fluid impermeable, and the wicking material defining at least a portion of the inner surface of the tubular shaft.

14. The urine collection device of claim 1, wherein the tubular shaft includes each strip of the plurality of strips comprising the tri-layer strip including the outer layer that is fluid impermeable, the wicking material, and the intermediate pad layer between the outer layer and the wicking material secured together to form the strip.

15. The urine collection device of claim 14, wherein, in each strip of the plurality of strips, the wicking material includes a gauze material and the intermediate pad layer includes a porous nylon structure or an open cell foam.

16. The urine collection device of claim 14, further comprising at least one of an adhesive, an ultrasonic weld, a heat weld, or stitching securing the outer layer, the wicking material, and the intermediate pad layer of each strip in the plurality of strips.

17. A method, comprising:

inserting a penis into a urine collection device such that at least a portion of a shaft of the penis is disposed within a tubular shaft of the urine collection device, the tubular shaft being cylindrical and having an open end, an inner surface defined at least partially by a wicking material, an outer layer that is fluid impermeable, and a helically wound braid of a plurality of strips of one or more materials positioned between the outer layer and the wicking material, wherein the tubular shaft includes one of:

the outer layer that is fluid impermeable includes an elastic or flexible material secured to opposing ends of the cylindrical, helically wound braid and having a longitudinal length that is at least equal to a maximum longitudinal length of the cylindrical, helically wound braid, the elastic or flexible material of the outer layer being configured to elongate or retract as the cylindrical, helically, wound braid elongates or retracts; or each strip of the plurality of strips comprising a tri-layer strip including the outer layer that is fluid impermeable, the wicking material, and an intermediate pad layer between the outer layer and the wicking material secured together to form the strip;

adjusting the tubular shaft from a first configuration having a first inner circumference sized larger than a circumference of the shaft of the penis to a second configuration having a second inner circumference smaller than the first inner circumference and contacting the penis with at least a portion of the wicking material at least partially defining the inner surface of the tubular shaft;

receiving urine discharged from the penis in a receptacle of the urine collection device connected to the tubular shaft distal to the open end of the tubular shaft; and removing the received urine from the receptacle of the urine collection device.

18. The method of claim 17, further comprising fluidly coupling a vacuum source to a suction port on the receptacle of the urine collection device to assist in withdrawing the urine from the receptacle via a fluid outlet.

19. A method of manufacturing a urine collection device, the method comprising:

providing a tubular shaft having an open end and an inner surface, the tubular shaft being adjustable between a first configuration having a first inner circumference sized to receive at least a portion of a penis within the tubular shaft and a second configuration having a second inner circumference smaller than the first inner circumference and sized to contact the penis with the inner surface, wherein the tubular shaft further includes a wicking material defining at least a portion of the inner surface of the tubular shaft, an outer layer that is fluid impermeable, and a cylindrical, helically wound braid of a plurality of strips of one or more materials positioned between the outer layer and the wicking material, wherein the tubular shaft includes one of:

the outer layer that is fluid impermeable includes an elastic or flexible material secured to opposing ends of the cylindrical, helically wound braid and having a longitudinal length that is at least equal to a maximum longitudinal length of the cylindrical, helically wound braid, the elastic or flexible material of the outer layer being configured to elongate or retract as the cylindrical, helically, wound braid elongates or retracts; or each strip of the plurality of strips comprising a tri-layer strip including the outer layer that is fluid impermeable, the wicking material, and an intermediate pad layer between the outer layer and the wicking material secured together to form the strip; and connecting a receptacle to the tubular shaft distal to the open end, the receptacle being configured to collect urine discharged from the penis when the penis is positioned within the tubular shaft.

20. The method of claim 19, wherein providing a tubular shaft having an open end and an inner surface includes helically braiding the plurality of strips of one or more materials to form the cylindrical, helically wound braid of a plurality of strips of one or more materials that is adjustable between the first configuration having the first inner circumference sized to receive at least a portion of the penis within the tubular shaft and the second configuration having the second inner circumference smaller than the first inner circumference and sized to contact the penis with the inner surface.

21. The method of claim 20, further comprising securing the outer layer that is fluid impermeable radially outwardly to the cylindrical, helically wound braid of the plurality of strips of one or more materials of the tubular shaft.

22. The method of claim 20, further comprising securing a fluid impermeable layer positioned within the cylindrical, helically wound braid of the plurality of strips of one or more materials such that the fluid impermeable layer defines at least a portion of the inner surface of the tubular shaft.

23. The method of claim 19, further comprising securing the wicking material to the tubular shaft such that the wicking material defines at least a portion of the inner surface of the tubular shaft.

24. The method of claim 19, further comprising securing a padded material to the tubular shaft such that the padded material defines at least a portion of the inner surface of the tubular shaft.

25. The method of claim 19, further comprising coating at least an outer surface of each strip of one or more materials of the plurality of strips of one or more materials with at least one of a hydrophobic coating or a fluid impermeable coating before the cylindrical, helically wound braid of the plurality of strips of one or more materials is formed.

26. The method of claim 19, further comprising coating the cylindrical, helically wound braid of the plurality of strips of one or more materials with at least one of a hydrophobic coating or a fluid impermeable coating after the cylindrical, helically wound braid of the plurality of strips of one or more materials is formed.

27. The method of claim 19, further comprising securing one or more support wires to the tubular shaft to extend longitudinally through the cylindrical, helically wound braid of the plurality of strips of one or more materials.

28. The method of claim 19, wherein connecting a receptacle to the tubular shaft distal to the open end includes connecting the receptacle to the tubular shaft with at least one of an ultrasonic weld, a heat weld, or an adhesive.

* * * * *